(12) United States Patent
Srivastava

(10) Patent No.: US 6,797,480 B1
(45) Date of Patent: Sep. 28, 2004

(54) PURIFICATION OF HEAT SHOCK/STRESS PROTEIN CELL SURFACE RECEPTORS AND THEIR USE AS IMMUNOTHERAPEUTIC AGENTS

(75) Inventor: Pramod K. Srivastava, Avon, CT (US)

(73) Assignee: University of Connecticut Health Center, Farmington, CT (US)

( * ) Notice: Subject to any disclaimer, the term of this patent is extended or adjusted under 35 U.S.C. 154(b) by 0 days.

(21) Appl. No.: 09/411,075

(22) Filed: Oct. 4, 1999

Related U.S. Application Data
(60) Provisional application No. 60/103,115, filed on Oct. 5, 1998.

(51) Int. Cl.[7] ................................................ G01N 33/53
(52) U.S. Cl. ............................. 435/7.1; 436/4; 436/6; 436/7.2; 436/325; 436/372.3; 424/9.2; 424/184.1; 424/278.1; 514/2
(58) Field of Search .......................... 435/6, 4, 7.1, 7.2, 435/325, 372.3; 424/9.2, 184.1, 278.1; 514/2

(56) References Cited

U.S. PATENT DOCUMENTS

| | | | |
|---|---|---|---|
| 5,525,490 A | * 6/1996 | Erickson et al. | ............... 435/29 |
| 5,750,119 A | 5/1998 | Srivastava | ............... 424/277.1 |
| 5,961,979 A | 10/1999 | Srivastava | ............... 424/193.1 |
| 2002/0001841 A1 | 1/2002 | Kaltoft et al. | ............... 435/366 |

FOREIGN PATENT DOCUMENTS

| | | |
|---|---|---|
| WO | WO 95/24923 | 9/1995 |
| WO | WO 96/10411 | 4/1996 |
| WO | WO 96/34099 | 10/1996 |
| WO | WO 97/10000 | 3/1997 |
| WO | WO 97/10002 | 3/1997 |
| WO | WO 98/46739 | 7/1997 |
| WO | WO 98/42752 | 10/1998 |
| WO | WO 99/49881 | 10/1999 |

OTHER PUBLICATIONS

Alberts et al., Molecular Biology of the Cell, 3rd Ed., 1994, Garland Publishing, Inc. NY, pp. 729–731.
Picard et al., 1990. Reduced Levels of Hsp90 Compromise Steroid Receptor Action in vivo. Nature 348: 166–168.
Pratt and Toft, 1997, Steroid Receptor Interactions with Heat Shock Protein and Immunophilin Chaperones. Endocr Rev. 1997, 18:306–60.
Tsai and O'Malley, Molecular Mechanisms of Action of Steroid/Thyroid Receptor Superfamily Members. Annu. Rev. Biochem., 1994, 63:451–486.
Arnold D, Faath S, Rammensee H, Schild H, "Cross–priming of minor histocompatibility antigen–specific cytotoxic T cells upon immunization with the heat shock protein gp96", J Exp Med. Sep 1 1995;182(3):885–9.

Arnold–Schild H, "Receptor–mediated endocytosis of heat shock proteins by antigen presenting cells", International Conference on Heat Shock, Proteins in Immune Response Oct. 12–15, 1998; Farmington, CT.
Arnold–Schild D. et al., "Cutting edge: receptor–mediated endocytosis of heat shock proteins by professional antigen–presenting cells", J. Immunol. 1999, 162: 3757–3760.
Bevan MJ, "Antigen presentation to cytotoxic T lymphocytes in vivo", J Exp Med. Sep.1, 1995;182(3):639–41.
Binder RJ et al., "Receptor–dependent and receptor–independent re–presentation of heat shock protein–chaperoned peptides", International Conference on Heat Shock Proteins in Immune Response Oct. 12–15, 1998; Farmington, Ct.
Binder RJ et al., "Receptor dependent and receptor independent re–presentation of heat shock protein–chaperoned peptides", Cancer Vaccine Week 1998: An International Symposium Sponsored by the Cancer Research Institute. Oct. 5–9 1998; Abstract No. P3–60.
Blachere NE et al., "Heat shock protein–peptide complexes, reconstituted in vitro, elicit peptide–specific cytotoxic T lymphocyte response and tumor immunity", J Exp Med. Oct. 20, 1997;186(8):1315–22.
Breloer M et al., "In vivo and in vitro activation of T cells after administration of Ag–negative heat shock proteins", J Immunol. Mar. 15; 1999 162(6):3141–7.
Bruner KL, Derfoul A, Robertson NM, Guerriero G, Fernandes–Alnemri T, Alnemri ES, Litwack G, "The unliganded mineralocorticoid receptor is associated with heat shock proteins 70 and 90 and the immunophilin FKBP–52", Recept Signal Transduct. 1997; v7(2):85–98.
Ciupitu AM et al., "Immunization with a lymphocytic choriomeningitis virus peptide mixed with heat shock protein 70 results in protective antiviral immunity and specific cytotoxic T lymphocytes", J Exp Med. Mar 2 1998;187(5):685–91.
Janetzki S et al., "Generation of tumor–specific cytotoxic T lymphocytes and memory T cells by immunization with tumor–derived heat shock protein gp96", J Immunother. Jul 1998;21(4):269–76.

(List continued on next page.)

Primary Examiner—James Ketter
Assistant Examiner—David A. Lambertson
(74) Attorney, Agent, or Firm—Jones Day

(57) ABSTRACT

The present invention relates to receptors for heat shock proteins (HSPs), such as gp96, Hsp70 and Hsp90. The heat shock receptor is associated with the cell membranes of a subset of antigen presenting cells, such as macrophages and dendritic cells. The present invention relates to the use of the heat shock protein receptor positive cells, heat shock protein receptor protein, and heat shock protein receptor genes in methods for screening a molecule for the ability to modulate heat shock protein levels or activities.

60 Claims, 10 Drawing Sheets

OTHER PUBLICATIONS

Figure 1A:
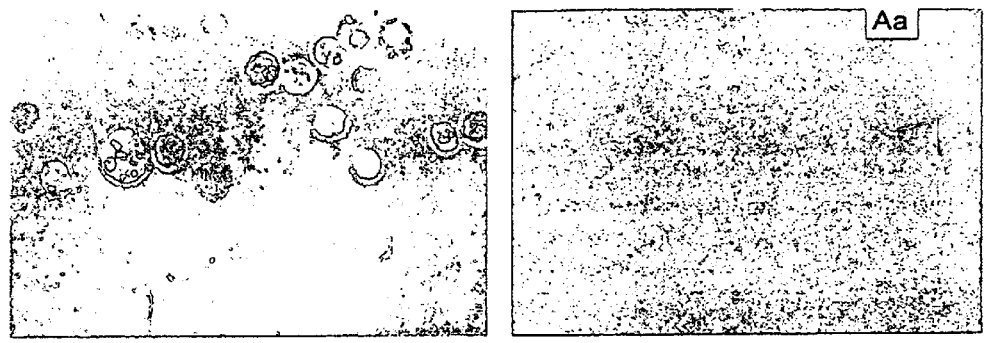

Lammert E et al; "Expression levels of stress protein gp96 are not limiting for major histocompatibility complex class I–restricted antigen presentation", Eur J Immunol. Apr. 1996;26(4):875–9.

Nair SC, Rimerman RA, Toran EJ, Chen S, Prapapanich V, Butts RN, Smith DF, "Molecular cloning of human FKBP51 and comparisons of immunophilin interactions with Hsp90 and Progesterone receptor", Mol Cell Biol. Feb. 1997;17(2):594–603.

Nicchitta CV, "Biochemical, cell biological and immunological issues surrounding the endoplasmic reticulum chaperone GRP94/gp96", Curr Opin Immunol. Feb. 1998;10(1):103–9.

Prapapanich V, Chen S, Nair SC, Rimerman RA, Smith DF, "Molecular cloning of human p48, a transient component of porgesterone receptor complexes and an Hsp70–binding protein", Mol Endocrinol. Apr. 1996 10(4):420–31.

Srivastava PK et al., "Heat shock proteins come of age: primitive functions acquire new roles in an adaptive world", Immunity. Jun. 1998:8(6):657–65.

Srivastava PK, "Heat shock proteins in Immune response to cancer: the Fourth Paradigm", Experientia. Nov. 30, 1994;50(11–12):1054–60.

Srivastava PK and Udono H, "Heat shock protein–peptide complexes in cancer immunotherapy", Curr Opin Immunol. Oct. 1994;6(5):728–32.

Srivastava PK et al., "Heat shock proteins transfer peptides during antigen processing and CTL priming", Immunogenetics. 1994;39(2):93–8.

Srivastava PK, "Peptide–binding heat shock proteins in the endoplasmic reticulum: role in immune response to cancer an in antigen presentation", Adv Cancer Res. 1993;62:153–77.

Srivastava PK et al., "Stress–induced proteins in immune response to cancer", Curr Top Microbiol Immunol. 1991;167:109–23.

Srivastava PK et al., "Individually distinct transplantation antigens of chemically induced mouse tumors", Immunol Today. Mar. 1988; 9(3):78–83.

Srivastava PK et al., "Chromosomal assignment of the gene encoding the mouse tumor rejection antigen gp96" Immunogenetics. 1988;28(3):205–7.

Srivastava PK et al., "5'–structural analysis of genes encoding polymorphic antigens of chemically induced tumors", Proc. Natl Acad Sci USA. Jun. 1987;84(11):3807–11.

Srivastava PK et al., "Tumor rejection antigens of chemically induced sarcomas of inbred mice", Proc Natl Acad Sci USA. May 1986;83(10):3407–11.

Suto R et al., "A mechanism for the specific immunogenicity of heat shock protein–chaperoned peptides", Science. Sep. 15, 1995;269(5230):1585–8.

Udono H et al., "Comparison of tumor–specific immunogenicities of stress–induced proteins gp96, hsp90, and hsp70", J Immunol. Jun. 1, 1994;152(11):5398–403.

Udono H et al., "Heat shock protein 70–associated peptides elicit specific cancer immunity", J Exp Med. Oct. 1, 1993; 178(4):1391–6.

Ullrich SJ et al., "A mouse tumor–specific transplantation antigen is a heat shock–related protein", Proc Natl Acad Sci USA. May 1986;83(10):3121–5.

Wassenberg JJ et al. Receptor mediated and fluid phase pathways for internalization of the ER Hsp90 chaperone GRP94 in murine macrophages. J Cell Sci. Jul. 1999;112 (Pt 13):2167–75.

Wormmeester J, Stiekema F, de Groot C, "Immunoselective cell separation", Methods Enzymol. 1990;184:314–9.

Zeiner M, Gebauer M, Gehring U, "Mammalian protein RAP46: an interaction partner and modulator of 70 kDa heat shock proteins", EMBO J. Sep. 15, 1997;16(18):5483–90.

(National Center for Biotechnology Information) Genbank Accession No. X15187. Human tra1 mRNA for human homologue of murine tumor rejection antigen gp96. Database [Online]. Last update: Mar. 31, 1995. Accessed on: Jan. 12, 1999.

(National Center for Biotechnology Information) Genbank Accession No. U16277. Mus musculus 78 kDa glucose–regulated protein (grp78) gene, promoter region and partial cds. Database [Online]. Last update: Sep. 29, 1995. Accessed on: Jan. 12, 1999.

(National Center for Biotechnology Information) Genbank Accession No. M19645. Human 78 kdalton glucose–regulated protein (GRP78) gene, complete cds. Database [Online]. Last update: Nov. 8, 1994. Accessed on: Jan. 12, 1999.

(National Center for Biotechnology Information) Genbank Accession No. M35021. Mouse heat shock protein 70.1 (hsp70.1) gene, complete cds. Database [Online]. Last update: Mar. 26, 1994. Accessed on: Jan. 12, 1999.

(National Center for Biotechnology Information) Genbank Accession No. M24743. Human MHC class III heat protein HSP70–1 gene, 5'end. Database [Online]. Last update: Jan. 7, 1995. Accessed on: Jan. 12, 1999.

(National Center for Biotechnology Information) Genbank Accession No. M16370. Mouse polymorphic tumor rejection antigen (gp96), 5'end. Database [Online]. Last update: Apr. 27, 1993. Accessed on: Jan. 12, 1999.

Choi et al., 1993, "A comparison of the roles of the low density lipoprotein (LDL) receptor and the LDL receptor–realted protein/ alpha–2–macroglobulin receptor in chylomicron remnant removal in the mouse in vivo." J. Biol. Chem. 268(21):15804–15811.

Hanover et al., 1986, "Monoclonal antibodies against a glycoprotein localized in coated pits and endocytic vesicles inhibit alpha2–macroglobulin binding and uptake", J. of Biol. Chem. 261(35): 16732–16737.

Herz et al., 1991, "39–kDa protein modulates binding of ligands to low density lipoprotein receptor–related protein/ alpha–2–macroglobulin receptor," J. Biol. Chem. 266(31):21232–21238.

Hofer et al., "Members of the low density lipoprotein receptor family mediate cell entry of a minor–group common cold virus." Proc. Natl. Acad. Sci. USA. 91:1839–1842.

Horn et al., 1995, "Analysis of the binding of Pro–urokinase and urokinase–plasminogen activator inhibitor–1 complex to the low density lipoprotein receptor–related protein using a Fab fragment selected from a phage–displayed Fab library", J. of Biol. Chem. 270 (20): 11770–11775.

Huang et al., 1996, "The immunodominant major histocompatability complex class I–restricted antigen of a murine colon tumor derives from an endogenous retroviral gene product", Proc. Natl. Acad. Sci. USA. 93:9730–9735.

Kounnas et al., 1992, "The alpha–2–macroglobulin receptor/low density lipoprotein receptor–related binds and internalizes Pseudomonas exotoxin A." J. Biol. Chem. 267(18)12420–12423.

Moestrup et al., 1991, Analysis of Ligand Recognition by the purified alpha–2 M–macroglobulin receptor (low density lipoprotein receptor–related protein). J. Biol. Chem. 266(21):14011–14017.

Orth et al., 1994, "Low density lipoprotein receptor–related protein is necessary for the internalization of both tissue–type plasminogen activator–inhibitor complexes and free tissue–type plasminogen activator." J. Biol. Chem. 269(33):21117–21122.

Warshawaky et al., 1993, "Identification of domains in the 39–kDa protein that inhibit the binding of ligands to the low density lipoprotein receptor–related protein," J. Biol. Chem. 268(29):22046–22054.

Williams et al., 1994, "The Carboxyl–terminal domain of lipoprotein lipase binds to the low density liporprotein receptor–related protein alpha–2–macroglobulin receptor (LRP) and mediates binding of normal very low density lipoproteins to LRP." J. Biol. Chem. 269(12):8653–8658.

* cited by examiner

PURIFICATION OF HEAT SHOCK/STRESS PROTEIN CELL SURFACE RECEPTORS AND THEIR USE AS IMMUNOTHERAPEUTIC AGENTS

This application claims benefit under 35 U.S.C. §119(e) to provisional patent application No. 60/103,115, filed Oct. 5, 1998 (now expired), which is incorporated by reference herein in its entirety.

The invention was made with government support under grant numbers CA44786 and CA64394 awarded by the National Institutes of Health. The government has certain rights in the invention.

1. INTRODUCTION

The present invention relates to the cell surface receptors for heat shock proteins (HSPs), such as gp96, Hsp70 and Hsp90, cells that express the Hsp receptor, genes that encode the Hsp receptor, and antibodies and other molecules that bind the receptor. The invention also relates to the diagnostic uses of these molecules in immunotherapy. HSP cell surface receptors recognize and bind to HSPs and are associated with the cell membranes of a subset of macrophages and dendritic cells. HSP cell surface receptors can have uses in the diagnosis and treatment of cancer and proliferative diseases.

2. BACKGROUND OF THE INVENTION

2.1. Heat Shock Proteins

Heat shock proteins (HSPs), also referred to as stress proteins, were first identified as proteins synthesized by cells in response to heat shock. To date, five families of HSP have been identified based on molecular weight, Hsp 100, Hsp90, Hsp70, Hsp60, and smHsp. Many members of these families were found subsequently to be induced in response to other stressful stimuli including nutrient deprivation, metabolic disruption, oxygen radicals, and infection with intracellular pathogens. (See Welch, May 1993, Scientific American 56–64; Young, 1990, Annu. Rev. Immunol. 8:401–420; Craig, 1993, Science 260:1902–1903; Gething et al., 1992, Nature 355:33–45; and Lindquist et al., 1988, Annu. Rev. Genetics 22:631–677).

The major HSPs can accumulate to very high levels in stressed cells, but they occur at low to moderate levels in cells that have not been stressed. For example, the highly inducible mammalian Hsp70 is hardly detectable at normal temperatures but becomes one of the most actively synthesized proteins in the cell upon heat shock (Welch et al., 1985, J. Cell. Biol. 101:1198–1211). In contrast, Hsp90 and Hsp60 proteins are abundant at normal temperatures in most, but not all, mammalian cells and are further induced by heat (Lai et al., 1984, Mol. Cell. Biol. 4:2802–2810; van Bergen en Henegouwen et al., 1987, Genes Dev. 1:525–531).

Studies on the cellular response to heat shock and other physiological stresses revealed that the HSPs are involved not only in cellular protection against these adverse conditions, but also in essential biochemical and immunological processes in unstressed cells. HSPs accomplish different kinds of chaperoning functions. For example, members of the Hsp70 family, located in the cell cytoplasm, nucleus, mitochondria, or endoplasmic reticulum (Lindquist, S. et al., 1988, Ann. Rev. Genetics 22:631–677), are involved in the presentation of antigens to the cells of the immune system, and are also involved in the transfer, folding and assembly of proteins in normal cells. HSPs are capable of binding proteins or peptides, and releasing the bound proteins or peptides in the presence of adenosine triphosphate (ATP) or low pH.

Other stress proteins involved in folding and assembly of proteins include, for example, protein disulfide isomerase (PDI), which catalyzes disulfide bond formation, isomerization, or reduction in the endoplasmic reticulum (Gething et al., 1992, Nature 355:33–45).

Heat shock proteins are among the most highly conserved proteins in existence. For example, DnaK, the Hsp70 from E. coli has about 50% amino acid sequence identity with Hsp70 proteins from excoriates (Bardwell et al., 1984, Proc. Natl. Acad. Sci., 81:848–852). The Hsp60 and Hsp90 families also show similarly high levels of intra-family conservation (Hickey et al., 1989, Mol. Cell. Biol., 9:2615–2626; Jindal, 1989, Mol. Cell. Biol., 9:2279–2283). In addition, it has been discovered that the Hsp60, Hsp70 and Hsp90 families are composed of proteins that are related to the stress proteins in sequence, for example, having greater than 35% amino acid identity, but whose expression levels are not altered by stress.

2.2. Immunogenicity of HSP-Peptide Complexes

Srivastava et al. demonstrated immune response to methylcholanthrene-induced sarcomas of inbred mice (1988, Immunol. Today 9:78–83). In these studies, it was found that the molecules responsible for the individually distinct immunogenicity of these tumors were glycoproteins of 96 kDa (gp96) and intracellular proteins of 84 to 86 kDa (Srivastava et al., 1986, Proc. Natl. Acad. Sci. USA 83:3407–3411; Ullrich et al., 1986, Proc. Natl. Acad. Sci. USA 83:3121–3125). Immunization of mice with gp96 or p84/86 isolated from a particular tumor rendered the mice immune to that particular tumor, but not to antigenically distinct tumors. Isolation and characterization of genes encoding gp96 and p84/86 revealed significant homology between them, and showed that gp96 and p84/86 were, respectively, the endoplasmic reticular and cytosolic counterparts of the same heat shock proteins (Srivastava et al., 1988, Immunogenetics 28:205–207; Srivastava et al., 1991, Curr. Top. Microbiol. Immunol. 167:109–123). Further, Hsp70 was shown to elicit immunity to the tumor from which it was isolated but not to antigenically distinct tumors. However, Hsp70 depleted of peptides was found to lose its immunogenic activity (Udono and Srivastava, 1993, J. Exp. Med. 178:1391–1396). These observations suggested that the heat shock proteins are not immunogenic per se, but form noncovalent complexes with antigenic peptides, and the complexes can elicit specific immunity to the antigenic peptides (Srivastava, 1993, Adv. Cancer Res. 62:153–177; Udono, H. et al., 1994, J. Immunol., 152:5398–5403; Suto et al., 1995, Science, 269:1585–1588).

2.3. Immunotherapeutic HSP-Antigen Complexes

Noncovalent complexes of HSPs and peptide, purified from cancer cells, can be used for the treatment and prevention of cancer and have been described in PCT publications WO 96/10411, dated Apr. 11, 1996, and WO 97/10001, dated Mar. 20, 1997 (see also copending U.S. patent applications Ser. No. 08/796,318 (now U.S. Pat. No. 6,017,540) filed Feb. 7, 1997 by Srivastava and Chandawarkar and Ser. No. 08/796,316 (now U.S. Pat. No. 5,830,464) filed Feb. 7, 1997 by Srivastava, each of which is incorporated by reference herein in its entirety). Stress protein-peptide complexes can also be isolated from pathogen-infected cells and used for the treatment and prevention of infection caused by the pathogen, such as viruses, and other intracellular pathogens, including bacteria, protozoa, fungi and parasites. See PCT publication WO 95/24923, dated Sep. 21, 1995. Immunogenic stress protein-peptide complexes can also be prepared by in vitro complexing of 30 stress protein and antigenic peptides, and the uses of such complexes for the treatment and prevention of cancer and infectious diseases has been described in PCT publication WO 97/10000, dated Mar. 20, 1997. The use of stress protein-peptide complexes for sensitizing antigen presenting cells in vitro for use in adoptive immunotherapy is described in PCT publication WO 97/10002, dated Mar. 20, 1997.

Stress protein-peptide complexes have been purified as described previously; see for example, PCT Publication WO 95/24923, dated Sep. 21, 1995. For the purpose of preparing a vaccine against cancer, the amount of immunogenic material obtainable for use is directly related to the amount of starting cancer cells. Since only a small number of cancer cells can be obtained from a subject, especially if the cancer is at an early stage, the supply of cancer cells for producing the HSP-peptide complex is often very limited. Because of this limited supply of cancer cells, the development of new techniques are needed to aid in the process of purifying recombinant HSP-peptide complexes for use in immunotherapy.

For commercial production of a vaccine or therapeutic agent, a constant supply of large amounts of HSP-peptide complexes is advantageous. Thus, there is a need for a dependable long-term source of HSP-peptide complexes that does not depend on availability of fresh cell samples from cancer patients. Readily available purified components of the molecular machinery involved in the elicitation of specific immunity by heat shock protein-peptide complexes will greatly enhance immunotherapeutic techniques when only a very small amounts of tumor tissue is available from a patient.

2.4. Antigen Presentation of HSP-peptide Complexes

Major histocompatibility complex (MHC) molecules present antigens on the cell surface of antigen-presenting cells. Cytotoxic T lymphocytes (CTLs) then recognize MHC molecules and their associated peptides and kill the target cell. Antigens are processed by two distinct antigen processing routes depending upon whether their origin is intracellular or extracellular. Intracellular or endogenous protein antigens, i.e., antigens synthesized within the antigen-presenting cell, are presented by MHC class I (MHCI) molecules to CD8+ cytotoxic T lymphocytes. On the other hand, extracellular or exogenously synthesized antigenic determinants are presented on the cell surface of "specialized" or "professional" APCs (macrophages, for example) by MHC class II molecules to CD4+ T cells (see, generally, Fundamental Immunology, W. E. Paul (ed.), New York: Raven Press, 1984). This compartmental segregation of antigen processing routes is important to prevent tissue destruction that could otherwise occur during an immune response as a result of shedding of neighboring cell MHCI antigens.

The capacity of gp96-peptide complexes to elicit an immune response is dependent upon the transfer of the peptide to MHC class I molecules of antigen-presenting cells (Suto and Srivastava, 1995, supra). Endogenously synthesized antigens chaperoned by gp96 in the endoplasmic reticulum [ER] can prime antigen-specific CD8+ T cells (or MHC I-restricted CTLs) in vivo; this priming of CD8+ T cells requires macrophages. However, the process whereby exogenously introduced gp96-peptide complexes elicit the antigen-specific CD8+ T cell response is not completely understood since there is no established pathway for the translocation of extracellular antigens into the class I presentation machinery. Yet antigenic peptides of extracellular origin associated with HSPs are somehow salvaged by macrophages, channeled into the endogenous pathway, and presented by MHC I molecules to be recognized by CD8+ lymphocytes (Blachere et al., 1997, J. Exp. Med., 186:1315–22).

Little is known about the route the peptides take inside the cell before reaching the class I molecules. There currently exists several proposed mechanisms for the delivery of extracellular peptides to the MHC I molecules for presentation. One model proposed to explain this apparent paradox is that HSP-chaperoned peptides, or fragments thereof, are transferred to MHC I molecules on the cell surface of macrophages, which internalize them and re-present these antigenic peptides to CD8+ T lymphocytes. Another model suggest that soluble extracellular proteins can be trafficked to the cytosol via constitutive macropinocytosis in bone marrow-derived macrophages and dendritic cells (Norbury et al., 1997, Eur. J. Immunol. 27:280–288). Yet another hypothetical model attempts to explain the phenomenon by suggesting that HSPs are taken up by the MHC class I molecules of the macrophage, which finally stimulate the appropriate T cells (Srivastava et al., 1994, Immunogenetics 39:93–98. There is also the hypothesis that the mannose receptor is used in the uptake of gp96 but no mechanism has been proposed for the non-glycosylated HSPs, such as HSP70 (Ciupitu et al., 1998, J. Exp. Med., 187:685–691). Others suggested that a novel intracellular trafficking pathway may be involved for the transport of peptides from the extracellular medium into the lumen of ER (Day et al., 1997, Proc. Natl. Acad. Sci. 94:8064–8069; Nicchitta, 1998, Curr. Opin. in Immunol. 10:103–109). Further suggestions include the involvemnt of phagocytes which (a) possess an ill-defined pathway to shunt protein from the phagosome into the cytosol where it would enter the normal class I pathway; (b) digest ingested material in lysosomes and regurgitate peptides for loading on the surface to class I molecules (Bevan 1995, J. Exp. Med. 182:639–41).

A better understanding of this process and the characterization of specific molecules involved in the uptake of HSPs or HSP-peptide complexes could provide useful reagents and techniques for eliciting specific immunity by HSP and HSP-peptide complexes. The isolation of the heat shock protein receptor and the gene encoding thereof is instrumental to our understanding of the antigen presentation process and the development of novel diagnostic and therapeutic methods.

3. SUMMARY OF THE INVENTION

The present invention is based on the discovery of a receptor that recognizes and binds to heat shock protein. The existence of such an HSP receptor on the cell surface was unexpected because HSPs/stress proteins are generally known to be cytoplasmic and are also known to be very abundant. The receptor is associated with the cell membranes of a subset of macrophages, dendritic cells, and possibly other cell types.

In one embodiment, the invention provides methods for enriching and isolating cells that express the HSP receptor.

In another embodiment, the invention provides methods for isolating the HSP receptor protein. The HSP receptor can be isolated from extracts of HSPR positive cells, and preferably fractions containing the membrane components of HSPR positive cells. Detection of the HSP receptor is accomplished by using antibodies that bind the HSP receptor, or by the assaying for HSP-binding activity. Isolated HSPR protein and fragments thereof are also encompassed by the invention. The invention also provides for antibodies to HSPR positive cells and HSPR protein, and fragments thereof.

In yet another embodiment, the invention provides methods for identifying and isolating nucleic acid molecules encoding HSP receptor, and fragments thereof. Methods to identify such nucleic acid molecules in HSPR positive cells include subtractive hybridization methods, DNA chip technologies, and differential display. To facilitate isolation of the HSPR cDNA, RNA from HSPR positive cells can be used to prepare a cDNA library. Such gene libraries can be screened by hybridization using oligonucleotide probes encoding a fragment of HSPR, or nucleic acid molecules encoding a homologous HSPR. Alternatively, functional screening or expression cloning methods can be applied to screen the libraries. The libraries are constructed and introduced into host cells such that the proteins encoded by the cDNAs are expressed. Labeled antibodies to HSPR or labeled HSP can be used to isolate clones in such gene expression libraries that express a functional HSPR, or a functional portion thereof. hspr gene, and fragments thereof, isolated by the methods of the invention are also encompassed.

The present invention further provides methods of use of the HSPR positive cells, HSPR protein, HSPR antibodies, and hspr gene. HSP receptors may serve to recognize and transport HSP-antigenic peptide complexes for the purpose of presenting such antigenic molecules to cells of the immune system and eliciting an immune response. Thus, HSPR may be used for modulating the immune response. Methods for identifying a molecule that enhances or blocks the function of HSPR are included in the invention. The compositions of the invention may be used in various diagnostic and therapeutic applications in the area of cancer and infectious diseases.

4. BRIEF DESCRIPTION OF THE FIGURES

FIGS. 1A. gp96 receptor positive cells. Light microscopy (left panel), or confocal microscopy (right panel) of gp96 bound to membranes of peritoneal cells of C57/BL6 mice. A) Negative control, unlabelled. B) Negative control, labelled with BSA-biotin. C) gp96-biotin labelled.

Figure 2A:
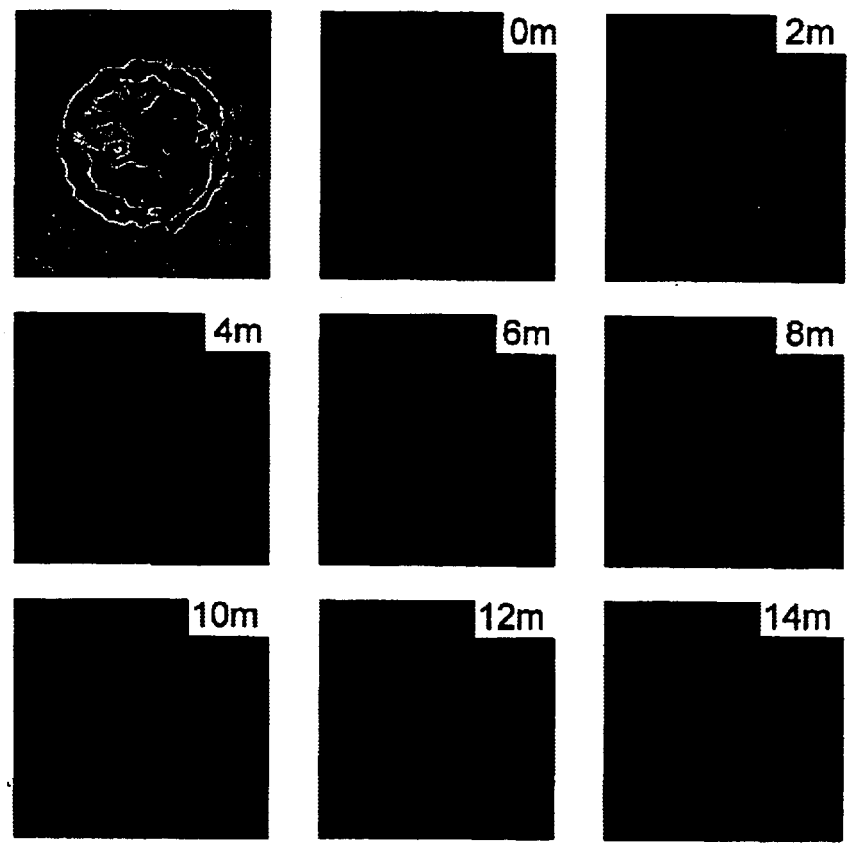
Figure 2B:
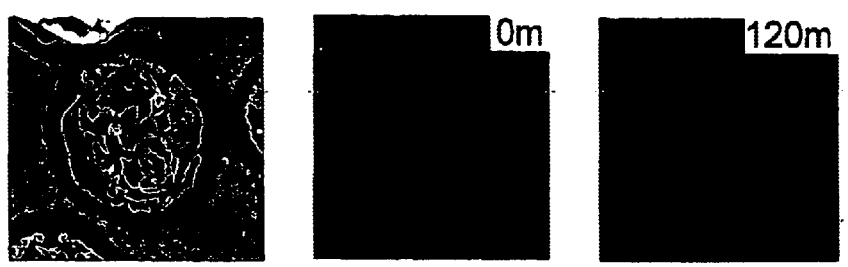

FIGS. 2A–B. Time course of gp96-biotin internalization by peritoneal cells of C57/BL6 mice. A) Top left panel, light microscopy of a peritoneal cell, followed by confocal microscopy of a time course of gp96-biotin uptake by the same cell at 37° C., shown after 0, 2, 4, 6, 8, 10, 12, or 14 mins. B) Left panel, light microscopy of a peritoneal cell, followed by a confocal microscopy time course of gp96-biotin uptake by the same cell at 4° C., labelled for 0, and 120 mins.

Figure 3A:
Figure 3A:
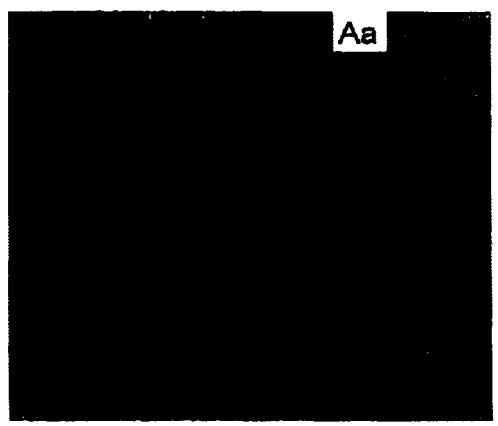
Figure 3B:
Figure 3B:
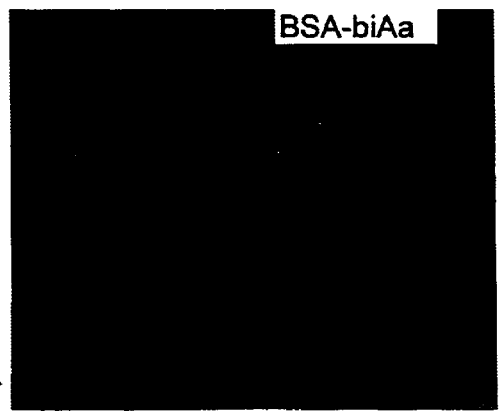

FIGS. 3A–C. gp96 receptor positive cells. Light microscopy (left panel), or confocal microscopy (right panel) of gp96 bound to membranes of peritoneal cells of the transgenic mouse ImmortoMouse. A) Negative control, unlabelled. B) Negative control, labelled with BSA-biotin. C) gp96-biotin labelled.

Figure 4A:
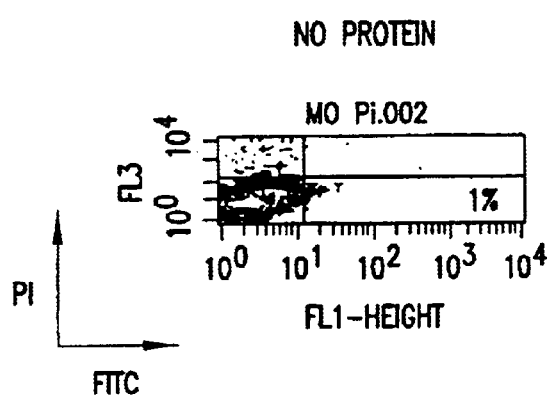
Figure 4B:
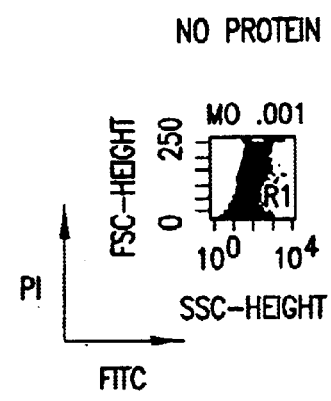
Figure 4C:
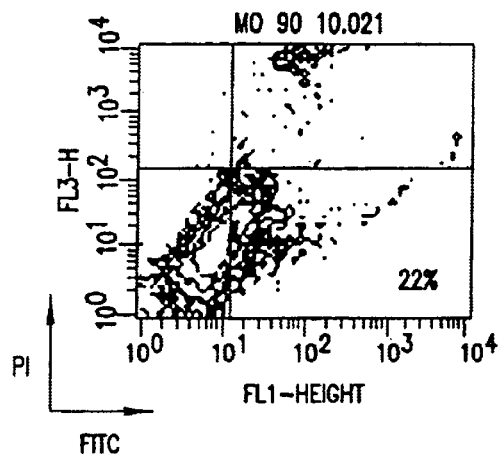
Figure 4D:
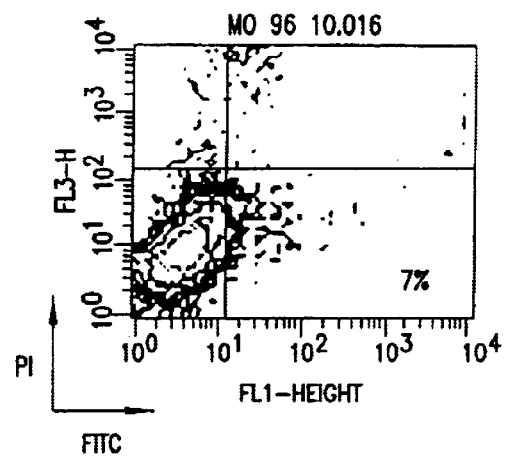
Figure 4E:
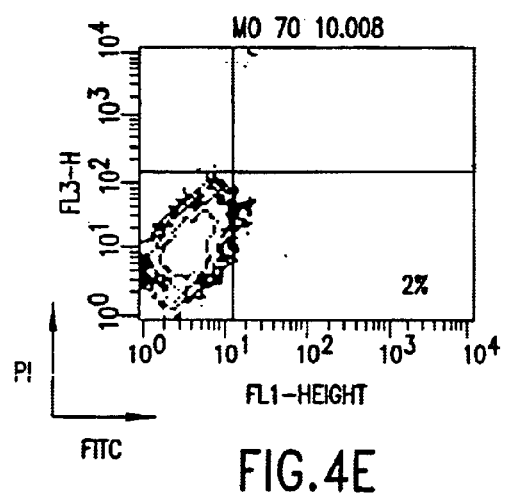
Figure 4F:
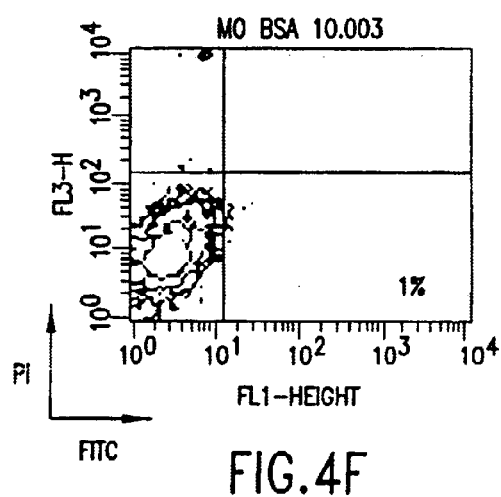
Figure 4G:
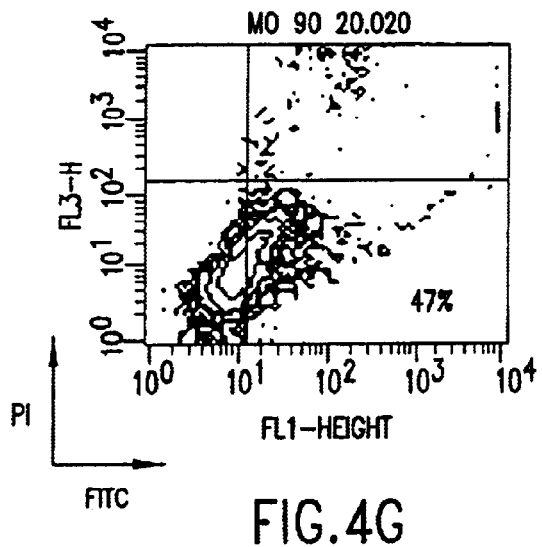
Figure 4H:
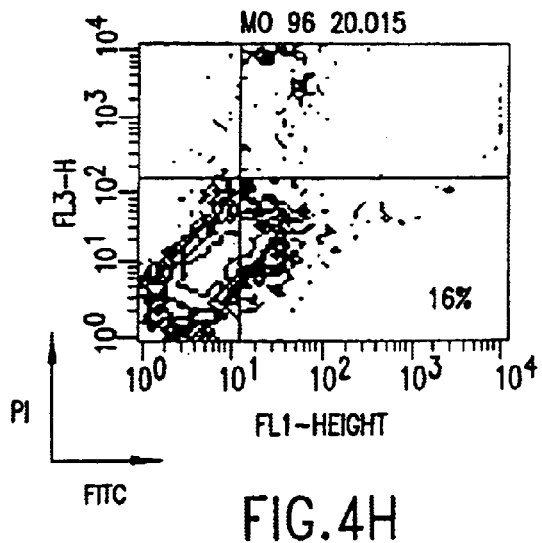
Figure 4I:
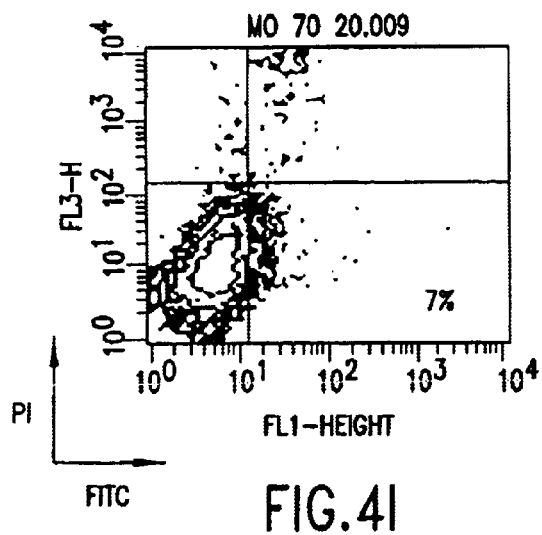
Figure 4J:
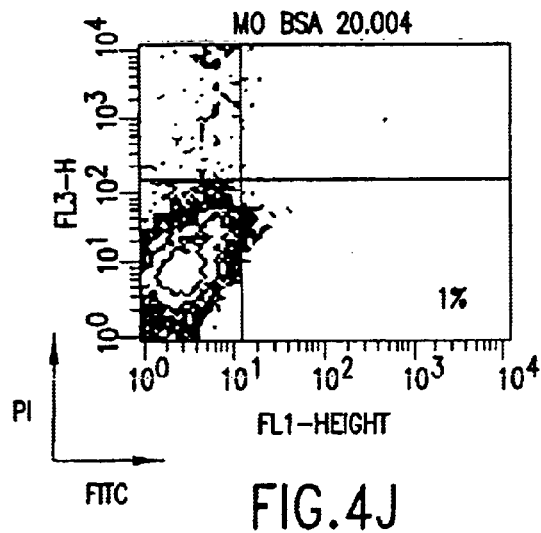
Figure 4K:
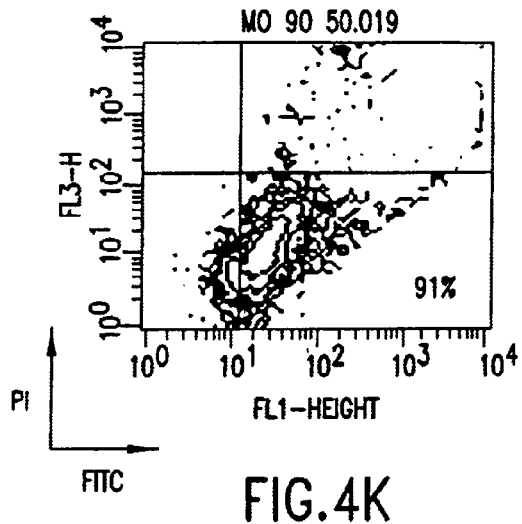
Figure 4L:
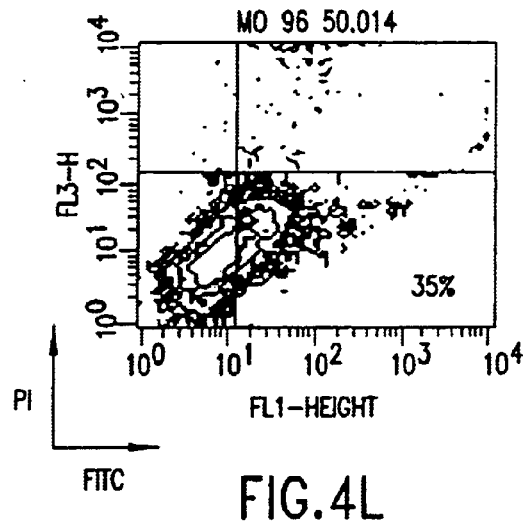
Figure 4M:
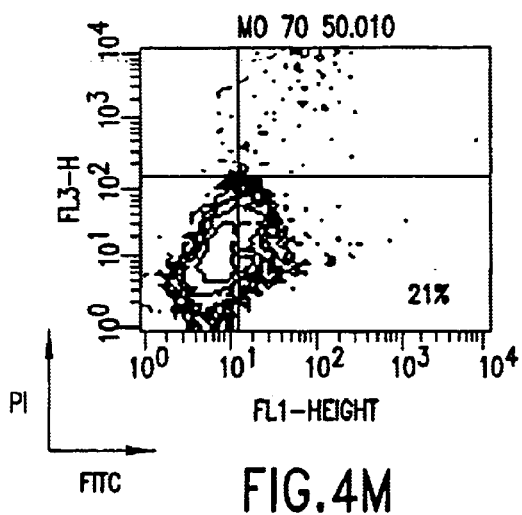
Figure 4N:
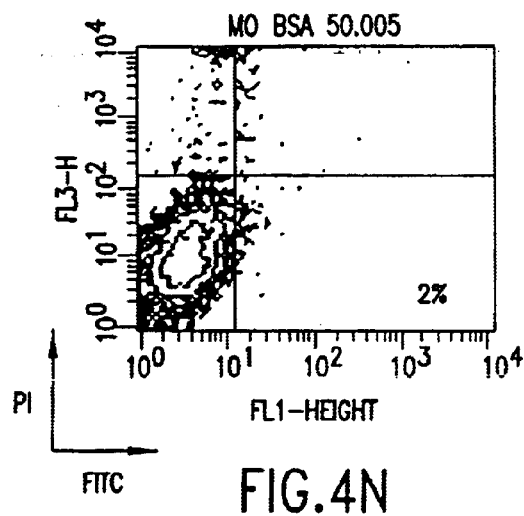
Figure 4O:
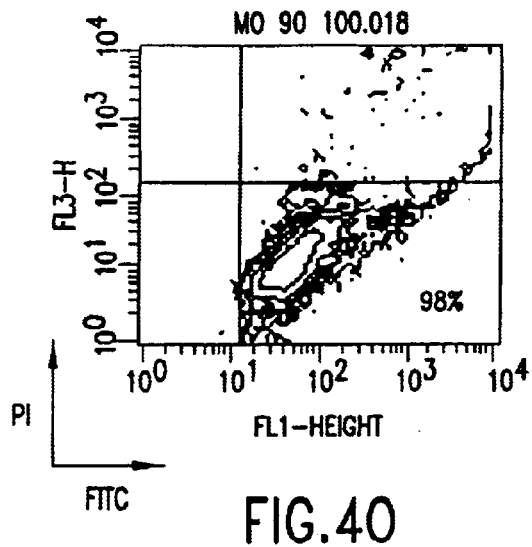
Figure 4P:
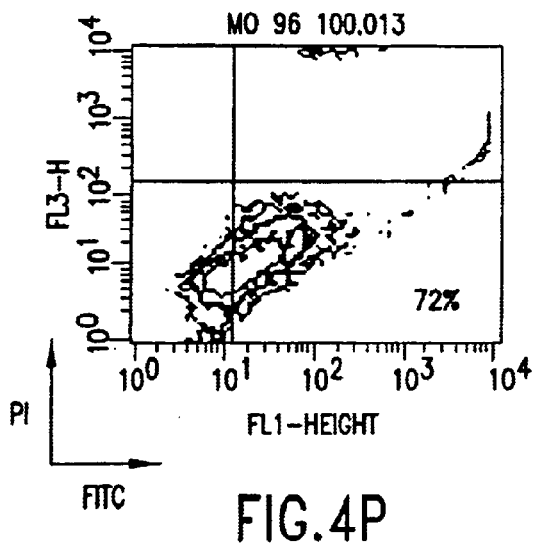
Figure 4Q:
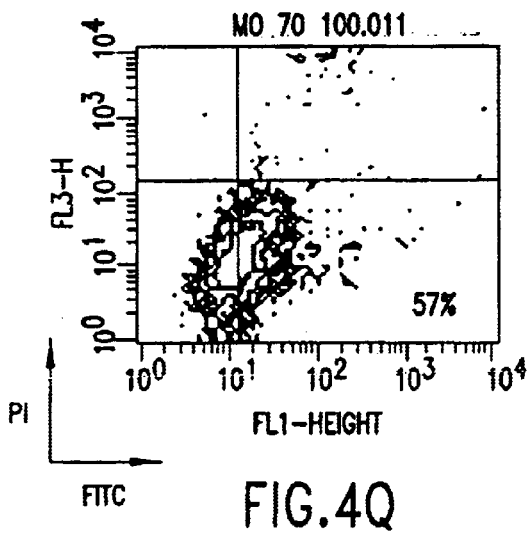
Figure 4R:
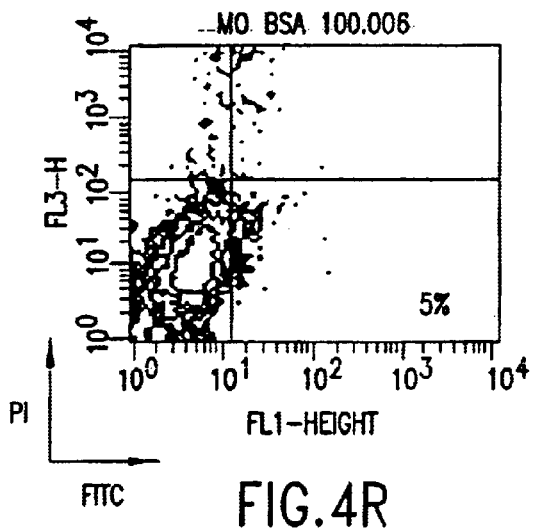
Figure 4S:
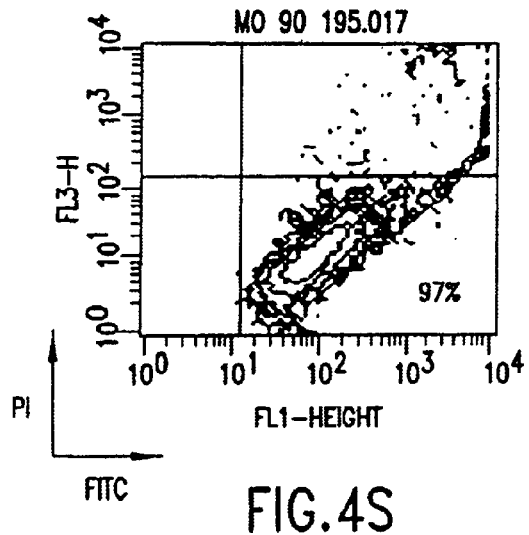
Figure 4T:
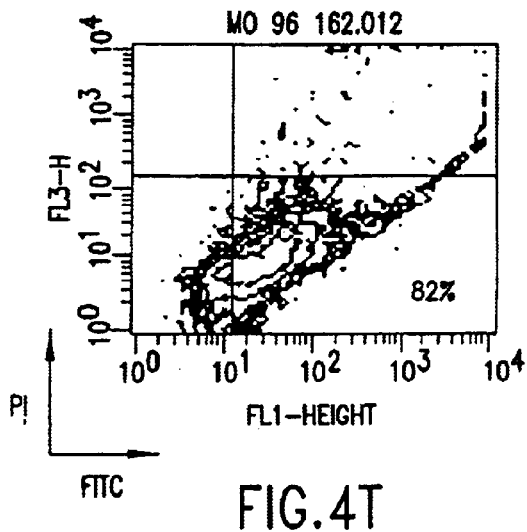
Figure 4U:
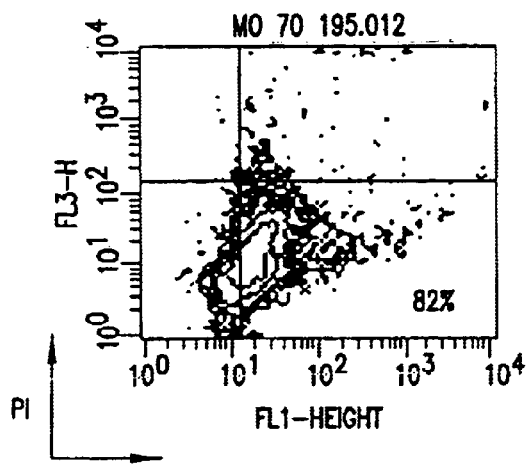
Figure 4V:
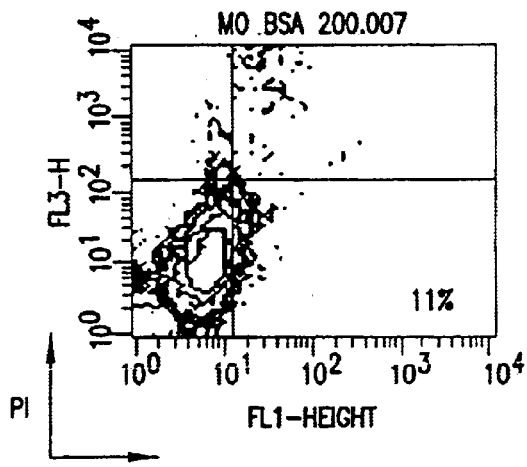

FIG. 4A–V. FacScan analysis of Hsp90 (FIGS. 4C, 4G, 4K, 4O), gp96 (FIGS. 4D, 4H, 4L, 4P, 4T), Hsp70 (FIGS. 4E, 4I, 4M, 4O, 4U), and BSA (FIGS. 4F, 4J, 4N, 4r, 4V) labelled with FITC and pulsed on to Mac-1 positive calls (macrophage) at HSP concentrations of 10 μg/ml (FIGS. 4c–F), 20 μg/ml (FIGS. 4G–J), 50 μg/ml (FIGS. 4K–N), 100 μg/ml (FIGS. 4O–R), and 190 μg/ml (FIGS. 4S–V). X axis measures FITC absorbance; Y axis measures propidium iodine (PI) absorbance. $A–$b, control standards.

Figure 5A:
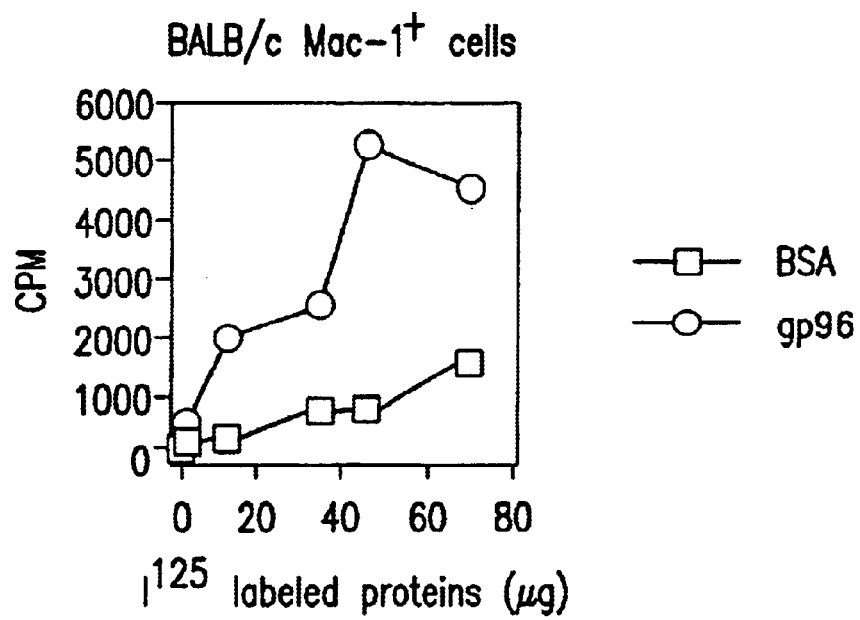
Figure 5B:
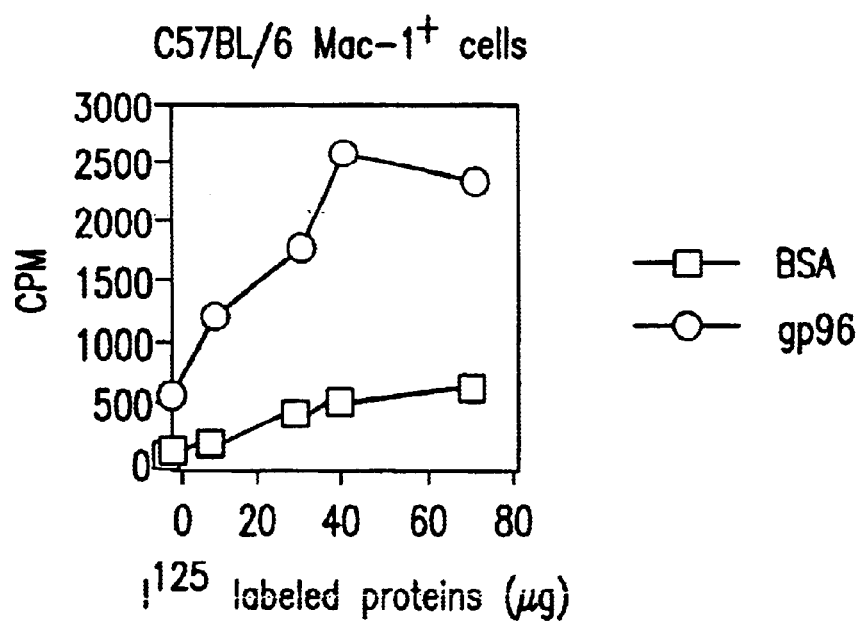

FIG. 5A–B. HSP Receptor saturation by $^{125}$I-labelled gp96 in BALB/c Mac-1+ cells (FIG. 5A) and C57BL/6 Mac-1+ (macrophage) cells (FIG 5B). $^{125}$I-labelled BSA is shown as a negative control.

5. DETAILED DESCRIPTION OF THE INVENTION

The present invention is directed to the identification and isolation of a receptor for heat shock proteins, herein termed HSP receptor or HSPR. As used herein, HSPR can refer to the receptor for any heat shock protein family member, including gp96, Hsp90, Hsp70. The HSP receptors of the invention specifically bind HSPs. The HSPR can also specifically bind a HSP in a non-covalent complex with an antigenic peptide. These proteins are associated with the cell membranes of macrophages and dendritic cells that are involved in antigen presentation.

In order to elucidate the mechanism underlying the presentation of antigenic peptides extracellularly by heat shock proteins, the inventor carried out a series of experiments and identified a specific receptor for heat shock proteins on he surface of a subset of macrophages. The inventor of the present invention noted that certain observations were inconsistent with a "direct transfer" model of HSP-chaperoned peptide antigen presentation. First, the immunogenicity of HSP preparations is dependent on the presence of functional phagocytic cells but not B cells or other nonprofessional antigen-presenting cells, (Udono and Srivastava, 1993, supra; Suto and Srivastava, 1995, supra), whereas free peptides can sensitize all cell types. Second, extremely small quantities of HSP-peptide complexes were effective in eliciting specific immunity, i.e., gp96-chaperoned peptides are several hundred times as effective as free peptides in sensitizing macrophages for CTL recognition, suggesting the possibility of a specific uptake mechanism. Third, gp96-chaperoned peptides elicited an MHC I response that was not limited by the size of peptide. Finally, the processing of gp96-peptide complexes in macrophage was found to be sensitive to Brefeldin A (BFA), which blocks transport through the Golgi apparatus, suggesting that processing occurred through an intercellular mechanism. These observations led to the hypothesis that HSP-chaperoned peptides may be processed internally and re-presented by MHC class I molecules on the cell surfaces of macrophages (Suto and Srivastava, 1995, supra). There is also the hypothesis that the mannose receptor is used in the uptake of gp96 but no mechanism hs been proposed for the non-glycosylated HSPs, such as HSP70 (Ciupitu et al., 1998, J. Exp. Med., 187: 685–691). Others suggested that a novel intracellular trafficking pathway may be involved for the transport of peptides from the extracellular medium into the lumen of ER) Day et al., 1997, Proc. Natl. Acad. Sci. 94:8065–8069; Nicchitta, 1998, Curr. Opin. in Immunol. 10:103–109). Further suggestions include the involvement of phagocytes which (a) possess an ill-defined pathway to shunt protein from the phagosome into the cytosol where it would enter the normal class I pathway; (b) digest ingested material in lysosomes and regurgitate peptides for loading on the surface to class I molecules (Bevan 1995, J. Exp. Med. 192:639–41). The discovery of a receptor for heat shock protein as disclosed herein helps to resolve the paradox of how extracellular antigenic peptides complexed to HSPs can be presented by MHC class I molecules on antigen presenting cells.

The present invention is further directed to the cells that express heat shock protein receptor, herein termed HSPR positive cells. The HSPR positive cells of the invention are present as a subpopulation in a mixture of immune cells which can be isolated by physically separating cells, such as macrophages or dendritic cells, that display HSP receptor activity from those that lack HSP receptor activity. Such HSPR positive cells can be used for treatment of cancer and disease caused by intracellular pathogen.

The present invention is further directed to antibodies against the HSP receptor. Such antibodies can be prepared by immunizing an animal with HSPR positive cells. In turn, antibodies to HSPR can be used to isolate the HSPR proteins and genes of the invention. Antibodies to HSPR can further be used in diagnosis and treatment of cancer and infectious disease.

The present invention is also directed to HSPR proteins. HSPR can be isolated by various methods using the HSPR positive cells and/or the antibodies of the invention. HSPR can be isolated and purified from the membranes of cells that express HSPR, such as macrophages, using a variety of methods. In one aspect of the invention, affinity purification methods based on HSP can be used to isolate HSPR from an extract prepared from HSPR positive cells. In another aspect, an antibody to HSPR bound to a solid support can be used to isolate the HSPR protein.

In another aspect of the invention, differential expression between different cell types can be used to identify proteins expressed in HSPR positive cells, but not in HSPR negative cells.

The invention also encompasses nucleic acid molecules that encode the HSP receptor, and nucleic acid molecules hybridizable or complementary to the nucleic acid molecules. As used herein, the term hspr gene refers to any DNA sequence that encodes an HSPR or a fragment thereof; or any DNA sequence that hybridizes to the complement of the DNA sequences that encode an HSPR under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at page 2.10.3); or any DNA sequence that hybridizes to the complement of the DNA sequences that encode an HSPR under moderately stringent conditions, e.g., washing in 0.2×SSC/ 0.1% SDS at 42° C. (Ausubel et al., 1989, supra) and encodes a gene product functionally equivalent to a HSPR, i.e. the gene product can bind HSP. In various embodiments of the invention, HSPR gene may also encompass fragments and degenerate variants of the foregoing DNA sequences, including naturally occurring variants thereof. The HSPR gene fragment may be a complementary DNA (cDNA) molecule or a genomic DNA molecule that may comprise one or more intervening sequences or introns, as well as regulating regions located beyond the 5' and 3' ends of the coding region or within an intron.

hspr genes can be identified and isolated by various methods including but not limited to hybridization with a pool of nucleic acid probes having degenerate nucleotide sequences that encode a fragment of HSPR; differential expression; and expression cloning based on binding to HSP or an antibody to HSPR. Subtractive hybridization may be used to enrich for nucleic acid molecules encoding HSPR. Specific embodiments of such methods are detailed in the sections infra.

In a preferred embodiment, HSP receptor positive cells can be isolated first, and subsequently used to generate antibodies against HSPR. HSPR antibodies can then be used to isolate HSP receptor protein by methods well known in the art, such as affinity chromatography. HSPR antibodies can further be used to identify clones of hspr genes from cDNA expression libraries made from RNA of HSPR positive cells.

In another preferred embodiment, HSPR positive cells can be isolated and used to extract and purify mRNA. HSPR positive cell mRNA can then be used to construct a subtracted cDNA library that contains a large proportion of DNA copies of transcripts expressed in HSPR positive cells but not in HSPR-negative cells. Full length cDNA specific for HSPR can be isolated from this library and used to construct protein expression vectors by standard molecular cloning techniques. Recombinant protein can subsequently be purified and used to generate antibodies against HSPR protein. Such antibodies can be used to further identify, purify and isolate native HSP receptor protein and cells.

The experimental methods used to isolate the proteins, antibodies, cells and genes of the invention are fully described herein. The steps described above are given here for the purpose of description, and are not necessarily followed in the precise order given. In fact, different sequences of these steps can be used to isolate the HSPR protein, antibodies, and genes of the invention.

5.1 Purification of HSP Receptor Positive Cells

The present invention relates to cells that express the HSP receptor, herein termed HSPR positive cells. The HSPR positive cells of the invention can be isolated by physically separating cells that express the HSP receptor on their surfaces from a mixed population of cells. The HSPR positive cells may be isolated from a number of sources including, but not limited to, macrophages and/or dendritic cells obtained from mammalian blood or bone marrow, or the transgenic mouse line Immort-o-Mouse® (Charles River Laboratories, Inc.). HSPR positive cells may be separated based on their ability to bind either native or affinity-labeled HSPs, either alone or in non-covalent complexes with antigenic peptides. The procedures used to isolate and purify HSPR positive cells are described in detail herein.

HSP receptor positive cells can be isolated based on their ability to bind HSPs, and can thereby be separated from cells that lack HSP receptors. Such HSPR positive cells can be separated based on their association with HSPs that have been conjugated with an affinity compound, HSPs that comprises an affinity tag, or, native HSP.

HSP protein for the purpose of labelling can be obtained by recombinant expression systems, by purification from tissue or mammalian cell culture line, or by synthetic methods. The purification of HSPs and HSP complexes is described herein below.

5.2 Preparation of HSPs and HSP-peptide Complexes

Heat shock proteins, which are referred to interchangeably herein as stress proteins, useful in the treatment and prevention of cancer, can be selected from among any cellular protein that satisfies any one of the following criteria. It is a protein whose intracellular concentration increases when a cell is exposed to a stressful stimuli, it is capable of binding other proteins or peptides, and it is capable of releasing the bound proteins or peptides in the presence of adenosine triphosphate (ATP) or low pH; or it is a protein showing at least 35% homology with any cellular protein having any of the above properties. The Hsps in the complexes that can be prepared by the present invention include but are not limited to, Hsp70, Hsp90, gp96, protein disulfide isomerase alone or in combination. Preferably, the Hsps are human Hsps. Preferred complexes comprise human Hsp60, Hsp70, or Hsp90, protein disulfide isomerase, non-covalently bound to a human protein antigen. In a specific embodiment, the complex comprises an Hsp called gp96 which is present in the endoplasmic reticulum of eukaryotic cells and is related to the cytoplasmic Hsp90s.

Three major families of HSPs, namely Hsp60, Hsp70 and Hsp90, have been identified so far. In addition, protein disulfide isomerase (PDI), and other proteins in the endoplasmic reticulum that contain thioredoxin-like domain(s), such as but not limited to ERp72 and ERp61, are also encompassed. It is contemplated that HSP-peptide complexes comprising members of all of these families, including but not limited to PDI-peptide complexes, can be prepared by the practice of the instant invention.

It has been discovered that the Hsp60, Hsp70, Hsp90 and protein disulfide isomerase families are composed of proteins that are related to the stress proteins in sequence, for example, having greater than 35% amino acid identity, but whose expression levels are not altered by stress. Therefore it is contemplated that the definition of stress or heat shock protein, as used herein, embraces other proteins, muteins, analogs, and variants thereof having at least 35% to 55%, preferably 55% to 75%, and most preferably 75% to 85% amino acid identity with members of these families whose expression levels in a cell are enhanced in response to a stressful stimulus.

In one embodiment of the invention, the HSPs in the Hsp-peptide complexes prepared from cancer cDNA host cells are native to the host cells, i.e, the Hsps that are noncovalently associated with recombinant antigenic peptides of the cancer cells are naturally occurring in the host cells.

In another embodiment, the Hsp in the Hsp-peptide complex is a recombinant Hsp produced by cancer cDNA host cells that are genetically engineered to express the recombinant Hsp. Such recombinant Hsps are noncovalently associated with recombinant antigenic peptides in host cells to form Hsp-peptide complexes. Such recombinant Hsps may also be fused to a heterologous polypeptide, such as an immunoglobulin constant region, which can facilitate purification of the noncovalent complex. The genetically engineered host cells may contain one or more copies of a nucleic acid sequence comprising a sequence that encodes a Hsp, operably associated with regulatory region(s) that drive expression of the Hsp nucleic acid sequence in the host cell. Any nucleic acid sequence encoding a Hsp, including cDNA and genomic DNA, can be used. It is preferred that the recombinant Hsp produced in the host cell or library cell is of the same species as the intended recipient of the immunogenic composition. Recombinant human Hsp is most preferred.

5.2.1 Preparation and Purification of Hsp70-peptide Complexes

The purification of Hsp70-peptide complexes has been described previously, see, for example, Udono et al., 1993, J. Exp. Med. 178:1391–1396. The following procedure may be used, presented by way of example but not limitation, to purify HSP 70 complexes. Initially, tumor cells are suspended in 3 volumes of 1× Lysis buffer consisting of 5 mM sodium phosphate buffer, pH 7, 150 mM NaCl, 2 mM CaCl$_2$, 2 mM MgCl$_2$ and 1 mM phenyl methyl sulfonyl fluoride (PMSF). Then, the pellet is sonicated, on ice, until >99% cells are lysed as determined by microscopic examination. As an alternative to sonication, the cells may be lysed by mechanical shearing and in this approach the cells typically are resuspended in 30 mM sodium bicarbonate pH 7.5, 1 mM PMSP, incubated on ice for 20 minutes and then homogenized in a Dounce homogenizer until >95% cells are lysed.

Then the lysate is centrifuged at 1,000 g for 10 minutes to remove unbroken cells, nuclei and other cellular debris. The resulting supernatant is recentrifuged at 100,000 g for 90 minutes, the supernatant harvested and then mixed with Con A Sepharose equilibrated with phosphate buffered saline (PBS) containing 2 mM Ca$^{2+}$ and 2 mM Mg$^{2+}$. When the cells are lysed by mechanical shearing the supernatant is diluted with an equal volume of 2× lysis buffer prior to mixing with Con A Sepharose. The supernatant is then allowed to bind to the Con A Sepharose for 2–3 hours at 4° C. The material that fails to bind is harvested and dialyzed for 36 hours (three times, 100 volumes each time) against 10 mM Tris-Acetate pH 7.5, 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a Mono Q FPLC column equilibrated in 20 mM Tris-acetate pH 7.5, 2 mM NaCl, 0.1 mM EDTA and 15 mM 2-mercaptuethano). The column is then developed with a 20 mM to 500 mM NaCl gradient and then eluted fractions fractionated by sodium dodecyl sulfate-polyacrylamide gel electrophoresis (SDS-PAGE) and characterized by immunoblotting using an appropriate anti-Hsp70 antibody (such as from clone N27F3-4, from StressGen).

Fractions strongly immunoreactive with the anti-Hsp70 antibody are pooled and the Hsp70-peptide complexes precipitated with ammonium sulfate; specifically with a 50%–70% ammonium sulfate cut. The resulting precipitate is then harvested by centrifugation at 17,000 rpm (SS34 Sorvall rotor) and washed with 70% ammonium sulfate. The washed precipitate is then solubilized and any residual ammonium sulfate removed by gel filtration on a Sephadex$^R$ G25 column (Pharmacia). If necessary the Hsp70 preparation thus obtained can be repurified through the Mono Q FPLC Column as described above.

The Hsp70-peptide complex can be purified to apparent homogeneity using this method. Typically 1 mg of Hsp70-peptide complex can be purified from 1 g of cells/tissue.

An improved method for purification of Hsp70-peptide complexes comprises contacting cellular proteins with ADP or a nonhydrolyzable analog of ATP affixed to a solid substrate, such that Hsp70 in the lysate can bind to the ADP or nonhydrolyzable ATP analog, and eluting the bound Hsp70. A preferred method uses column chromatography with ADP affixed to a solid substratum (e.g., ADP-agarose). The resulting Hsp70 preparations are higher in purity and devoid of non-specifically bound peptides. The Hsp70 yields are also increased significantly by about more than 10 fold. Alternatively, chromatography with nonhydrolyzable analogs of ATP, instead of ADP, can be used for purification of Hsp70-peptide complexes. By way of example but not limitation, purification of Hsp70-peptide complexes by ADP-agarose chromatography can be carried out as follows:

Meth A sarcoma cells (500 million cells) are homogenized in hypotonic buffer and the lysate is centrifuged at 100,000 g for 90 minutes at 4° C. The supernatant is applied to an ADP-agarose column. The column is washed in buffer and is eluted with 5 column volumes of 3 mM ADP. The Hsp70-peptide complexes elute in fractions 2 through 10 of the total 15 fractions which elute. The eluted fractions are analyzed by SDS-PAGE. The Hsp70-peptide complexes can be purified to apparent homogeneity using this procedure.

5.2.2 Preparation and Purification of Hsp90-peptide Complexes

A procedure that can be used, presented by way of example and not limitation, is as follows:

Initially, tumor cells are suspended in 3 volumes of 1× Lysis buffer consisting of 5 mM sodium phosphate buffer (pH7), 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells may be lysed by mechanical shearing and in this approach the cells typically are resuspended in 30 mM sodium bicarbonate pH 7.5, 1 mM PMSF, incubated on ice for 20 minutes and then homogenized in a Dounce homogenizer until >95% cells are lysed.

Then the lysate is centrifuged at 1,000 g for 10 minutes to remove unbroken cells, nuclei and other cellular debris. The resulting supernatant is recentrifuged at 100,000 g for 90 minutes, the supernatant harvested and then mixed with Con A Sepharose equilibrated with PBS containing 2 mM $Ca^{2+}$ and 2 mM $Mg^{2+}$. When the cells are lysed by mechanical shearing the supernatant is diluted with an equal volume of 2× Lysis buffer prior to mixing with Con A Sepharose. The supernatant is then allowed to bind to the Con A Sepharose for 2–3 hours at 4° C. The material that fails to bind is harvested and dialyzed for 36 hours (three times, 100 volumes each time) against 20 mM Sodium phosphate pH 7.4, 1 mM EDTA, 250 mM NaCl, 1 mM PMSF. Then the dialyzate is centrifuged at 17,000 rpm (Sorvall SS34 rotor) for 20 minutes. Then the resulting supernatant is harvested and applied to a Mono Q FPLC column equilibrated with lysis buffer. The proteins are then eluted with a salt gradient of 200 mM to 600 mM NaCl.

The eluted fractions are fractionated by SDS-PAGE and fractions containing the Hsp90-peptide complexes identified by immunoblotting using an anti-Hsp90 antibody such as 3G3 (Affinity Bioreagents). Hsp90-peptide complexes can be purified to apparent homogeneity using this procedure. Typically, 150–200 µg of Hsp90-peptide complex can be purified from 1 g of cells/tissue.

5.2.3 Preparation and Purification of gp96-peptide Complexes

A procedure that can be used, presented by way of example and not limitation, is as follows:

A cell pellet is resuspended in 3 volumes of buffer consisting of 30 mM sodium bicarbonate buffer (pH 7.5) and 1 mM PMSF and the cells allowed to swell on ice 20 minutes. The cell pellet is then homogenized in a Dounce homogenizer (the appropriate clearance of the homogenizer will vary according to each cell type) on ice until >95% cells are lysed.

The lysate is centrifuged at 1,000 g for 10 minutes to remove unbroken cells, nuclei and other debris. The supernatant from this centrifugation step is then recentrifuged at 100,000 g for 90 minutes. The gp96-peptide complex can be purified either from the 100,000 pellet or from the supernatant.

When purified from the supernatant, the supernatant is diluted with equal volume of 2× lysis buffer and the supernatant mixed for 2–3 hours at 4° C. with Con A Sepharose equilibrated with PBS containing 2 mM $Ca^{2+}$ and 2 mM $Mg^{2+}$. Then, the slurry is packed into a column and washed with 1× lysis buffer until the $OD_{280}$ drops to baseline. Then, the column is washed with 1/3 column bed volume of 10% α-methyl mannoside (α-MM) dissolved in PBS containing 2 mM $Ca^{2+}$ and 2 mM $Mg^{2+}$, the column sealed with a piece of parafilm, and incubated at 37° C. for 15 minutes. Then the column is cooled to room temperature and the parafilm removed from the bottom of the column. Five column volumes of the α-MM buffer are applied to the column and the eluate analyzed by SDS-PAGE. Typically the resulting material is about 60–95% pure, however this depends upon the cell type and the tissue-to-lysis buffer ratio used. Then the sample is applied to a Mono Q FPLC column (Pharmacia) equilibrated with a buffer containing 5 mM sodium phosphate, pH 7. The proteins are then eluted from the column with a 0–1M NaCl gradient and the gp96 fraction elutes between 400 mM and 550 mM NaCl.

The procedure, however, may be modified by two additional steps, used either alone or in combination, to consistently produce apparently homogeneous gp96-peptide complexes. One optional step involves an ammonium sulfate precipitation prior to the Con A purification step and the other optional step involves DEAE-Sepharose purification after the Con A purification step but before the Mono Q FPLC step.

In the first optional step, described by way of example as follows, the supernatant resulting from the 100,000 g centrifugation step is brought to a final concentration of 50% ammonium sulfate by the addition of ammonium sulfate. The ammonium sulfate is added slowly while gently stirring the solution in a beaker placed in a tray of ice water. The solution is stirred from about ½ to 12 hours at 4° C. and the resulting solution centrifuged at 6,000 rpm (Sorvall SS34 rotor). The supernatant resulting from this step is removed, brought to 70% ammonium sulfate saturation by the addition of ammonium sulfate solution, and centrifuged at 6,000 rpm (Sorvall SS34 rotor). The resulting pellet from this step is harvested and suspended in PBS containing 70% ammonium sulfate in order to rinse the pellet. This mixture is centrifuged at 6,000 rpm (Sorvall SS34 rotor) and the pellet dissolved in PBS containing 2 mM $Ca^{2+}$ and $Mg^{2+}$. Undissolved material is removed by a brief centrifugation at 15,000 rpm (Sorvall SS34 rotor). Then, the solution is mixed with Con A Sepharose and the procedure followed as before.

In the second optional step, described by way of example as follows, the gp96 containing fractions eluted from the Con A column are pooled and the buffer exchanged for 5 mM sodium phosphate buffer, pH 7, 300 mM NaCl by dialysis, or preferably by buffer exchange on a Sephadex G25 column. After buffer exchange, the solution is mixed with DEAE-Sepharose previously equilibrated with 5 mM sodium phosphate buffer, Ph 7, 300 mM NaCl. The protein solution and the beads are mixed gently for 1 hour and poured into a column. Then, the column is washed with 5 mM sodium phosphate buffer, Ph 7, 300 mM NaCl, until the absorbance at 280 nm drops to baseline. Then, the bound protein is eluted from the column with five volumes of 5 mM sodium phosphate buffer, Ph 7, 700 mM NaCl. Protein containing fractions are pooled and diluted with 5 mM sodium phosphate buffer, Ph 7 in order to lower the salt concentration to 175 mM. The resulting material then is applied to the Mono Q FPLC column (Pharmacia) equilibrated with 5 mM sodium phosphate buffer, Ph 7 and the protein that binds to the Mono Q FPLC column (Pharmacia) is eluted as described before.

It is appreciated, however, that one skilled in the art may assess, by routine experimentation, the benefit of incorporating the second optional step into the purification protocol. In addition, it is appreciated also that the benefit of adding each of the optional steps will depend upon the source of the starting material.

When the gp96 fraction is isolated from the 100,000 g pellet, the pellet is suspended in 5 volumes of PBS containing either 1% sodium deoxycholate or 1% octyl glucopyranoside (but without the $Mg^{2+}$ and $Ca^{2+}$) and incubated on ice for 1 hour. The suspension is centrifuged at 20,000 g for 30 minutes and the resulting supernatant dialyzed against several changes of PBS (also without the $Mg^{2+}$ and $Ca^{2+}$) to remove the detergent. The dialysate is centrifuged at 100,000 g for 90 minutes, the supernatant harvested, and calcium and magnesium are added to the supernatant to give final concentrations of 2 mM, respectively. Then the sample is purified by either the unmodified or the modified method for isolating gp96-peptide complex from the 100,000 g supernatant, see above.

The gp96-peptide complexes can be purified to apparent homogeneity using this procedure. About 10–20 μg of gp96 can be isolated from 1 g cells/tissue.

5.2.4 Labelling of HSPs and HSP Peotide Complexes

HSP or HSP-peptide complexes can be labeled by conjugation of an affinity compound to HSP to facilitate detection and separation of HSPR cells. Affinity compounds that can be used include but are not limited to biotin, photobiotin, fluorescein isothiocyante (FITC), or phycoerythrin (PE), or other compounds known in the art. Cells retaining labeled HSP protein are then separated from cells that do not bind HSPs by techniques known in the art such as, but not limited to affinity chromatography and various cell sorting methods.

In one embodiment, affinity compounds or affinity tags can be conjugated to the HSP through a polyfunctional crosslinker, and preferably a bifunctional molecule. As used herein the term polyfunctional crosslinker encompasses molecules having more than one functional group that reacts with a functional group on the HSP. Typically, such crosslinker forms covalent bonds with an amino or sulfhydryl group on a polypeptide. For example, biotin N-hydroxysuccinimide esters may be used.

In another embodiment, HSP comprising a peptide tag, i.e., a fusion protein, may be used to facilitate identification and/or isolation of the HSPR. In various embodiments, such a fusion protein can be made by ligating a hsp gene sequence to the sequence encoding the peptide tag in the proper reading frame. A variety of peptide tags known in the art may be used in the modification of an HSP, such as but not limited to the immunoglobulin constant regions, polyhistidine sequence (Petty, 1996, Metal-chelate affinity chromatography, in Current Protocols in Molecular Biology, Vol. 2, Ed. Ausubel et al., Greene Publish. Assoc. & Wiley Interscience), glutathione S-transferase (GST; Smith, 1993, Methods Mol. Cell Bio. 4:220–229), the E. coli maltose binding protein (Guan et al., 1987, Gene 67:21–30), and various cellulose binding domains (U.S. Pat. Nos. 5,496,934; 5,202,247; 5,137,819; Tomme et al., 1994, Protein Eng. 7:117–123), etc. Other peptide tags may impart fluorescent properties to an HSP, e.g., portions of green fluorescent protein and the like. Other possible peptide tags are short amino acid sequences to which monoclonal antibodies are available, such as but not limited to the following well known examples, the FLAG epitope, the myc epitope at amino acids 408–439, the influenza virus hemagglutinin (HA) epitope. Other peptide tags are recognized by specific binding partners and thus facilitate isolation by affinity binding to the binding partner which can be immobilized onto a solid support.

As will be appreciated by those skilled in the art, many methods can be used to obtain the coding region of HSP gene sequences and the above-mentioned peptide tags, including but not limited to, DNA cloning, DNA amplification, and synthetic methods. The nucleotide sequences of non-limiting examples of HSP genes that can be modified and expressed by methods of the invention are published as follows: human gp96: Genebank Accession No. X15187; Maki et al., 1990, Proc. Natl. Acad Sci., 87: 5658–5562. mouse gp96: Genebank Accession No. M16370; Srivastava et al., 1987, Proc. Natl. Acad. Sci., 85:3807–3811; mouse BiP: Genebank Accession No. U16277; Haas et al., 1988, Proc. Natl. Acad. Sci. U.S.A., 85: 2250–2254, human BiP: Genebank Accession No. M19645; Ting et al., 1988, DNA 7: 275–286; mouse hsp70: Genebank Accession No. M35021, Hunt et al., 1990, Gene, 87:199–204, human hsp70, Genbank Accession No. M24743; Hunt et al., 1995, Proc. Natl. Acad. Sci. U.S.A., 82: 6455–6489. Due to the degeneracy of the genetic code, the term "hsp gene sequence" refers not only to the naturally occurring nucleotide sequence but also encompasses all the other degenerate DNA sequences that encode the hsp genes. Some of the peptide tags and reagents for their detection and isolation are available commercially.

5.2.5 Isolation of HSPR Positive Cells

The present invention provides methods for enriching and isolating cells that express heat shock protein receptors from a mixed population of cells.

In one embodiment, the present invention provides a method for isolating an HSPR positive cell comprising (a) incubating a solid phase containing HSP with a mixture of cells comprising HSPR positive cells, for a time period sufficient to allow binding of the HSPR positive cells to the solid phase; (b) removing the cells that are not bound to the solid phase; and (c) eluting the bound HSPR positive cells from the solid phase. This method can also be used with a HSP comprising an affinity tag such as those described in the previous section. Binding of the labeled HSP to the HSPR positive cells causes the HSPR positive cells to be labeled with the affinity tag which binds to a solid phase containing the binding partner of the affinity tag. The desired HSPR positive cells can be eluted from the solid phase after removing unbound cells. If the solid phase is a magnetic bead, HSPR positive cells bound to the bead can be separated from other cells by exposing the beads to a magnetic field.

Alternatively, a population of cells comprising HSPR positive cells can be incubated with fluorescently labeled HSP for a time period sufficient to allow binding of the labeled HSP to HSPR positive cells such that the HSPR positive cells are labeled fluorescently; and separating the HSPR positive cells that are fluorescently labeled from the unlabeled cells by fluorescence activated cell sorting.

Fluorescence activated cell sorting (FACS) is a well-known method for separating particles, including cells, based on the fluorescent properties of the particles (Kamarch, 1987, Methods Enzymol, 151:150–165). FACS works on the basis of laser excitation of fluorescent moieties in the individual particles. Positive fluorescence results in addition of a small electrical charge to the particle. The change allows electromagnetic separation of positive and negative particles from a mixture. Separated particles may be directly deposited into individual wells of 96-well or 384-well plates to facilitate separation and cloning.

Magnetic activated cell sorting (MACS) is a well-known method for separating particles based on their ability to bind magnetic beads (0.5–100 μm diameter) (Dynal, 1995). A variety of useful modifications can be performed on the magnetic microspheres, including covalent addition of antibody which specifically recognizes a cell-solid phase molecule or hapten, e.g., HSPR. The selected beads can be physically manipulated by exposure to a magnetic field. For example, the selected beads may be sequestered by application of a magnet to the outside of the reaction vessel.

For example, HSPs can be labeled by conjugating FITC to purified HSP. Fluorescently labeled HSP can be added to culture media containing purified macrophage or dendritic cells, and cells can be incubated for a period of time between 10 and 60 minutes, to allow binding to occur. Cells can then be processed through a cell sorter, allowing cells that bind HSP, HSPR positive cells, to be separated from those that do not bind HSP, HSPR-negative cells.

5.3 HSP Receptor Protein

The present invention further encompasses HSP receptor proteins and antibodies against such HSP receptor proteins. HSP receptor proteins can be purified from an extract prepared from HSP positive cells, and preferably from a fraction enriched for cell membrane components of the HSPR positive cells of the invention.

In one embodiment, a method of the invention for isolating a heat shock protein receptor comprises the steps of (a) preparing an extract of HSPR positive cells; (b) contacting a HSP with the extract for a time period sufficient for the HSPR in the extract to bind the HSP; and (c) recovering the bound HSPR from the HSP. The method can also be used with HSP that comprises an affinity tag wherein a further step of incubating the extract and the tagged HSP with a solid phase containing a binding partner of the affinity tag is involved.

In another embodiment, where an antibody to HSPR is available, the present invention provides a method for isolating a heat shock protein receptor comprising: (a) preparing an extract of HSPR positive cells; (b) contacting an antibody to HSPR with the extract for a time period sufficient for the HSPR in the extract to bind the antibody; and (c) recovering the bound HSPR from the antibody. Similarly, this method can be used with an antibody that comprises an affinity tag. Accordingly, the method further comprises incubating the extract and the tagged antibody to HSPR with a solid phase containing a binding partner of the affinity tag for a time period sufficient to allow binding of the HSPR to the solid phase prior to the recover step. The HSPR can then be eluted from the antibody.

The purified native HSP receptor, HSPR positive cells or cell membranes, or recombinant HSP receptor protein can be used to generate HSPR-specific antibodies. The detailed procedures for protein purification and antibody generation and purification are described herein.

5.3.1 Purification of HSP Receptor Protein

HSP receptor can be purified by isolating cell membranes and purifying the HSP receptor away from other membrane components. Membranes can be isolated from the HSPR positive cells of the invention, according to the methods described in Section 5.1, supra. Alternatively, such membranes can be isolated directly from a general population of macrophages, dendritic cells, or other cell type that expresses the HSP receptor.

Cells can be grown to an appropriate density and lysed. The plasma membrane fraction can be isolated from cells using procedures known in the art, such as dextran/polyethylene glycol biphase separation. Plasma membranes can be treated with a buffer which dissociates membrane-associated proteins from the lipid bilayer (e.g., a buffer containing a non-ionic detergent such as Nonidet P-40™, Triton X-100™, or sodium deoxycholate). Proteins can be purified away from membrane lipids using conventional dialysis procedures.

In one embodiment, the crude dialyzed protein preparation can be applied to an affinity column containing a given HSP, such as gp96, immobilized onto an appropriate solid phase. Membrane-associated proteins other than HSP receptor will pass through the column, while the HSP receptor will remain bound to the HSP. Non-specific binding of other membrane components-can be reduced by increasing the salt concentration and varying the Ph of the buffer in which the crude protein preparation is dissolved. Thorough washing of the column after application of the crude protein preparation can further reduce binding of non-specific proteins.

In another embodiment, HSPR protein may be purified using HSPR-specific antibodies, previously generated against recombinant HSPR protein, HSPR positive cells, or HSPR positive cell membranes (see Section 5.4 infra). The crude protein preparation is applied to an antibody affinity column which is composed of the HSP receptor-specific antibody immobilized on an appropriate solid phase. Antibody-coupled resin, or filter methods can also be used, or other antibody affinity techniques known in the art (see, for e.g., Harlow and Lane, Antibodies: A Laboratory Manual, Cold Spring Harbor Laboratory, 1988). The column or resin can be washed with buffer to remove proteins which bind non-specifically. The protein which remains bound to the column is eluted by conventional procedure such as washing with a buffer containing high salt or low Ph.

In yet another embodiment, HSPR protein may be further purified by sizing or ion exchange column chromatography. FPLC may be used to facilitate purification of large amounts of protein. If antibody is available, protein may be detected and followed during purification by Western blot or ELISA (enzyme-linked immunosorbent assay) analysis. If antibody is not available, the protein may be detected and followed using labelled-HSP binding assays.

In another embodiment, proteins produced by two cell populations may be compared such as the HSPR positive and HSPR negative cells of the invention. A membrane-bound protein present in HSPR positive cells but absent in HSPR negative cells can be identified and further characterized. methods for identifying differential protein expression, such proteins can be analyzed and separated by a variety of physico-chemical properties, such as molecular weight, shape, isoelectric print, charge, etc, which are well known in the art. In particular, as two-dimensional electrophoresis protein gels, are well known in the art (O'Farrell, 1975, J. Biol. Chem. 250:4007–21; Humphery-Smith et al., 1997, Electrophoresis 18:1217–1242).

In a preferred embodiment, HSPR positive and negative cells and cell membranes are prepared using a nonionic detergent. Proteins are then analyzed by two dimensional electrophoresis (2DE). For example, in the first dimension proteins are separated by surface charge isoelectric focusing gel electrophoresis (IEF), which separates proteins by surface charge. 400 $\mu$l proteins from HSPR positive and HSPR negative cells are electrophoresed on tube gels in 8M urea, 2% CHAPS, 10 mM DTT, 0.8% carrier ampholytes pH4–8, at constant temperature (10–15° C.) and high voltage (3500V) for approximately 24 hours. Proteins are separated along an electric field within a continuous Ph gradient until they arrive at their isoelectric point, at which point they are concentrated into narrow bands (O'Farrell, 1975, supra). Alternatively, non-equilibrium pH gradients (O'Farrell et al., 1977, Cell, 12: 1133–42) or immobilized pH gradients (IPG; Gorg, 1991, Nature 349:545–46) using pre-dried IPG strips (Pharmacia Biotech, Uppsala, Sweden) can be used in the first dimension. The gel strip is then equilibrated for a short time (20 mins) in 50 mM Tris-HCl pH6.8, 6M Urea, 25% glycerol, 0.2% SDS, 30 mM DTT, and loaded on the second dimension, sodium dodecyl sulphate-polyacrylamide gel electrophoresis (SDS-PAGE; Laemmli, Nature, 1970, 227: 680–85), which separates proteins by molecular weight. Proteins can be detected by a number of methods, including but not limited to: fluorescent dyes, silver staining, Coomassie Brilliant Blue R-250, Amido Black, Ponceau S, Fast Green, negative staining, and radioisotopes in association with liquid scintillation, autoradiography, fluorography and indirect autoradiography.

"Protein spots" that appear in samples from HSPR-positive membranes but are absent in samples from HSPR-negative membrane proteins can be analyzed further. Differences can be detected by visual inspection of gels, or by using densitometry and computerized image analysis thereby facilitating spot detection, background subtraction and spot matching (see Pennigton et al., 2997, Trends Cell viol. 7: 68–73). Further, HSPR protein can be detected by Western Blot analysis of 2D gels, if HSPR antibody is available (Harlow and Lane, supra). Once identified, the molecular weight ($M_r$) and the isoelectric point (pI) of an HSPR-positive cell specific protein can be determined by calibrating its position relative to known standards run in parallel on 2D gels. Specific proteins can then be purified, and their sequence determined by Edman degradation sequencing (Edman and Begg, 1967, Eur. J. Biochem. 1:80–91). automated by electroblotting onto polyvinylidene difluoride (PVDP) membranes using Edman degradation chemistry determined by gas-liquid phase, liquid-pulse or solid phase sequence analysis (Findlay and Geisow, 1989, Protein Sequencing; A Practical Approach, IRL Press, Oxford, pp. 1–199). Alternatively, proteins and peptides can be characterized by mass spectrometry, using peptide-mass fingerprinting or protein sequencing methodologies to identify sequence information and post-translational modifications (Dainese et al., 1997, Electrophoresis, 18:432–42; Mann and Wilm, 1995, Trends Diochem. Sci., 2:219–24; Yates, 1996, Methods Enzymol. 271:351–77). After limited sequence information is obtained, protein (Swiss-Prot) and nucleic acid sequence (Genebank and EMBL) databases can be searched to determine if protein sequence is novel. Novel proteins will be analyzed further in HSP binding assays, used to generate antibodies, as described in Section 5.4, and used for identification of HSPR nucleic acid sequences.

5.4 Generation of Antibodies Against the HSP Receptor

According to the invention, HSPR cells, cell membranes, native, synthetic, or recombinant protein, or fragments, derivatives, or analogs thereof, may be used as an immunogen to generate antibodies which immunospecifically bind an HSP receptor molecule. Such antibodies include but are not limited to polyclonal, monoclonal, chimeric, single chain, and Fab fragments.

Various procedures known in the art may be used for the production of polyclonal antibodies to an HSP receptor or derivative or analog (Harlow and Lane, supra). For example, in one embodiment rabbit polyclonal antibodies to an epitope of an HSPR, or a subfragment thereof, can be obtained. For the production of antibody, various host animals can be immunized by injection with the HSPR positive cells, HSPR positive cell membranes, native HSPR, recombinant HSPR, or a synthetic version, or derivative (e.g., fragment) thereof, including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

In one embodiment of the invention, HSPR positive cells or their plasma membranes can be used to generate antibody. HSPR cells or plasma membranes, as prepared in Sections 5.1 and 5.3, supra, are injected into rabbits. Such rabbits can be bled and serum collected and stored by methods well known in the art. In a preferred embodiment, to select HSP receptor specific antibodies, antiserum obtained from immunized animals can be mixed with HSPR negative whole cells (or plasma membranes, if plasma membranes originally used for injection; prepared as described in Section 5.3, supra) for 30 minutes at 4° C. to allow antibodies that are non-specific to HSPR to adsorb to HSPR negative cells. Cells can subsequently be centrifuged to pellet cells. The supernatant can be collected, re-mixed with HSPR negative cells or cell membranes. The procedure can be repeated several times to separate HSPR specific antibody. The purified antibody of this embodiment can then be used to purify HSPR protein and nucleic acids of the invention.

In another embodiment, antibodies to a HSP receptor protein, either native or recombinant, isolated according to the methods described in Sections 5.3.1 and 5.4, infra, are produced. In another embodiment, antibodies to a fragment or domain (e.g., the HSP binding domain; or transmembrane domain) of an HSP receptor are produced.

For preparation of monoclonal antibodies directed toward an HSPR or fragment thereof, any technique which provides for the production of antibody molecules by continuous cell lines in culture may be used. For example, the hybridoma technique developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96).

In one embodiment, mice or rats are hyper-immunized with macrophages or dendritic cells prepared as described in Section 5.1, infra, that fluoresce positive for HSP binding. Splenic lymphocytes are removed from the immunized animals and fused to myeloma cells by treatment with polyethylene glycol. Fused cells can be selected for by growing in HAT media, and single immortalized spleen cells which secrete antibody can be seeded into microtitre plates. The supernatant, containing antibody, can be collected from wells and tested for reactivity against HSPR positive cells. Wells containing positives are scored and the cells contained therein are isolated for continuous production of a monoclonal antibody.

In another specific embodiment, mice or rats are hyper-immunized with purified native protein, or a derivative or fragment thereof, isolated according to the methods described in Section 5.3.1, infra. In another embodiment purified recombinant protein, isolated according to the methods described in Section 5.6, supra, can be used. In another embodiment, a fragment, derivative, or a domain (e.g., the HSP binding domain) of an HSP receptor can be used to immunize mice or rats.

In an additional embodiment of the invention, monoclonal antibodies can be produced in germ-free animals utilizing methods known in the art e.g., as described in PCT/US90/ 02545. According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). Techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for an HSPR together with genes from a human antibody molecule of appropriate biological activity can also be used.

Techniques described for the production of single chain antibodies (U.S. Pat. No. 4,946,778) can also be adapted to produce HSPR-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for HSPRs, derivatives, or analogs.

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, the Fab fragments which can be generated by treating the antibody molecule with papain and a reducing agent, and Fv fragments.

In the production of antibodies, screening for the desired antibody can be accomplished by techniques known in the art, e.g. ELISA. For example, to select antibodies which recognize a specific domain of an HSPR, one may assay generated hybridomas for a product which binds to an HSPR fragment containing such domain. For selection of an antibody that specifically binds a first HSPR homolog but which does not specifically bind a different HSPR homolog, one can select on the basis of positive binding to the first HSP homolog and a lack of binding to the second HSP homolog.

The foregoing antibodies can be used in methods known in the art relating to the localization and activity of the HSP receptor sequences of the invention, e.g., for imaging these proteins, measuring levels thereof for use in therapeutic assays and physiological samples, in diagnostic methods, etc.

Accordingly, the present invention provides a method for preparing an antibody to a heat shock protein receptor comprising: (a) immunizing mice with HSPR or a fragment thereof; (b) obtaining serum from the immunized mice; (c) screening the serum for the ability to inhibit binding of HSP to HSPR positive cells; and (d) recovering the antibody from the serum with said ability.

Alternatively, a method for preparing an antibody to a heat shock protein receptor comprising the following steps can also be used: (a) immunizing mice with HSPR or a fragment thereof; (b) obtaining antibody-secreting cells from the immunized mice; (c) fusing the antibody-secreting cells with a murine myeloma to produce hybridomas secreting monoclonal antibodies; (d) screening the hybridomas for the ability of their secreted antibodies to inhibit binding of HSP to HSPR positive cells; and (e) recovering the antibody secreted by a hybridoma with said ability.

The present invention further provides a method for preparing an antibody to a heat shock protein receptor comprising: (a) immunizing mice with HSPR positive cells; (b) obtaining serum from the immunized mice; (c) screening the serum for the ability to inhibit binding of HSP to HSPR positive cells; and (d) recovering the antibody from the serum with said ability.

The present invention further provides a method for preparing an antibody to a heat shock protein receptor comprising: (a) immunizing mice with HSPR positive cells; (b) obtaining antibody-secreting cells from the immunized mice; (c) fusing the antibody-secreting cells with a murine myeloma to produce hybridomas secreting monoclonal antibodies; (d) screening the hybridomas for the ability of their secreted antibodies to inhibit binding of HSP to HSPR positive cells; and (e) recovering the antibody secreted by a hybridoma with said ability.

5.5 Isolation of HSP Receptor Gene Sequences

The HSP receptor gene sequences of the invention can be isolated directly from HSPR mRNA, cDNA or from a cDNA or genomic library. Alternatively, HSPR cDNA can be isolated by first isolating and characterizing the HSPR protein, and subsequently using the HSPR protein sequence to design nucleic acid probes for identifying HSPR gene sequences in a cDNA or genomic library. Details of such methods are fully described herein.

HSPR DNA sequences can be directly identified from HSPR mRNA, cDNA or from a cDNA library by using methods aimed at identifying genes that are expressed in HSPR positive cells but not in other cell types (such as HSPR negative cells). A number of methods exist for identifying such differentially expressed genes between two or more cell types. For example, differential display of cDNA 3' end sequences (Liang & Pardee, 1992, Science 257:967–971), serial analysis of gene expression by comparative gels of PCR products (SAGE; Velculescu et al., 1995, Science 270:484–487), or nucleic acid array (DNA chip) technology (Schena et al., 1995, Science 270:467–470; see also, J. Ramsey, 1998, Nat. Biotechnology 1:40–44), can be used to identify differentially expressed genes in a non-selective manner.

Alternatively, selective protocols can be used to specifically increase the abundance of sequences overexpressed in one population relative to another by elimination of gene products common for both from the two populations by means of subtractive-hybridization. A number of such subtraction hybridization protocols can be used, including, but not limited to, representational difference analysis (Fargnoli et al., 1990, Anal. Biochem., 187:364–73; Wang & Brown, 1991, Proc. Natl. Acad. Sci. 88:11505–09; see Lisitsyn, 1995, Trends Genet. 11:303–7), enzymatic degrading subtraction (EDS; Zeng et el., 1994, Nuc. Acid Res. 22:4381–85), RecA-mediated subtraction hybridization (Hakvoort et al., 1996, Nucl. Acids Res. 24:3478–80) or selective amplification via biotin and restriction mediated enrichment (SABRE; Lavery et al., 1997, Proc. Natl. Acad. Sci. USA 13:6831–36).

Each of the methods that examine differential gene expression listed above require the isolation and purification of mRNA from cells containing HSPR (such as the HSPR positive cells of the invention) and cells that lack HSPR (HSPR negative cells such as the HSPR negative cells of the invention) and synthesis of cDNA from such mRNA preparations.

Accordingly, in various embodiments of the invention, such as prior to examining differential gene expression or prior to making a gene library, it would be advantageous to select by subtractive hybridization for cDNA molecules that are expressed in HSPR positive cells but not in HSPR negative cells.

Most of the above methods further require the preparation of a cDNA library. The preparation of mRNA, cDNA, and cDNA libraries are specifically described herein.

5.5.1 Preparation of mRNA and cDNA

The purification of mRNA and the synthesis of complementary DNA (cDNA) from HSPR positive cell RNA, the procedures described in standard treatises, e.g., Methods in Enzymology, 1987, volume 154, Academic Press; Sambrook et al., 1989, Molecular Cloning—A Laboratory Manual, 2nd Edition, Cold Spring Harbor Press, New York; and Ausubel et al., Current Protocols in Molecular Biology, Greene Publishing Associates and Wiley Interscience, New York, may be followed to carry out routine molecular biology reactions in purification of mRNA. Methods described in detail infra are for illustration only and not by way of limitation. Various mRNA and cDNA preparation systems that are commercially available may also be used according to the manufacturer's instructions for making the mRNA and cDNA of the invention.

Total ribonucleic acid (RNA) may be isolated from HSPR positive and negative cells by a variety of methods known in the art depending on the source and amount of HSPR positive cells. It is preferable to obtain good quality RNA that is of high molecular weight in order to construct cDNA libraries that are contain even rarely expressed gene products. To prepare high quality RNA, methods that provide complete lysis of cells, and rapid inactivation of nucleases are preferred. A single-step RNA preparation method uses the strong chaotropic agent, guanidinium isothiocyanate, with a mild detergent and 2-mercaptoethanol or dithiothreitol to denature proteins and inactivate nucleases, followed by purification of the RNA by ultracentrifugation (Chomczynski & Sacchi, 1987, Anal Biochem 162:156–159; Chomczynski, 1989, U.S. Pat. No. 4,843,155) may also be used especially when isolating RNA from small quantities of cellular material.

Preferably, total RNA isolated from cells is further purified before conversion into complementary DNA (cDNA). Since the vast majority of eukaryotic messenger RNA (mRNA) molecules contain tracts of poly(adenylic) acid (poly-A) at the 3' end, it can be enriched by affinity chromatography using oligo-dT cellulose (Aviv & Leder, 1972, Proc. Natl. Acad. Sci., 69:1408–1412). Total RNA is denatured to expose the poly-A tails. Poly-A+ RNA is then bound to oligo-dT cellulose, with the remainder of the RNA washing through. The poly-A+ RNA is eluted by removing salt from the solution. This step may be repeated to further enrich for messenger RNA. A wide variety of oligo-dT matrices in different configurations may also be used, including but not limited to, simple gravity columns, paramagnetic particles, and spin columns. Substituted oligo-dT, such as biotinylated oligo-dT, may also be used. The quantity and quality of RNA thus obtained may be determined by methods such as formaldehyde agarose gel electrophoresis. The use of RNA enriched for poly-A+ RNA is most preferred.

Conversion of RNA into double-stranded cDNA can be accomplished by a number of different procedures well known in the art. See for example, Okayama & Berg, 1982, Mol. Cell Biol. 2:161–170; Gubler & Hoffman, 1983, Gene 25:263–269; and Huse & Hansen, 1988, Strategies (Stratagene) 1:1–3. The first step in the making of cDNA involves the oligonucleotide-primed synthesis of a first strand cDNA by reverse transcriptase. For example, mRNA hybridized to an oligo-dT primer can be copied into DNA by a reverse transcriptase, such as AMV reverse transcriptase, MMLV reverse transcriptase, or Superscript (Kotewicz et al., 1988, Nucleic Acid Res. 16:265–277). Random hexamers may be used to prime first-strand synthesis from internal sites within the mRNA instead of oligo-dT primers resulting in shorter cDNAs which are enriched for the 5' ends of long messenger RNAs.

The next step in the process involves synthesizing the second strand cDNA and producing suitable DNA ends for insertion in a cloning vector. Briefly, for example, the second strand cDNA may be synthesized using *E. coli* DNA polymerase I, Klenow fragment using the RNA-DNA as a template. The RNA in the RNA-DNA hybrid can be removed with RNase H, and gaps in the newly synthesized second strand cDNA can be filled in by *E. coli* DNA polymerase I. The fragments of second strand cDNAs thus produced are ligated with *E. coli* DNA ligase to form a contiguous second strand cDNA.

After second strand DNA synthesis, the double stranded cDNA requires further repair with enzymes, such as RNase H, RNase A, T4 DNA polymerase and *E. coli* DNA ligase, to form perfectly matched strands (i.e., having "flush" or "blunt" ends).

In some protocols, where the amount of starting cellular material is very limited, the cDNAs made from the HSPR positive or negative cells of the invention can be amplified in vitro, by nucleic acid amplification methods known in the art, such as polymerase chain reaction (PCR) and ligation chain reaction (LCR). Generally, first strand ligo-dT primed cDNA obtained by a standard method is extended with a oligo-dG tail by terminal transferase, and a second primer containing a oligo-dC segment is used to prime second strand synthesis with a thermostable DNA polymerase. This procedure produces a double-stranded cDNA population each molecule of which is bracketed by two oligonucleotides of known sequence. Using the appropriate set of primers, standard PCR can be used to amplify the cDNA. See, for example, U.S. Pat. Nos. 4,683,202, 4,683,195 and 4,889,818; Gyllenstein et al., 1988, Proc. Natl. Acad. Sci. USA 85:7652–7656; Ochman et al., 1988, Genetics 120:621–623; Loh et al., 1989, Science 243:217–220; Tam et al., 1989, Nucleic Acid Res. 17:1269; Belyavsky et al., 1989, Nucleic Acid Res. 17:2919–2932. In specific embodiments of the invention, RT-PCR can be used to generate amplified cDNAs from the RNAs (See, e.g., Domec et al., 1990, Anal Biochem, 188:422–426; Van Gelder et al., 1990, Proc. Natl. Acad. Sci., 87:1663–1667).

5.5.2 Identification of HSPR Gene Sequences by Differential Expression Methods

HSPR DNA sequences can be identified from HSPR positive cells by identifying genes that are expressed in HSPR positive cells but not in other cell types (such as HSPR negative cells). A number of methods exist for identifying such differentially expressed genes between two or more cell types. For example, differential display of cDNA 3' end sequences (Liang & Pardee, 1992, Science 257:967–971), serial analysis of gene expression by comparative gels of PCR products (SAGE; Velculescu et al., 1995, Science 270:484–487), or nucleic acid array (DNA chip) technology (Schena et al., 1995, Science 270:467–470; see also, J. Ramsey, 1998, Nat. Biotechnology 1:40–44), can be used to identify differentially expressed genes in a non-selective manner.

Differential display can be used identify HSPR cDNA sequences present in HSPR positive cells but absent in control cells, such as HSPR negative cells. HSPR positive cells and HSPR negative cells are prepared, as described in Section 5.1, supra. mRNA is isolated as described in Section 5.5.1, supra. cDNA is prepared from mRNA, as described, supra, using RT-polymerase chain amplification with a set of labelled oligonucleotide primers designed to identify the 3' ends of mRNAs (Liang & Pardee, 1992, supra). Primers used for the synthesis of the first strand each contains a stretch of oligo dT at its 5' end, followed by a pair of random nucleotides at its 3' end. Such oligonucleotides are end-labeled primers are used in reverse-transcriptase polymerase chain reactions to generate a population of specific cDNAs. Products of such RT-PCR reactions are digested with specific restriction endonucleases and displayed on a sequencing gel. Using mRNAs derived from different populations of cells, the pattern of displayed products can be compared to identify bands that are unique to different cell types (Liang and Pardee, 1995, Curr. Opin. Immunol., 7:274–280; McClelland, M. et al.(1995) Trends Genet., 11, 242–246).

In a preferred embodiment, mRNA from HSPR positive is compared to mRNA from HSPR negative cells by differential display. HSPR positive cells and HSPR negative cells are prepared as described in Section 5.1, supra. The preparation of mRNA is as described in Section 5.5.1. Following RT-PCR using the specific set of primers described hereinabove, RT-PCR products are displayed on thin poly-acrylamide gels containing 8% urea, the type used for DNA sequencing analysis. Products that are detected in HSPR positive cells but absent in HSPR negative control calls are chosen to be analyzed further. Gel purification and sequence analysis of such products can be performed to identify HSPR nucleic acid candidates. Protein-coding sequences of HSPR candidates, i.e., sequences present in HSPR positive cells but not in control cells, can be compared to known protein sequences in a data base such as Swiss-prot (Bairoch & Apweiler, 1998, Nucl. Acids Res. 26:38–42). Novel sequences can be chosen as potential HSPR candidates. Such gene products can then be isolated from the cDNA population using standard cloning techniques (Ausubel et al., 1992, supra), and can be tested for their ability to bind RSP ligand and antibodies.

In another embodiment, nucleic acid array technology can be used. In another embodiment, nucleic acid array technology can be used to identify HSPR positive cell specific sequences. Such micro-arrays of cDNA probes have been successfully used to compare the expression patterns of different cell types (DeRisi, et al., 1996, Nat.Genet., 14:457–460). Micro-arrays typically have many different DNA molecules fixed at defined "addresses" on a two dimensional, usually glass, support. Each address contains either many copies of a single DNA, or a mixture of different DNA molecules, and each DNA molecule is usually 1000 nucleotides or less in length. The DNAs can be from any source, cDNA libraries, or can be synthesized oligonucleotides. A vast excess of probe is fixed at each address, so that the hybridization signal intensity at that address is limited by the concentration of labeled complementary sequence in immediate proximity to the address. The probe array is useful for measuring the ratio of hybridization between to differently labeled samples that are thoroughly mixed and therefore share the same hybridization conditions. Simple probe arrays are currently able to detect cDNA species that are present at 2 to 10 copies of mRNA per cell when contacted with a solution containing a total cDNA concentration of 1 mg/ml. In a preferred embodiment, mRNA derived from RB-1 positive cells and HSPR negative cells is labelled with distinct fluorophores and hybridized to DNA on a micro-array in a mixture. The sequences of differentially expressed nucleic acids are determined by identifying the addresses where differential hybridization between the two cell populations occurs. These nucleic acid sequences can then be used to identify hspr gene sequences, to synthesize recombinant protein, and to generate antibodies.

5.5.3 Preparation of a cDNA Library

Described herein are methods for the construction and screening of a cDNA library. The insertion of cDNAs prepared in Section 5.5.1, supra, into an appropriate cloning vector, and the introduction of the cloned cDNAs into an appropriate host organism for propagation is described herein. Such cDNA libraries may then be used for preparation of "subtracted" cDNA libraries, or for direct and expression screening for HSPR gene sequences. Methods for such procedures are fully described herein.

The procedures described in standard treatises, e.g., Methods in Enzymology, 1987, volume 154, Academic Press; Sambrook et al., 1989, supra; and Ausubel et al., supra, may be followed to carry out routine molecular biology reactions used in constructing and producing the HSPR positive cell cDNA libraries. Methods described in detail infra are for illustration only and not by way of limitation. Various cDNA cloning systems that are commercially available may also be used according to the manufacturer's instructions for making an HSPR positive cell cDNA library of the invention.

RNA is purified from HSPR positive cells, or macrophage or dendritic cells as described in Section 5.5.1, supra. Conversion of RNA into double-stranded cDNA can be accomplished as described supra, by a number of different procedures well known in the art. See for example, Okayama & Berg, 1982, Mol. Cell Biol. 2:161–170; Gubler & Hoffman, 1983, Gene 25:263–269; and Huse & Hansen, 1988, Strategies (Stratagene) 1:1–3.

In order to attach DNA sequences with regulatory functions, such as promoters, to the double-stranded cDNAs, or to insert the double stranded cDNAs into the cloning site of a vector, linkers or adapters providing the appropriate compatible restriction sites may be ligated to the ends of the cDNAs by techniques well known in the art (Wu et al., 1987, Methods in Enzymol 152:343–349). Cleavage with a restriction enzyme can be followed by modification to create blunt ends by digesting back or filling in single-stranded DNA termini before ligation. Alternatively, a desired restriction enzyme site can be introduced into a cDNA by amplification of the cDNA by use of PCR with primers containing the desired restriction enzyme site. Homopolymeric tailing may also be used to generate the appropriate ends in the cDNAs for cloning (Eschenfeldt et al., 1987, Methods in Enzymol, 152:337–342).

Linkers are synthetic duplex molecules that are blunt at both ends. Prior to ligation of a linker to doublet-stranded cDNAs, in order to protect internal restriction sites of the cDNAs from cleavage by the restriction enzyme digestion (required to allow ligation of the vector and linker), the cDNAs are methylated with the appropriate DNA modification system associated with the given restriction enzyme. For example, double-stranded cDNA can be methylated by E. coli methylase, ligated to E. coli linkers, and digested with EcoRI to generate EcoRI sites at the ends of the cDNAs. The linkered cDNA can be inserted into a cloning vector with a EcoRI site directly.

Adapters are short partially duplex DNA molecules having a phosphorylated blunt end for ligation to the ends of the cDNAs, a double-stranded regions optionally containing one or more rare restriction sites, and a single stranded segment that forms a compatible ends ready for insertion into a cloning vector with a corresponding restriction site. In cases where an adaptor is used to modify the ends of the cDNAs, the methylation and restriction digestion steps described above can be bypassed.

Another well known strategy for generation of cDNAs that have unique ends for use in orientation-specific or directional cloning may also be used. This method uses a cloning vector with an appropriately positioned promoter to increase the likelihood of expressing the cloned cDNAs in the correct orientation by a factor of two.

Briefly, for example, directional cloning can be carried out by hybridizing mRNA to a linker-primer that has a poly-dT tract and internal methylation-sensitive restriction sites, such as XhoI. The linker-primer is extended using a reverse transcriptase and a nucleotide mix in which dCTP is replaced with methylated-dCTP. When second strand synthesis is completed, adapters containing a desired restriction site, such as EcoRI, can be ligated to the double-stranded cDNAs, which is then treated with XhoI. A XhoI site at the 3' end of the cDNAs is generated while the internal methylated XhoI sites remain uncut. Such cDNAs having a desired site, such as EcoRI, at the 5' end and an XhoI site at the 3' end can be cloned unidirectionally into a vector such that the 5' end of the cDNAs are consistently positioned downstream from a promoter.

Alternatively, an adapter-primer can be used which contains a poly-dT tract adjacent to a rare restriction site, such as NotI. Subsequent procedure is carried out as for oligo-dT primed synthesis using unsubstituted nucleotides as described above, except that the final cDNAs with adapters attached (such as EcoRI adapters) is digested with the rare restriction enzyme, resulting in cDNAs with a desired restriction site, such as EcoRI, at one end, and the rare restriction site at the other end. Such cDNAs having an EcoRI site at the 5' end and a rare restriction site, such as NotI, at the 3' end can be cloned unidirectionally into a vector containing a EcoRI/NotI cloning site wherein a promoter can be positioned upstream of the EcoRI cloning site.

Linkered or adapted cDNAs can be passed over a size exclusion column such as SEPHAROSE™ CL-4B to remove unligated linkers or adapters and other low molecular weight material that would interfere with the ensuing manipulations. Optionally, fractionation of the Tinkered or adapted cDNAs, for example, by agarose gel electrophoresis, can be carried out to enrich for cDNA of a particular size range.

The double stranded cDNAs can be ligated to DNA sequences with regulatory functions, and/or inserted into a cloning vector for propagation prior to expression in suitable host cells, or directly inserted into an expression vector or flanked by sequences promoting intrachromosomal insertion, for expression in suitable host cells.

5.5.4 Subtractive Hybridization Expression Methods

Selective protocols can be used to specifically increase the abundance of sequences overexpressed in one population relative to another by elimination of gene products common for both from the two populations by means of subtractive hybridization. A number of such subtraction hybridization protocols can be used, including, but not limited to, representational difference analysis (Fargnoli et al., 1990, Anal. Biochem., 187:364–73; Wang & Brown, 1991, Proc. Natl. Acad. Sci. 88:11505–09; see Lisitsyn, 1995, Trends Genet. 11:303–7), enzymatic degrading subtraction (EDS; Zeng et el., 1994, Nuc. Acid Res. 22:4381–85), RecA-mediated subtraction hybridization (Hakvoort et al., 1996, Nucl. Acids Res. 24:3478–80) or selective ampliation via biotin and restriction mediated enrichment (SABRE; Lavery et al., 1997, Proc. Natl. Acad. Sci. USA 13:6831–36).

In a preferred embodiment, a subtracted library is is prepared from HSPR positive cells and HSPR negative cells. The HSPR positive cells and HSPR negative cells are prepared as described in Section 5.1, supra. HSPR positive cell cDNA is hybridized to a large excess of poly A+ mRNA from HSPR negative cells. cDNA molecules expressed only in HSPR positive cells will not hybridize, and can be removed by passing mixture over a hydroxylapatite column under conditions such that the column specifically retains RNA:DNA duplexes but not DNA or DNA duplexes. The column flow-through, containing cDNAs representing mRNAs that are expressed in HSPR positive cells but not in HSPR negative cells, is cloned into an appropriate vector. The library thus created is plated out on Luria Broth to isolate singe colonies, transferred to nitrocellulose filters, and screened with a 32P-labeled cDNA probe HSPR positive cell cDNA subtracted with HSPR negative cell mRNA. The cDNA clones can be sequenced, and sequence of positive clones can be used to screen a genomic library and thus identify HSPR gene. The preparation of mRNA and cDNA are prepared as described hereinabove in Section 5.5.1, and cDNA libraries are prepared specifically described hereinbelow in Section 5.5.3.

5.5.5 Screeninq of Gene Library

The present invention provides various methods for isolation of nucleic acid molecules encoding HSPR by screening cDNA and/or genomic DNA library. A gene library comprises a pool of nucleic acid molecules, in which one or more nucleic acid molecules comprise nucleotide sequences encoding HSPR or a fragment thereof. A gene library can be introduced into the appropriate recombinant cells for replication and screening and for production of the proteins encoded by the cDNAs.

In one embodiment, the invention provides a method for screening a gene library for the HSPR gene using one or more nucleic acid probe, such as a pool of degenerate oligonucleotides having sequences that encode HSPR or a fragment thereof. The nucleic acid sequence of the probe can be designed in accordance to available peptide sequence of HSPR, a fragment or homolog thereof. For example, a probe based on the HSPR peptide sequence of one species can be used to identify and isolate the HSPR gene of a related species. HSPR can be purified and sequenced, as described in Section 5.3.1, supra. Protein sequence information is then used to design degenerate oligonucleotides containing all possible codons for HSPR amino acids. Sequence information from various regions of the protein can be used to generate a series of such degenerate pools of oligonucleotides. Thus, each oligonucleotide pool contains some sequences that are complementary in its entirety to HSPR gene sequences. Such degenerate oligonucleotide pools can be used to screen a gene library, prepared as described herein, supra. Accordingly, the method comprises (a) incubating a labeled nucleic acid probe with DNA molecules derived from recombinant cells containing a plurality of DNA molecules from HSPR positive cells, for a time period sufficient to allow hybridization of the labeled probe to the DNA molecules, wherein the labeled probe having a nucleic acid sequence that comprises a sequence that encodes HSPR or a fragment thereof; (b) identifying the recombinant cell containing the DNA molecule to which the labeled probe bound; (c) recovering the DNA molecule present in the recombinant cell.

In another embodiment, the invention provides methods for identifying and isolating the HSPR gene that rely on expression of cDNA insert and screening for its activity by binding assays, immunological methods, or an altered cellular phenotype. The HSPR cDNA can be isolated indirectly by screening the cDNA expression library for HSPR activity, such as HSP binding or HSPR antibody-binding activity. For example, HSP or HSPR antibodies can be labeled with a detectable compound, such as a radioactive, fluorescent or biotinylated compound, and used as probes to screen bacterial colonies that have been induced to express cDNA inserts. Accordingly, the invention provides a method for isolating a cDNA molecule encoding HSPR comprising:

(a) incubating recombinant cells expressing the proteins encoded by a plurality of cDNA molecules synthesized from HSPR positive cells on a solid phase with a labeled HSP, for a time period sufficient to allow binding of the labeled HSP to the recombinant cells; (b) removing the labeled HSP that are not bound to the recombinant cells; (c) eluting the recombinant cells to which the labeled HSP is bound from the solid phase; (d) recovering the cDNA molecule present in the recombinant cells. The method can further involve additional rounds of screening comprising (e) replicating the recovered cDNA molecules; (f) introducing the cDNA molecule into cells capable of expressing the proteins encoded by the cDNA molecule; and (g) repeating steps (a) through (d) wherein the recombinant cells are the cells of step (f), until one cDNA molecule is recovered from step (d).

HSP that comprises an affinity tag such as those described in Section 5.2.4, can be advantageously used to identify and isolate recombinant cells expressing HSPR cDNA from a gene library. Such a method comprises the steps of (a) incubating recombinant cells expressing the proteins encoded by a plurality of cDNA molecules synthesized from HSPR positive cells with a HSP comprising an affinity tag, for a time period sufficient to allow binding of the HSP to the recombinant cells such that the recombinant cells are labelled with the affinity tag; (b) incubating the recombinant cells with a solid phase containing a binding partner of the affinity tag, for a time period sufficient to allow binding of the labeled recombinant cells to the solid phase; (c) removing the recombinant cells that are not bound to the solid phase; (d) eluting the labeled recombinant cells from the solid phase; and (e) recovering the cDNA molecule present in the labeled recombinant cells.

Alternatively, an antibody to HSPR can be used to screen a cDNA gene library. This embodiment of the invention comprises (a) incubating recombinant cells expressing the proteins encoded by a plurality of cDNA molecules synthesized from HSPR positive cells on a solid phase with an antibody to HSPR, for a time period sufficient to allow binding of the antibody to HSPR to the recombinant cells; (b) removing the antibody to HSPR that are not bound to the recombinant cells; (c) eluting the recombinant cells to which the antibody to HSPR is bound from the solid phase; (d) recovering the cDNA molecule present in the recombinant cells. The method can further comprises (e) replicating the recovered cDNA molecules; (f) introducing the cDNA molecule into cells capable of expressing the proteins encoded by the cDNA molecule; and (g) repeating steps (a) through (d) wherein the recombinant cells are the cells of step (f), until one cDNA molecule is recovered from step (d).

A eukaryotic expression library can be screened by "panning" (Seed, 1987, Proc. Natl. Acad. Sci. USA 84:3365–69). This method is particularly preferred for screening cDNA molecules encoding proteins that are expressed on the cell surface. Using this technique, culture dishes are pre-coated with antibody, which can bind to cells that express HSPR. Alternatively, culture dishes may be coated with HSP protein, which also can bind to cells that express the HSP receptor. Non-adherent cells can be rinsed away, and selected cells can be isolated and their inserts can be further analysed.

Accordingly, the present invention provides a method for isolating a cDNA molecule encoding HSPR comprising (a) incubating a solid phase containing an antibody to HSP with recombinant cells expressing the proteins encoded by a plurality of cDNA molecules synthesized from HSPR positive cells, for a time period sufficient to allow binding of the recombinant cells to the solid phase; (b) removing the recombinant cells that are not bound to the solid phase; (c) eluting the bound recombinant cells from the solid phase; (d) recovering the cDNA molecule present in the recombinant cells. The method can further comprises (e) replicating the recovered cDNA molecules; (f) introducing the cDNA molecule into cells capable of expressing the proteins encoded by the cDNA molecule; and (g) repeating steps (a) through (d) wherein the recombinant cells are the cells of step (f), until one cDNA molecule is recovered from step (d). The invention also encompass the method for isolating a cDNA molecule encoding HSPR comprising: (a) incubating a solid phase containing HSP with recombinant cells expressing the proteins encoded by a plurality of cDNA molecules synthesized from HSPR positive cells, for a time period sufficient to allow binding of the recombinant cells to the solid phase;

(b) removing the recombinant cells that are not bound to the solid phase; (c) eluting the bound recombinant cells from the solid phase; and (d) recovering the cDNA molecule present in the recombinant cells. The method further comprises (e) replicating the recovered cDNA molecules; (f) introducing the cDNA molecule into cells capable of expressing the proteins encoded by the cDNA molecule; and (g) repeating steps (a) through (d) wherein the recombinant cells are the cells of step (f), until one cDNA molecule is recovered from step (d). The identity of the cDNA molecules can be ascertained by DNA sequencing.

In a specific embodiment, macrophage-derived or dendritic cell-derived cell line may be used. It is preferable that the type of host cell used in panning is non-adherent to surfaces of cell culture containers, such as plastic, so as to facilitate the screening methods of the invention. In one embodiment, an SV40 vector and control sequences are utilized, and the resulting cDNA library is introduced into African green monkey cells (COS cells). The cDNA library can be constructed in a vector containing viral control regions, and introduced in mammallian cells by tranfection or infection with viral vectors. Cells are distributed on microtiter dishes for screening. The cDNA library can be transiently expressed in mammalian cells. In a preferred embodiment, the cDNA used in constructing the library is prepared from mRNA isolated from the HSPR positive cells of the invention. In another embodiment, the library is a subtracted cDNA library, wherein gene products common to both HSPR positive cells and HSPR negative cells are eliminated from the HSPR positive cell mRNA or cDNA population by means of subtractive hybridization prior to construction of the cDNA library. In yet another embodiment, the library is a macrophage or dendritic cell cDNA library, or a "subtracted" macrophage or dendritic cell cDNA library, in which cDNAs common to both non-macrophage or dendritic cells are subtracted from the macrophage or dendritic cell cDNA population prior to cloning (Fargnoli et al., 1990, supra; Wang & Brown, 1991, supra; Lisitsyn, 1995, supra; Zeng et el., 1994, supra; Lavery et al., 1997, supra).

An expression construct, as used herein, refers to a polynucleotide comprising HSPR positive cell derived cDNA sequences operably associated with one or more regulatory regions which enables expression of the library of cDNAs in an appropriate host cell. "Operably-associated" refers to an association in which the regulatory regions and the cDNA sequence to be expressed are joined and positioned in such a way as to permit transcription, and ultimately, translation. The regulatory regions necessary for transcription of the cDNA library can be provided by an expression construct. A translation initiation codon (ATG) may also be provided if the cDNA fragments without their cognate initiation codon are to be expressed. In a compatible host-construct system, cellular transcriptional factors, such as RNA polymerase, will bind to the regulatory regions on the expression construct to effect transcription of the cDNA library in the host organism. The precise nature of the regulatory regions needed for gene expression may vary from host cell to host cell. Generally, a promoter is required which is capable of binding RNA polymerase and promoting the transcription of an operably-associated nucleic acid sequence. Such regulatory regions may include those 5'-non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites. In order to be "operably-associated", it is not necessary that the regulatory region and the cDNA sequences be immediately adjacent to one another. Regulatory regions suitable for gene expression are well known in the art (see Section 5.6). Both constitutive and inducible regulatory regions may be used for cDNA expression. It may be desirable to use inducible promoters when the conditions optimal for growth of the host cells and the conditions for high level expression of the cDNA library are different. This use of an inducible regulatory region may be particularly desirable if some of the proteins encoded by the cDNAs confer growth advantages or disadvantage to the recombinant host cells expressing them. Examples of useful regulatory regions are provided in the next section below.

The expression constructs comprising the cDNA library operably associated with regulatory regions can be directly introduced into appropriate host cells. See, for example, U.S. Pat. No. 5,580,859. The expression constructs can also comprise at both ends specific oligonucleotide sequences, which may be utilized as primers to amplify the cDNAs by polymerase chain reaction (PCR). The design of the primer sequences for DNA amplification and the ligation of the primer sequences to the cDNAs can be carried out by any methods known in the art, including those described above employing linkers and adaptors. The amplification can be carried out, e.g., by use of a Perkin-Elmer Cetus thermal cycler and Taq polymerase (Gene Amp™). Such a library of cDNA expression constructs can be amplified and maintained in vitro, without the use of DNA sequences that propagate the polynucleotide within living cells. Depending on needs, an aliquot of the cDNA expression library can be thawed and introduced directly into host cells. Such expression constructs can be used for expression of cancer cDNAs transiently in recombinant host cells.

Described herein are systems of vectors and host cells that can be used for cloning and expression of a cDNA library. An expression vector is a cloning vector that can be used for maintenance and expression of cDNA library in an appropriate host cell. Any cloning vector known in the art can be used to propagate the cDNA library. A variety of cloning vectors may be used in the present invention which include, but are not limited to, plasmids, cosmids, phage, phagemids, or modified viruses. Typically, such cloning vectors comprise a functional origin of replication for propagation of the vector in an appropriate host cell, one or more restriction endonuclease sites for insertion of the cDNA library, and one or more selection markers. The cloning vector must be used with a compatible host cell which may be derived from a prokaryotic or an eukaryotic organism including but not limited to bacteria, yeasts, insects, mammals, and humans.

Expression constructs and vectors are introduced into host cells for the purpose of expressing the cDNA library. Host cells broadly encompass cells of unicellular organisms, such as bacteria, fungi, and yeast, and of multicellular organisms, such as insects and animals including but not limited to birds, mammals and humans. Host cells may be obtained from private laboratory deposits, public culture collections such as the American Type Culture Collection, or from commercial suppliers.

5.5.6 cDNA Expression Cloning in Eukaryotic Cells cDNA expression cloning in a eukaryotic host is advantageous because the HSP surface receptor can be post-translationally modified and correctly inserted into the plasma membrane. Such modifications (e.g., glycosylation) and processing (e.g., cleavage) of cDNA-encoded proteins may enhance HSPR activity. Different host cells have characteristic and specific mechanisms for the post-translational processing and modification of proteins. A eukaryotic host-vector system is preferred, a mammalian host-vector system is more preferred, and a human host-vector system is the most preferred. Preferred mammalian host cells include but are not limited to those derived from humans, monkeys and rodents, such as chinese hamster ovary (CHO) cells, NIH/3T3, COS, HeLa, Daudi, 293, 293-EBNA, VERO, etc. (see, for example, Kriegler M. in "Gene Transfer and Expression: A Laboratory Manual", New York, Freeman & Co. 1990).

Any of the cloning and expression vectors described herein may be synthesized and assembled from known DNA sequences by well known techniques in the art. The regulatory regions and enhancer elements can be of a variety of origins, both natural and synthetic. Some vectors and host cells may be obtained commercially. Non-limiting examples of useful vectors are CDM8, λDR2 (see Appendix 5 of Current Protocols in Molecular Biology, 1988, Ed. Ausubel et al., Greene Publish. Assoc. & Wiley Interscience, which is incorporated herein by reference). By way of example, an exemplary expression host-vector system is λDR2 which is a lambda bacteriophage-based cloning vector coupled with a mammalian expression plasmid. Advantages of this system include the utilization of highly efficient lambda in vitro packaging systems for initially generating a library in E. coli hosts. Size selection may not be required since the packaging system only accepts inserts in a certain size range. Lambda vectors generally provide greater ease in amplification and storage. The initial library in E. coli may be amplified to produce, supercoiled plasmid DNA which may be used in high efficiency transformation methods for introduction into other expression host organisms. For example, λDR2 uses the lox P mediated site-specific recombination to excise the expression vector pDR2 containing a cDNA insert from lambda clones which can recircularize to generate a plasmid. The plasmid pDR2 contains eukaryotic regulatory regions based on the Epstein-Barr virus and selection markers that allows direct introduction of the cDNA inserts as a library into permissive human host cells at high efficiency.

For expression of cDNAs in mammalian host cells, a variety of regulatory regions can be used, for example, the SV40 early and late promoters, the cytomegalovirus (CMV) immediate early promoter, and the Rous sarcoma virus long terminal repeat (RSV-LTR) promoter. Inducible promoters that may be useful in mammalian cells include but are not limited to those associated with the metallothionein II gene, mouse mammary tumor virus glucocorticoid responsive long terminal repeats (MMTV-LTR), β-interferon gene, and Hsp70 gene (Williams et al., 1989, Cancer Res. 49:2735–42; Taylor et al., 1990, Mol. Cell Biol., 10:165–75). It may be advantageous to use heat shock promoters or stress promoters to drive expression of the cDNA in recombinant host cells. The efficiency of cDNA expression in a host cell may be enhanced by the inclusion of appropriate transcription enhancer elements in the expression vector, such as those found in SV40 virus, Hepatitis B virus, cytomegalovirus, immunoglobulin genes, metallothionein, β-actin (see Bittner et al., 1987, Methods in Enzymol. 153:516–544; Gorman, 1990, Curr. Op. in Biotechnol. 1:36–47).

In addition, the expression vector may contain selectable or screenable marker genes for initially isolating, identifying or tracking host cells that contain HSPR cDNA. A number of selection systems may be used for mammalian cells, including but not limited to the Herpes simplex virus thymidine kinase (Wigler et al., 1977, Cell 11:223), hypoxanthine-guanine phosphoribosyltransferase (Szybalski and Szybalski, 1962, Proc. Natl. Acad. Sci. USA 48:2026), and adenine phosphoribosyltransferase (Lowy et al., 1980, Cell 22:817) genes can be employed in tk⁻, hgprt⁻ or aprt⁻ cells, respectively. Also, antimetabolite resistance can be used as the basis of selection for dihydrofolate reductase (dhfr), which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neomycin phosphotransferase (neo), which confers resistance to the aminoglycoside G-418 (Colberre-Garapin et al., 1981, J. Mol. Biol. 150:1); and hygromycin phosphotransferase (hyg), which confers resistance to hygromycin (Santerre et al., 1984, Gene 30:147). Other selectable markers, such as but not limited to histidinol and Zeocin™ can also be used.

A number of viral-based expression systems may also be utilized with mammalian cells to make the cDNA libraries. Vectors using DNA virus backbones have been derived from simian virus 40 (SV40) (Hamer et al., 1979, Cell 17:725), adenovirus (van Doren et al., 1984, Mol Cell Biol 4:1653), adeno-associated virus (McLaughlin et al., 1988, J Virol 62:1963), and bovine papillomas virus (Zinn et al., 1982, Proc Natl Acad Sci 79:4897). In cases where an adenovirus is used as an expression vector, the donor DNA sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing heterologous products in infected hosts. (See e.g., Logan and Shenk, 1984, Proc. Natl. Acad. Sci. (USA) 81:3655–3659). Alternatively, the vaccinia 7.5 K promoter may be used. (See, e.g., Mackett et al., 1982, Proc. Natl. Acad. Sci. (USA) 79:7415–7419; Mackett et al., 1984, J. Virol. 49:857–864; Panicali et al., 1982, Proc. Natl. Acad. Sci. 79:4927–4931.) In cases where a human host cell is used, vectors based on the Epstein-Barr virus (EBV) origin (OriP) and EBV nuclear antigen 1 (EBNA-1; a trans-acting replication factor) can be used. Such vectors can be used with a broad range of human host cells, e.g., EBO-pCD (Spickofsky et al., 1990, DNA Prot Eng Tech 2:14–18); pDR2 and λDR2 (available from Clontech Laboratories). The expression vector pDR2 carries the EBV origin which confers stable episomal maintenance to the vector when activated by EBNA-1. Extremely high transfection efficiencies up to $10^{-1}$ can be obtained when pDR2 is transfected into cell lines which express EBNA-1. Host cells can be rendered proficient for high-efficiency transfections by first transfecting the host cells with an expression construct that produces EBNA-1.

cDNA libraries may also be made with a retrovirus-based expression cloning system. Retroviruses, such as Moloney murine leukemia virus, can be used since most of the viral gene sequence can be removed and replaced with the cDNA library while the missing viral functions can be supplied in trans. In contrast to transfection, retroviruses can efficiently infect and transfer genes to a wide range of cell types including, for example, primary hematopoietic cells. Moreover, the host range for infection by a retroviral vector can be manipulated by the choice of envelope used for vector packaging.

For example, a retroviral vector can comprise a 5' long terminal repeat (LTR), a 3' LTR, a packaging signal, a bacterial origin of replication, and a selectable marker. The cDNA is inserted into a position between the 5' LTR and 3' LTR, such that transcription from the 5' LTR promoter transcribes the cloned cDNA. The 5' LTR comprises a promoter, including but not limited to an LTR promoter, an R region, a U5 region and a primer binding site, in that order. Nucleotide sequences of these LTR elements are well known in the art. A heterologous promoter as well as multiple drug selection markers may also be included in the expression vector to facilitate selection of infected cells. See, McLauchlin et al., 1990, Prog Nucleic Acid Res and Molec Biol 38:91–135; Morgenstern et al., 1990, Nucleic Acid Res 18:3587–3596; Choulika et al., 1996, J Virol 70:1792–1798. Other useful eukaryotic host-vector system may include yeast and insect systems. In yeast, a number of vectors containing constitutive or inducible promoters may be used with *Saccharomyces cerevisiae* (baker's yeast), *Schizosaccharomyces pombe* (fission yeast), *Pichia pastoris*, and *Hansenula polymorph* (methylotropic yeasts). For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II.

In an insect system, Autographa californica nuclear polyhidrosis virus (AcNPV) a baculovirus, can be used as a vector to express cDNA in *Spodoptera frugiperda* cells. The cDNA sequences may be cloned into non-essential regions (for example the polyhedrin gene) of the virus and placed under control of an AcNPV promoter (for example the polyhedrin promoter). These recombinant viruses are then used to infect host cells in which the inserted DNA is expressed. (See e.g., Smith et al., 1983, J Virol 46:584; Smith, U.S. Pat. No. 4,215,051.)

The recombinant host cells may be cultured under standard conditions of temperature, incubation time, optical density, and media composition.

Expression constructs containing cloned cDNA can be introduced into the host cell by a variety of techniques known in the art, including but not limited to, for prokaryotic cells, λ-phage packaging and infection, bacterial transformation (Hanahan, 1985, in DNA Cloning, A Practical Approach, 1:109–136), and for eukaryotic cells, calcium phosphate mediated transfection (Wigler et al., 1977, Cell 11:223–232), liposome-mediated transfection (Schaefer-Ridder et al., 1982, Science 215:166–168), electroporation (Wolff et al., 1987, Proc Natl Acad Sci 84:3344), and microinjection (Cappechi, 1980, Cell 22:479–488).

5.5.7 cDNA Expression and Screening in Prokaryotic Cells

For cDNA expression in prokaryotic cells, cDNA can be cloned into a plasmid or phage vector. Vectors based on *E. coli* are the most popular and versatile systems for high level expression of foreign proteins (Makrides, 1996, Microbiol Rev, 60:512–538). Non-limiting examples of regulatory regions that can be used for expression in *E. coli* may include but not limited to lac, trp, lpp, phoA, recA, tac, T3, T7 and λ$P_L$ (Makrides, 1996, Microbiol Rev, 60:512–538). Non-limiting examples of prokaryotic expression vectors may include the λgt vector series such as λgt11 (Huynh et al., 1984 in "DNA Cloning Techniques", Vol. I: A Practical Approach (D. Glover, ed.), pp. 49–78, IRL Press, Oxford), and the pET vector series (Studier et al., 1990, Methods Enzymol, 185:60–89). λgt11 is particularly advantageous for this purpose. The phage contains the temperature sensitive repressor λcI857 which is inactive at 42 C. and the expression of the cDNA insert is under the control of the lac operon (Young and Davis, 1983, Science 222:778–782). Proteins may be induced by shifting temperature to 42° C. In this way, the expression of foreign proteins which are potentially deleterious or lethal to cell growth can be tightly controlled while bacterial colonies are growing at 37° C. Furthermore, in this system, cloning of cDNA insert interupts the β-galactosidase gene, so that recombinants are readily identified by addition of the gratuitous lac operon inducer isopropyl thio-β-D-galactopyranoside (IPTG) and assaying for β-galactosidase activity by methods well known in the art, such as plating on X-gal.

Expression constructs containing cloned cDNA can be introduced into the prokaryotic host cell by a variety of techniques known in the art, including but not limited to, λ-phage packaging and infection, transduction and transformation (Hanahan, 1985, in DNA Cloning, A Practical Approach, 1:109–136). Bacteria is infected with phage or transformed with plasmid carrying the cDNA library, plated on LB agar plates, and induced to express cDNA inserts.

However, a potential drawback of a prokaryotic host-vector system is the inability to perform many of the post-translational processing, folding and insertion into membranes normally required of cell surface receptors.

A specific cDNA insert can be detected and isolated by inducing expression of the cDNA inserts and utilizing screening methods that rely on detection of protein activity. Such methods include filter binding to a labelled ligand or immunological methods to detect antibody binding. Such methods are well known to those of skill in the art (See Ausobel, supra).

For example, in a preferred embodiment, HSPR can be isolated by screening the cDNA expression library for HSPR activity, such as HSP-ligand binding or HSPR antibody-binding activity. For example, HSP or HSPR antibodies can be labeled with a detectable compound, such as a radioactive, fluorescent or biotinylated compound, prepared as described in Section 5.2.4, supra, can be used as probes to screen induced proteins colonies attached to filters. HSPR or HSP antibody mixture is incubated using conditions that promote binding and developed as described above to detect HSPR clones. Alternatively, immunological methods are used to detect antibody.

5.5.8 cDNA Expression and Screening Using Xenopus Oocytes

A cDNA library can also be screened for HSPR expression in frog oocytes. Frog oocytes are advantageous for this purpose because their large size and (1–1.2 mm) and their abundance of protein translation machinery. In addition, insertion of receptor proteins can be inserted into membranes readily screened for activity. A cDNA library is constructed in a vector containing T3, T7, SP6 or other RNA polymerase promoter located on either side of a polylinker containing cloning sites for insertion of cDNA. cDNAs, prepared as described above in Section 5.5.3, are inserted into the vector, the library is amplified, and plasmid DNA is isolated and linearized by cutting with a restriction endonuclease whose site is in the polylinker. Run-off in transcriptions are performed in vitro, by addition of nucleotides and the appropriate polymerase, and mRNAs are injected into oocytes. After allowing for translation, oocytes are incubated with HSP and/or antibody to HSPR ligand labelled with radioactive, flourecsent, or otherwise detectable compound. Sublibraries displaying a positive signal are further divided, plasmid DNA is isolated, in vitro transcribed and injected until a single clone is isolated.

Any of the above described methods can be used to identify HSPR gene candidates. Positive clones can be isolated, purified and the sequence of their inserts can be determined. Such purified inserts can be used for the isolation of full length and genomic sequences, and for the expression of HSPR proteins as described below.

5.6 Expression of HSPR Genes

The nucleotide sequence coding for an HSPR protein or a functionally active analog or fragment or other derivative thereof (see Section 5.5), can be inserted into an appropriate expression vector, i.e., a vector which contains the necessary elements for the transcription and translation of the inserted protein-coding sequence. The necessary transcriptional and translational signals can also be supplied by the native HSPR gene and/or its flanking regions. A variety of host-vector systems can be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements can be used. In yet another embodiment, a fragment of an HSPR protein comprising one or more domains of the HSPR protein is expressed.

Any of the methods previously described for the insertion of DNA fragments into a vector can be used to construct expression vectors containing a chimeric gene consisting of appropriate transcriptional/translational control signals and the protein coding sequences. These methods can include in vitro recombinant DNA and synthetic techniques and in vivo recombinants (genetic recombination). Expression of a nucleic acid sequence encoding an HSPR protein or peptide fragment can be regulated by a second nucleic acid sequence so that the HSPR protein or peptide is expressed in a host transformed with the recombinant DNA molecule. For example, expression of an HSPR protein can be controlled by any promoter/enhancer element known in the art. Promoters which can be used to control HSPR gene expression include, but are not limited to, the SV40 early promoter region (Benoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic promoters such as the β-lactamase promoter (Villa-Kamaroff et al., 1978, Proc. Natl. Acad. Sci. U.S.A. 75:3727–3731), or the lac promoter (DeBoer et al., 1983, Proc. Natl. Acad. Sci. U.S.A. 80:21–25); see also "Strategies for Achieving High Level Expression of Genes in *Escherichia coli*" in Microbiological Reviews, 1996, 60:514; plant expression vectors comprising the nopaline synthetase promoter region (Herrera-Estrella et al., Nature 303:209–213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); a gene control region which is active in pancreatic beta cells (Hanahan, 1985, Nature 315:115–122), an immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; α1-antitrypsin gene control region which is active in the liver (Kelsey et al., 1987, Genes and Devel. 1:161–171), β-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Many of the vecto and prokamyotic/eukanyotic host cell systems described supra for construcing gene expression libraries can be used for expression of the HSPR protein.

In a specific embodiment, a vector is used that comprises a promoter operably linked to an HSPR gene nucleic acid, one or more origins of replication, and, optionally, one or more selectable markers (e.g., an antibiotic resistance gene).

In a specific embodiment, an expression construct is made by subcloning an HSPR coding sequence into the EcoRI restriction site of each of the three pGEX vectors (Glutathione S-Transferase expression vectors; Smith and Johnson, 1988, Gene 7:31–40). This allows for the expression of the HSPR protein product from the subclone in the correct reading frame.

Expression vectors containing HSPR gene inserts can be identified by three general approaches: (a) nucleic acid hybridization; (b) presence or absence of "marker" gene functions; and (c) expression of inserted sequences. In the first approach, the presence of an HSPR gene inserted in an expression vector can be detected by nucleic acid hybridization using probes comprising sequences that are homologous to an inserted HSPR gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of an HSPR gene in the vector. For example, if the HSPR gene is inserted within the marker gene sequence of the vector, recombinants containing the HSPR insert can be identified by the absence of the marker gene function. In the third approach, recombinant expression vectors can be identified by assaying the HSPR product expressed by the recombinant. Such assays can be based, for example, on the physical or functional properties of the HSPR protein in in vitro assay systems, e.g., binding with anti-HSPR protein antibody or HSP.

Once a particular recombinant DNA molecule is identified and isolated, several methods known in the art can be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda phage), and plasmid and cosmid DNA vectors, to name but a few.

In addition, a host cell strain can be chosen which modulates the expression of the inserted sequences, or modifies and processes the gene product in the specific fashion desired. Expression from certain promoters can be elevated in the presence of certain inducers; thus, expression of the genetically engineered HSPR protein can be controlled. Furthermore, different host cells have characteristic and specific mechanisms for the translational and post-translational processing and modification (e.g., glycosylation, phosphorylation of proteins. Appropriate cell lines or host systems can be chosen to ensure the desired modification and processing of the foreign protein expressed. For example, expression in a bacterial system can be used to produce a non-glycosylated core protein product. Expression in yeast will produce a glycosylated product. Expression in mammalian cells can be used to ensure "native" glycosylation of a heterologous protein. Furthermore, different vector/host expression systems can effect processing reactions to different extents.

In other specific embodiments, the HSPR protein, fragment, analog, or derivative can be expressed as a fusion, or chimeric protein product (comprising the protein, fragment, analog, or derivative joined via a peptide bond to a heterologous protein sequence of a different protein). Such a chimeric product can be made by ligating the appropriate nucleic acid sequences encoding the desired amino acid sequences to each other by methods known in the art, in the proper coding frame, and expressing the chimeric product by methods commonly known in the art. Affinity tags previously described for modifying HSPs can also be used to modifying HSPs can also be used to modify HSPR so as to create HSPR that can be easily purified, immobilized or detected. Alternatively, such a chimeric product can be made by protein synthetic techniques, e.g., by use of a peptide synthesizer. PCR amplification (particularly if some protein sequence is available).

5.7 Assays for the Identification of Compounds that Modulate the Activity of the HSP Receptor The present invention relates to in vitro and in vivo assay systems, described in the subsections below, which can be used to identify compounds or compositions that modulate the activity of the HSP receptor and its interaction with HSPs, HSP-peptide complexes, or HSPR antibody. The invention provides screening methodologies useful in the identification of proteins and other compounds which bind to, or otherwise directly interact with, the the HSP receptor genes and their gene products. Such compounds may bind the HSP receptor genes or gene products with differing affinities, and may serve as powerful regulators of receptor activity in vivo with useful therapeutic applications in modulating the immune response. For example, certain compounds that inhibit receptor function may be used in patients to downregulate destructive immune responses which are caused by cellular release of heat shock proteins. In other situations, compounds can be used to enhance receptor expression on cell surfaces and thus upregulate immune responses for destroying cancer or pathogen-infected cells.

Methods to screen potential agents for their ability to modulate HSPR expression and activity can be designed based on the inventor's discovery of the HSP receptor and its role in HSP or HSP-peptide complex binding and recognition. The HSP receptor protein, nucleic acids, and derivatives can be used in screening assays to detect molecules that specifically bind to HSPR proteins, derivatives, or nucleic acids, and thus have potential use as agonists or antagonists of the HSP receptor, to modulate the immune response. In a preferred embodiment, such assays are performed to screen for molecules with potential utility as anti-cancer and anti-viral drugs or lead compounds for drug development. For example, recombinant cells expressing HSPR nucleic acids can be used to recombinantly produce HSPR in these assays, to screen for molecules that bind to the HSP receptor protein. Similar methods can be used to screen for molecules that bind to the HSP receptor derivatives or nucleic acids. Methods that can be used to carry out the foregoing are commonly known in the art.

The assays of the present invention may be first optimized on a small scale (i.e., in test tubes), and then scaled up for high-throughput assays. The screening assays of the present may be performed in vitro, i.e. in test tubes, using purified components or cell lysates. The screening assays of the present invention may also be carried out in intact cells in culture and in animal models. In accordance with the present invention, test compounds which are shown to modulate the activity of the HSP receptor as described herein in vitro, will further be assayed in vivo, including cultured cells and animal models to determine if the test compound has the similar effects in vivo and to determine the effects of the test compound on antigen presentation, T-cell cytotoxicity, tumor progression, the accumulation or degradation of positive and negative regulators, cellular proliferation etc.

In principle, many methods known to those of skill in the art, can be readily adapted in designing the assays of the present invention. Screening methodologies are well known in the art (see e.g., PCT International Publication No. WO 96/34099, published Oct. 31, 1996, which is incorporated by reference herein in its entirety).

The screening assays, described herein, can be used to identify compounds and compositions, including peptides and organic, non-protein molecules that modulate HSP receptor activity. Recombinant, synthetic, and otherwise exogenous compounds may have binding capacity and, therefore, may be candidates for pharmaceutical agents. Alternatively, the proteins and compounds include endogenous cellular components which interact with the identified genes and proteins in vivo. Such endogenous components may provide new targets for pharmaceutical and therapeutic interventions.

Thus, in a preferred embodiment, both naturally occurring and/or synthetic compounds (e.g., libraries of small molecules or peptides), may be screened for modulating HSPR activity. In another series of embodiments, cell lysates or tissue homogenates may be screened for proteins or other compounds which bind to one of the normal or mutant hspr genes and the HSPR proteins.

Within the broad category of in vitro selection methods, several types of method are likely to be particularly convenient and/or useful for screening test agents. These include, but are not limited to, methods which measure binding of a compound to an HSPR, methods which measure a change in the ability of an HSP receptor or HSPR-positive cells to interact with an HSP or an HSP-peptide in vitro, methods which measure a change in the ability of the HSP receptor or HSPR-positive cells to interact with an HSPR antibody, and methods which measure the activity or expression of "reporter" protein, that is, an enzyme or other detectable or selectable protein, which has been placed under the control of an hspr gene control region.

All such methods are enabled by the present disclosure of substantially pure receptor proteins, substantially pure functional domain fragments, fusion proteins, antibodies, genes, and methods of making and using the same. The screening assays of the present invention also encompass high-throughput screens and assays to identify modulators of the HSP receptor expression and activity. In accordance with this embodiment, the systems described below may be formulated into kits. To this end, cells expressing the HSP receptor or cell lysates thereof can be packaged in a variety of containers, e.g., vials, tubes, microtitre well plates, bottles, and the like. Other reagents can be included in separate containers and provided with the kit; e.g., positive control samples, negative control samples, buffers, cell culture media, etc.

5.8 Assays to Identify HSPR Agonists and Antagonists

In accordance with the present invention, screening assays may be designed to detect molecules which act as agonists or antagonists of HSP receptor function. The screening assays described herein may be used to identify peptides or proteins, or derivatives, analogs and fragments thereof, that interact with the HSP receptor. Known or unknown molecules are assayed for specific binding to the HSP receptor nucleic acids, proteins, or derivatives under conditions conducive to binding, and then molecules that specifically bind to the the HSP receptor are identified. Antibodies can be generated and small molecules identified that can be used as drugs useful in regulating the immune response.

In one embodiment of the present invention, peptide libraries may be used to screen for agonists or antagonists of the HSP receptor. Diversity libraries, such as random or combinatorial peptide or nonpeptide libraries can be screened for molecules that specifically bind to the HSP receptor. Many libraries are known in the art that can be used, e.g., chemically synthesized libraries, recombinant (e.g., phage display libraries), and in vitro translation-based libraries.

Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott & Smith, 1990, Science 249:386–390; Devlin et al., 1990, Science, 249:404–406; Christian, et al., 1992, J. Mol. Biol. 227:711–718; Lenstra, 1992, J. Immunol. Meth. 152:149–157; Kay et al., 1993, Gene 128:59–65; and PCT Publication No. WO 94/18318 dated Aug. 18, 1994.

By way of examples of nonpeptide libraries, a benzodiazepine library (see e.g., Bunin et al., 1994, Proc. Natl. Acad. Sci. USA 91:4708–4712) can be adapted for use. Peptoid libraries (Simon et al., 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

Screening the libraries can be accomplished by any of a variety of commonly known methods. See, e.g., the following references, which disclose screening of peptide libraries: Parmley & Smith, 1989, Adv. Exp. Med. Biol. 251:215–218; Scott & Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. No. 5,096,815, U.S. Pat. No. 5,223,409, and U.S. Pat. No. 5,198,346, all to Ladner et al.; Rebar & Pabo, 1993, Science 263:671–673; and PCT Publication No. WO 94/18318.

In a preferred embodiment, screening can be carried out by contacting the library members with the HSP receptor protein (or nucleic acid or derivative) immobilized on a solid phase and harvesting those library members that bind to the protein (or nucleic acid or derivative). In a specific embodiment, a library can be screened by passing phage from a continuous phage display library through a column containing purified HSP receptor linked to a solid phase, such as plastic beads. By altering the stringency of the washing buffer, it is possible to enrich for phage that express peptides with high affinity for the HSP receptor. Phage isolated from the column can be cloned and the affinities of the short peptides can be measured directly. Sequences for more than one oligonucleotide can be combined to test for even higher affinity binding to the HSP receptor. Knowing which amino acid sequences confer the strongest binding to the HSP receptor, computer models can be used to identify the molecular contacts between the HSP receptor and ligand. This will allow the design of non-protein compounds which mimic those contacts. Such a compound may have the same activity of the peptide and can be used therapeutically, having the advantage of being efficient and less costly to produce.

In another specific embodiment of this aspect of the invention, the solid support is the HSP receptor protein (or nucleic acid or derivative) immobilized on a microtiter dish. Cells that express library members are cultivated under conditions that allow expression of the library members in the microtiter dish. Library members that bind to the protein (or nucleic acid or derivative) are harvested. Such methods, are described by way of example in Parmley & Smith, 1988, Gene 73:305–318; Fowlkes et al., 1992, BioTechniques 13:422–427; PCT Publication No. WO 94/18318; and in references cited hereinabove.

In another embodiment of the present invention, interactions between HSPR and a test compound may be assayed in vitro. Known or unknown molecules are assayed for specific binding to the HSP receptor nucleic acids, proteins, or derivatives under conditions conducive to binding, and then molecules that specifically bind to the the HSP receptor are identified. The two components can be measured in a variety of ways. One approach is to label one of the components with an easily detectable label, place it together with a test component(s) under conditions that allow binding to occur, perform a separation step which separates bound labeled component from unbound labeled component, and then measure the amount of bound component. In one embodiment, the HSP receptor can be labelled and added to a test agent, using conditions that allow binding to occur. Binding of the test agent can be determined using polyacrylamide gel analysis to compare complexes formed in the presence and absence of the test agent.

In another embodiment of the present invention, the screening may be performed by adding the labelled HSPR to in vitro translation systems such as a rabbit reticulocyte lysate (RRL) system and then proceeding with the binding reaction. In vitro translation-based libraries include but are not limited to those described in PCT Publication No. WO 91/05058 dated Apr. 18, 1991; and Mattheakis et al., 1994, Proc. Natl. Acad. Sci. USA 91:9022–9026.

In another embodiment, binding of HSPR to a test agent may be assayed in intact cells in culture or in animal models in the presence and absence of the test compound. For example, a labelled test agent may be mixed with macrophage cells in culture, or to crude extracts obtained from animal tissue samples, and the test compound may be added. Binding can be assayed using confocal microscopy, as described in Section 6. In yet another embodiment, the test agent may be assayed in intact cells in animal models. A labelled test agent may be administered directly to an animal. The uptake of the test agent may be measured. For these assays, host cells to which the test compound is added may be genetically engineered to express the HSP receptor and its target interactor (such as an HSP ligand or an HSPR antibody) which may be transient, induced or constitutive, or stable. For the purposes of the screening methods of the present invention, a wide variety of host cells may be used including, but not limited to, tissue culture cells, mammalian cells, yeast cells, and bacteria. Each cell type has its own set of advantages and drawbacks. Mammalian cells such as cultured magrophages, such as the HSP receptor positive cells of the invention, may be a preferred cell type in which to carry out the assays of the present invention. Bacteria and yeast are relatively easy to cultivate but process proteins differently than mammalian cells.

5.9 Assays for the Identification of Compounds that Modulate the Interaction of the HSP Receptor with Other Proteins The screening assays described herein may be used to identify peptides or proteins, or derivatives, analogs and fragments thereof, that modulate the interaction of the HSP receptor and a ligand, such as an HSP, an HSP-peptide complex, or an HSPR antibody. The present invention provides for methods of detecting such agonists and antagonists of HSPR interactions with known proteins.

In one embodiment, the HSP receptor protein or fragment, is mixed with an HSP, an HSP-peptide complex, or an HSPR antibody, and test compounds are assayed for their ability to disrupt or enhance the binding of HSPR to an HSP, HSP-peptide complex, or an HSPR antibody. A labelled HSP, HSP-peptide complex, or HSPR antibody can be mixed with HSPR or fragment or derivative thereof, and placed under conditions in which the interaction between them would normally occur, with and without the addition of the test agent. The amount of labelled component which binds HSPR can be compared in the presence or absence of test compound. In another embodiment, modulators of the interaction between HSPR and the purified or partially purified components which have been determined to interact with HSPR by the methods described in hereinabove, such as an HSPR antagonist or agonist, can identified by this method. Such potential agonists or antagonists are labelled, mixed with HSPR under conditions in which the interaction between them would normally occur, with and without the addition of the test agent. In this approach, the purified or partially purified components may be prepared by fractionation of extracts of cells expressing other components of the the HSP receptor signalling pathway, or they may be obtained by expression of cloned genes or cDNAs or fragments thereof, optionally followed by purification of the expressed material.

In another embodiment, binding of HSPR to an HSP, an HSP-peptide complex, or an HSPR antibody may be assayed in intact cells in culture or in animal models in the presence and absence of the test compound. A labelled HSP, HSP-peptide complex, or HSPR antibody may be mixed with macrophage cells in culture, or to crude extracts obtained from animal tissue samples, and the test compound may be added. Binding can be assayed using confocal microscopy, as described in Section 6. In yet another embodiment, binding of HSPR to an HSP, HSP-peptide complex, or HSPR antibody may be assayed in intact cells in animal models. A labelled HSP, or HSP-peptide complex, or HSPR antibody may be administered directly to an animal, with and without a test compound. The uptake of HSP or HSP-peptide complex, or binding of an HSPR antibody, may be measured in the presence and the absence of test compound. For these assays, host cells to which the test compound is added may be genetically engineered to express the HSP receptor and its target interactor (such as an HSP ligand or an HSPR antibody) which may be transient, induced or constitutive, or stable. For the purposes of the screening methods of the present invention, a wide variety of host cells may be used including, but not limited to, tissue culture cells, mammalian cells, yeast cells, and bacteria. Each cell type has its own set of advantages and drawbacks. Mammalian cells such as cultured magrophages, such as the HSP receptor positive cells of the invention, may be a preferred cell type in which to carry out the assays of the present invention. Bacteria and yeast are relatively easy to cultivate but process proteins differently than mammalian cells.

In another embodiment of the present invention, the screening may be performed by adding the labelled HSPR to in vitro translation systems such as a rabbit reticulocyte lysate (RRL) system and then proceeding with in vitro priming reaction. In vitro translation-based libraries include but are not limited to those described in PCT Publication No. WO 91/05058 dated Apr. 18, 1991; and Mattheakis et al., 1994, Proc. Natl. Acad. Sci. USA 91:9022–9026.

In one embodiment of the present invention, peptide libraries may be used as a source of test compounds that can be used to screen for modulators of HSPR interactions. Diversity libraries, such as random or combinatorial peptide or nonpeptide libraries can be screened for molecules that specifically bind to the HSP receptor. Many libraries are known in the art that can be used, e.g., chemically synthesized libraries, recombinant (e.g., phage display libraries), and in vitro translation-based libraries.

Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott & Smith, 1990, Science 249:386–390; Devlin et al., 1990, Science, 249:404–406; Christian, et al., 1992, J. Mol. Biol. 227:711–718; Lenstra, 1992, J. Immunol. Meth. 152:149–157; Kay et al., 1993, Gene 128:59–65; and PCT Publication No. WO 94/18318 dated Aug. 18, 1994.

By way of examples of nonpeptide libraries, a benzodiazepine library (see e.g., Bunin et al., 1994, Proc. Natl. Acad. Sci. USA 91:4708–4712) can be adapted for use. Peptoid libraries (Simon et al., 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

Screening the libraries can be accomplished by any of a variety of commonly known methods. See, e.g., the following references, which disclose screening of peptide libraries: Parmley & Smith, 1989, Adv. Exp. Med. Biol. 251:215–218; Scott & Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. No. 5,096,815, U.S. Pat. No. 5,223,409, and U.S. Pat. No. 5,198,346, all to Ladner et al.; Rebar & Pabo, 1993, Science 263:671–673; and PCT Publication No. WO 94/18318.

In vitro translation-based libraries include but are not limited to those described in PCT Publication No. WO 91/05058 dated Apr. 18, 1991; and Mattheakis et al., 1994, Proc. Natl. Acad. Sci. USA 91:9022–9026.

The separation step in this type of procedure can be accomplished in various ways. In one approach, (one of) the binding partner(s) for the labeled component can be immobilized on a solid phase prior to the binding reaction, and unbound labeled component can be removed after the binding reaction by washing the solid phase. Attachment of the binding partner to the solid phase can be accomplished in various ways known to those skilled in the art, including but not limited to chemical cross-linking, non-specific adhesion to a plastic surface, interaction with an antibody attached to the solid phase, interaction between a ligand attached to the binding partner (such as biotin) and a ligand-binding protein (such as avidin or streptavidin) attached to the solid phase, and so on.

Alternatively, the separation step can be accomplished after the labeled component had been allowed to interact with its binding partner(s) in solution. If the size differences between the labeled component and its binding partner(s) permit such a separation, the separation can be achieved by passing the products of the binding reaction through an ultrafilter whose pores allow passage of unbound labeled component but not of its binding partner(s) or of labeled component bound to its partner(s). Separation can also be achieved using any reagent capable of capturing a binding partner of the labeled component from solution, such as an antibody against the binding partner, a ligand-binding protein which can interact with a ligand previously attached to the binding partner, and so on.

5.10 Methods and Compositions for Diagnostic Use of HSP Receptor, Derivatives, and Modulators The HSP receptor is a cell surface protein present on certain macrophage, dendritic cells, and possibly other cell types, that appears to be involved in the specific uptake and re-presentation of HSPs and HSP-peptide complexes released by cells during an immune response. As such, these receptors may be important for antigen presentation pathways required for generating immune responses to proliferative disorders, such as cancer, and to infectious diseases. Therefore, HSP receptor proteins, analogues, derivatives, and subsequences thereof, HSPR nucleic acids (and sequences complementary thereto), and anti-HSPR antibodies, have uses in detecting and diagnosing such disorders.

The HSP receptor and HSPR nucleic acids can be used in assays to detect, prognose, or diagnose immune system disorders that may result in tumorigenesis, carcinomas, adenomas etc, and viral disease.

The molecules of the present invention can be used in assays, such as immunoassays, to detect, prognose, diagnose, or monitor various conditions, diseases, and disorders affecting the HSP receptor expression, or monitor the treatment thereof. In particular, such an immunoassay is carried out by a method comprising contacting a sample derived from a patient with an anti-HSP receptor antibody under conditions such that immunospecific binding can occur, and detecting or measuring the amount of any immunospecific binding by the antibody. In a specific aspect, such binding of antibody, in tissue sections, can be used to detect aberrant HSP receptor localization or aberrant (e.g., low or absent) levels of the HSP receptor. In a specific embodiment, antibody to the HSP receptor can be used to assay a patient tissue or serum sample for the presence of the HSP receptor where an aberrant level of the HSP receptor is an indication of a diseased condition. By "aberrant levels," is meant increased or decreased levels relative to that present, or a standard level representing that present, in an analogous sample from a portion of the body or from a subject not having the disorder.

The immunoassays which can be used include but are not limited to competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

hspr genes and related nucleic acid sequences and subsequences, including complementary sequences, can also be used in hybridization assays. hspr nucleic acid sequences, or subsequences thereof, comprising about at least 8 nucleotides, can be used as hybridization probes. Hybridization assays can be used to detect, prognose, diagnose, or monitor conditions, disorders, or disease states associated with aberrant changes in hspr expression and/or activity as described supra. In particular, such a hybridization assay is carried out by a method comprising contacting a sample containing nucleic acid with a nucleic acid probe capable of hybridizing to hspr DNA or RNA, under conditions such that hybridization can occur, and detecting or measuring any resulting hybridization.

In specific embodiments, diseases and disorders involving decreased immune responsiveness during an infection or malignant disorder can be diagnosed, or their suspected presence can be screened for, or a predisposition to develop such disorders can be detected, by detecting decreased levels of HSPR protein, hspr RNA, or the HSPR functional activity (e.g., binding to HSPs, antibody-binding activity etc.), or by detecting mutations in hspr RNA, DNA or HSPR protein (e.g., translocations in the HSPR nucleic acids, truncations in the HSPR gene or protein, changes in nucleotide or amino acid sequence relative to wild-type HSPR) that cause decreased expression or activity of HSPR. Such diseases and disorders include but are not limited to those described in Sections 5.12 and 5.13. By way of example, levels of the HSP receptor protein can be detected by immunoassay, levels of hspr RNA can be detected by hybridization assays (e.g., Northern blots, in situ-hybridization), HSPR activity can be assayed by measuring binding activities in vivo or in vitro. Translocations, deletions, and point mutations in HSPR nucleic acids can be detected by Southern blotting, FISH, RFLP analysis, SSCP, PCR using primers that preferably generate a fragment spanning at least most of the the HSP receptor gene, sequencing of hspr genomic DNA or cDNA obtained from the patient, etc.

In a preferred embodiment, levels of hspr mRNA or protein in a patient sample are detected or measured relative to the levels present in an analogous sample from a subject not having the malignancy or hyperproliferative disorder. Decreased levels indicate that the subject may develop, or have a predisposition to developing, viral infection, malignancy, or hyperproliferative disorder.

In another specific embodiment, diseases and disorders involving a deficient immune responsiveness resulting in cell proliferation or in which cell proliferation is desirable for treatment, are diagnosed, or their suspected presence can be screened for, or a predisposition to develop such disorders can be detected, by detecting increased levels of the HSP receptor protein, hspr RNA, or the HSP receptor functional activity (e.g., HSP ligand binding or HSPR antibody, etc.), or by detecting mutations in hspr RNA, DNA or protein (e.g., translocations in hspr nucleic acids, truncations in the gene or protein, changes in nucleotide or amino acid sequence relative to wild-type hspr) that cause increased expression or activity of the HSP receptor. Such diseases and disorders include, but are not limited to, those described in Section 5.7.3. By way of example, levels of the HSP receptor protein, levels of hspr RNA, HSPR binding activity, and the presence of translocations or point mutations can be determined as described above.

In a specific embodiment, levels of hsrp mRNA or protein in a patient sample are detected or measured, relative to the levels present in an analogous sample from a subject not having the disorder, in which increased levels indicate that the subject has, or has a predisposition to, an autoimmune disorder.

Kits for diagnostic use are also provided, that comprise in one or more containers an anti-the HSP receptor antibody, and, optionally, a labeled binding partner to the antibody. Alternatively, the anti-the HSP receptor antibody can be labeled (with a detectable marker, e.g., a chemiluminescent, enzymatic, fluorescent, or radioactive moiety). A kit is also provided that comprises in one or more containers a nucleic acid probe capable of hybridizing to hspr RNA. In a specific embodiment, a kit can comprise in one or more containers a pair of primers (e.g., each in the size range of 6–30 nucleotides) that are capable of priming amplification [e.g., by polymerase chain reaction (see e.g., Innis et al., 1990, PCR Protocols, Academic Press, Inc., San Diego, Calif.), ligase chain reaction (see EP 320,308) use of Qβ replicase, cyclic probe reaction, or other methods known in the art] under appropriate reaction conditions of at least a portion of a hspr nucleic acid. A kit can optionally further comprise in a container a predetermined amount of a purified the HSP receptor protein or nucleic acid, e.g., for use as a standard or control.

5.11 Methods and Compositions for Therapeutic Use of HSP Receptor Protein, Derivatives, and Modulators In certain instances, compounds and methods that increase or enhance the activity of the HSP receptor can be used to treat immune disorders such as immunodeficiency syndromes, cancers or infectous diseases. Such a case may involve, for example, an immune system disorder that is brought about, at least in part, by a reduced level of hspr gene expression, or an aberrant level of an hspr gene product's activity. For example, underexpression of the HSP receptor or its decreased activity or ability to interact with an HSP molecule may result in lack of antigen presentation and a suppressed immune response. As such, an increase in the level of gene expression and/or the activity of such hspr gene products would bring about the amelioration of proliferative disease symptoms.

In another instance, compounds that increase or enhance the activity of the HSP receptor can be used to treat immunodeficiency syndromes, cancers or infectious diseases that are caused by defects in the expression or activity of other genes and gene products involved in the HSP antigen presentation pathway. For example, an increase in the expression or activity of an HSP that interacts with the HSP receptor may result in a decrease in its ability to take up additional HSP peptide complexes. Such a decrease in activity may lead to a weakened immune response. Disease symptoms resulting from such a defect may be ameliorated by compounds that compensate the disorder by increased the HSP receptor expression or activity. Techniques for increasing the HSP receptor gene expression levels or gene product activity levels are discussed in Section 5.7, below.

Alternatively, compounds and methods that reduce or inactivate the HSP receptor activity may be used therapeutically to ameliorate immune disorders resulting in proliferative and viral disease symptoms. For example, an immune disorder may be caused, at least in part, by a defective the HSP receptor gene or gene product that leads to its overactivity. In such an instance, compounds and methods that reduce or inactivate the HSP receptor function may be used to treat the disease symptoms.

In another instance, compounds and methods that reduce the activity of the HSP receptor can be used to treat disorders resulting from defects in the expression or activity of other genes and gene products involved antigen presentation pathways such as HSP receptor ligands. Compounds and methods aimed at reducing the expression and/or activity of such the HSP receptor molecules could be used in the treatment of disease symptoms by compensating for the defective gene or gene product.

Techniques for the reduction of target gene expression levels or target gene product activity levels are discussed in Section 5.7 below.

5.11.1 Therapeutic Use of Identified Agonists and Antagonists

Antibodies, agonists, antagonists, antisense RNAs and ribozymes that interfere with the HSP receptor activity can be useful as therapeutics. Such drugs can be used to down-regulate autoimmune responses. Other antibodies, agonists, antagonists, antisense RNAs and ribozymes may upregulate the HSP receptor expression, and would be useful in stimulating a host's immune system prior to or concurrent with the administration of a vaccine. Described below are methods and compositions for the use of such compounds in the treatment of immune disorders and oncogenic or viral disease.

In one embodiment, symptoms of certain hspr gene disorders, such as such as proliferative or differentiative disorders causing tumorigenesis or cancer, may be ameliorated by increasing the level of hspr gene expression and/or hspr gene product activity by using hspr gene sequences in conjunction with well-known antisense, gene "knock-out," ribozyme and/or triple helix methods to decrease the level of hspr gene expression. Among the compounds that may exhibit the ability to modulate the activity, expression or synthesis of the hspr gene, including the ability to ameliorate the symptoms of an hspr disorder, such as cancer, are antisense, ribozyme, and triple helix molecules. Such molecules may be designed to reduce or inhibit either unimpaired, or if appropriate, mutant target gene activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarity, although preferred, is not required.

A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the hspr gene could be used in an antisense approach to inhibit translation of endogenous hspr mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

In an embodiment of the present invention, oligonucleotides complementary to the nucleic acids encoding the the HSP receptor ligand binding domain are used.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oglionucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, Proc. Natl. Acad. Sci. U.S.A. 86, 6553–6556; Lemaitre, et al., 1987, Proc. Natl. Acad. Sci. 84, 648–652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6, 958–976) or intercalating agents (see, e.g., Zon, 1988, Pharm. Res. 5, 539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate (S-ODNs), a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier, et al., 1987, Nucl. Acids Res. 15, 6625–6641). The oligonucleotide is a 2'-0-methylribonucleotide (Inoue, et al., 1987, Nucl. Acids Res. 15, 6131–6148), or a chimeric RNA-DNA analogue (Inoue, et al., 1987, FEBS Lett. 215, 327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein, et al. (1988, Nucl. Acids Res. 16, 3209), methylphosphonate oligonucleotides can be prepared by use of controlled pore glass polymer supports (Sarin, et al., 1988, Proc. Natl. Acad. Sci. U.S.A. 85, 7448–7451), etc.

While antisense nucleotides complementary to the target gene coding region sequence could be used, those complementary to the transcribed, untranslated region are most preferred.

In one embodiment of the present invention, gene expression downregulation is achieved because specific target mRNAs are digested by RNAse H after they have hybridized with the antisense phosphorothioate oligonucleotides (S-ODNs). Since no rules exist to predict which antisense S-ODNs will be more successful, the best strategy is completely empirical and consists of trying several antisense S-ODNs. Antisense phosphorothioate oligonucleotides (S-ODNs) will be designed to target specific regions of mRNAs of interest. Control SODNs consisting of scrambled sequences of the antisense SODNs will also be designed to assure identical nucleotide content and minimize differences potentially attributable to nucleic acid content. All S-ODNs can be synthesized by Oligos Etc. (Wilsonville, Oreg.). In order to test the effectiveness of the antisense molecules when applied to cells in culture, such as assays for research purposes or ex vivo gene therapy protocols, cells will be grown to 60–80% confluence on 100 mm tissue culture plates, rinsed with PBS and overlaid with lipofection mix consisting of 8 ml Opti-MEM, 52.8 µl Lipofectin, and a final concentration of 200 nM S-ODNs. Lipofections will be carried out using Lipofectin Reagent and Opti-MEM (Gibco BRL). Cells will be incubated in the presence of the lipofection mix for 5 hours. Following incubation the medium will be replaced with complete DMEM. Cells will be harvested at different time points post-lipofection and protein levels will be analyzed by Western blot.

Antisense molecules should be targeted to cells that express the target gene, either directly to the subject in vivo or to cells in culture, such as in ex vivo gene therapy protocols. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290, 304–310), the promoter contained in the 3' long terminal repeat of Rous sarcoma virus (Yamamoto, et al., 1980, Cell 22, 787–797), the herpes thymidine kinase promoter (Wagner, et al., 1981, Proc. Natl. Acad. Sci. U.S.A. 78, 1441–1445), the regulatory sequences of the metallothionein gene (Brinster, et al., 1982, Nature 296, 39–42), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication WO90/11364, published Oct. 4, 1990; Sarver, et al., 1990, Science 247, 1222–1225). In an embodiment of the present invention, oligonucleotides which hybridize to the the HSP receptor gene are designed to be complementary to the nucleic acids encoding the the HSP receptor ligand binding domain.

Ribozymes are enzymatic RNA molecules capable of catalyzing the specific cleavage of RNA. (For a review, see Rossi, 1994, Current Biology 4, 469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, *Molecular Biology and Biotechnology: A Comprehensive Desk Reference*, VCH Publishers, New York, (see especially FIG. 4, page 833) and in Haseloff & Gerlach, 1988, Nature, 334, 585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in *Tetrahymena thermophila* (known as the IVS, or L-19 IVS RNA) and that has been extensively described by Thomas Cech and collaborators (Zaug, et al., 1984, Science, 224, 574–578; Zaug and Cech, 1986, Science, 231, 470–475; Zaug, et al., 1986, Nature, 324, 429–433; published International patent application No. WO 88/04300 by University Patents Inc.; Been & Cech, 1986, Cell, 47, 207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al., 1985, Nature 317, 230–234; Thomas & Capecchi, 1987, Cell 51, 503–512; Thompson, et al., 1989, Cell 5, 313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited modifications to ES (embryonic stem) cells can be used to generate animal offspring with an inactive target gene (e.g., see Thomas & Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, Anticancer Drug Des., 6(6), 569–584; Helene, et al., 1992, Ann. N.Y. Acad. Sci., 660, 27–36; and Maher, 1992, Bioassays 14(12), 807–815).

Nucleic acid molecules to be used in triple helix formation for the inhibition of transcription should be single stranded and composed of deoxyribonucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and $CGC^+$ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.10.2 that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.11.2 Gene Replacement Therapy

With respect to an increase in the level of normal hspr gene expression and/or hspr gene product activity, hspr gene nucleic acid sequences, described, above, in Section 5.4 can, for example, be utilized for the treatment of immune disorders resulting in proliferative disorders such as cancer. Such treatment can be administered, for example, in the form of gene replacement therapy. Specifically, one or more copies of a normal hspr gene or a portion of the hspr gene that directs the production of an hspr gene product exhibiting normal hspr gene function, may be inserted into the appropriate cells within a patient, using vectors that include, but are not limited to adenovirus, adeno-associated virus, and retrovirus vectors, in addition to other particles that introduce DNA into cells, such as liposomes.

Gene replacement therapy techniques should be capable of delivering hspr gene sequences to cell types that express the HSP receptor within patients. Thus, in one embodiment, techniques that are well known to those of skill in the art (see, e.g., PCT Publication No. WO89/10134, published Apr. 25, 1988) can be used to enable hspr gene sequences to be delivered to developing cells of the myeloid lineage, for example, to the bone marrow. In another specific embodiment, gene replacement can be accomplished using macrophages in vitro, and delivered to a patient using the techniques of adoptive immunotherapy.

In another embodiment, techniques for delivery involve direct administration of such hspr gene sequences to the site of the cells in which the hspr gene sequences are to be expressed, e.g., directly at the site of the tumor.

Additional methods that may be utilized to increase the overall level of hspr gene expression and/or hspr gene product activity include the introduction of appropriate hspr-expressing cells, preferably autologous cells, into a patient at positions and in numbers that are sufficient to ameliorate the symptoms of an hspr disorder. Such cells may be either recombinant or non-recombinant.

Among the cells that can be administered to in increase the overall level of hspr gene expression in a patient are cells that normally express the hspr gene.

Alternatively, cells, preferably autologous cells, can be engineered to express hspr gene sequences, and may then be introduced into a patient in positions appropriate for the amelioration of the symptoms of an hspr disorder or a proliferative or viral disease, e.g., cancer and tumorigenesis. Alternately, cells that express an unimpaired hspr gene and that are from a MHC matched individual can be utilized, and may include, for example, brain cells. The expression of the hspr gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, U.S. Pat. No. 5,399,349.

When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

Additionally, compounds, such as those identified via techniques such as those described hereinabove, in Section 5.7, that are capable of modulating hspr gene product activity can be administered using standard techniques that are well known to those of skill in the art.

5.12 Target Infectious Diseases

Infectious diseases that can be treated or prevented by the methods of the present invention are caused by infectious agents including, but not limited to, viruses, bacteria, fungi protozoa and parasites.

Viral diseases that can be treated or prevented by the methods of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II).

Bacterial diseases that can be treated or prevented by the methods of the present invention are caused by bacteria including, but not limited to, mycobacteria rickettsia, mycoplasma, neisseria and legionella.

Protozoal diseases that can be treated or prevented by the methods of the present invention are caused by protozoa including, but not limited to, leishmania, kokzidioa, and trypanosoma.

Parasitic diseases that can be treated or prevented by the methods of the present invention are caused by parasites including, but not limited to, chlamydia and rickettsia.

5.13 Target Proliferative Cell Disorders

With respect to specific proliferative and oncogenic disease associated with the HSP receptor activity, the diseases that can be treated or prevented by the methods of the present invention include but are not limited to: human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leibmyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland acarcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease.

Diseases and disorders involving a deficiency in cell proliferation or in which cell proliferation is desired for treatment or prevention, and that can be treated or prevented by inhibiting the HSP receptor function, include but are not limited to degenerative disorders, growth deficiencies, hypoproliferative disorders, physical trauma, lesions, and wounds; for example, to promote wound healing, or to promote regeneration in degenerated, lesioned or injured tissues, etc.

5.14 Pharmaceutical Preparations and Methods of Administration

The compounds that are determined to affect hspr gene expression or gene product activity can be administered to a patient at therapeutically effective doses to treat or ameliorate a cell proliferative disorder. A therapeutically effective dose refers to that amount of the compound sufficient to result in amelioration of symptoms of such a disorder.

5.14.1 Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.14.2 Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

6. Example Identification of gp96 Receptor 6.1 Introduction

The Example presented herein describes the successful identification of a gp96 receptor present in macrophages and dendritic cells, and the isolation and purification of gp96-receptor positive cells. Described herein are experiments that demonstrate the specific uptake of gp96 molecules by macrophage cells. Such gp96-receptor positive cells are used for the generation and purification of a specific antibody against the gp96 receptor. The experiments presented herein form the basis for the methods of the present invention for isolating HSP receptor proteins and nucleic acids, and for anti-viral and anti-cancer therapies.

6.2 Materials and Methods

Gp96 (gp96-biot) and phosphorylase b (Pb-biot) were covalently linked to biotin using the sulfo-NHS-LC-biotin reagent (sulfosuccinimidyl-6-9-biotinamido)hexanoate, which has a 22 Angstrom spacer arm. After biotinylation, gp96-biot and Pb-biot were dialyzed overnight at 4° C. against phosphate bufferred saline (PBS) and concentrated using polyethylene glycol (PEG) 15000-20000. Biotinlated bovine serum albumin (BSA) (BSA-biot) was purchased from SIGMA. The quality of biotinlation was verified by Western blotting and detected with avidin-peroxidase.

For the fluorescent probes, Alexa 568 streptavidin conjugate used for confocal microscopy was purchased from Molecular Probe. The avidin-FITC (Sigma). Propidium iodide (SIGMA) is a fluorescent DNA binding probe used to assess the viability of cells.

Four to six-week old female C57BL/ mice were purchased from Jackson Laboratories. 4 week old female ImmortoMouse mice were purchased from Charles River Laboratories, Inc. These transgenic mice express a thermolabile SV40 T antigen under the control of the mouse H2Kb MHC class I promoter. Cells of these mice can be immortalized in culture under permissive conditions (33° C. in the presense of interferon) such that it became easy to establish macrophage lines (Jat et al., 1991).

Resident (PEC) cells: the peritoneal cavity of 6 to 10 week old C57BL/6 mice was washed with cold PBS, and the total peritoneal exudate cells were harvested and washed once in PBS.

Pristane PEC: Six to eight week old C57BL/6 mice were injected with 0.5 ml of pristane (2,6,10,14-tetramethypentadecane) to induce a chronic inflammatory response in the peritoneum. This inflamation is characterized by a massive increase of Mac-1+ cells, presumably macrophages and neutrophils, and CD4+ T cells in the peritoneum (McDonald and Degrassi, 1993). Five to fifteen days after the injection of pristane, the PEC were harvested and washed as described for the resident PEC.

All antibodies used for FACScan analysis was purchased from Pharmingen and used as recommended. FACScan analysis were performed according to Becton Dickenson, San Jose, Calif. Briefly, $1 \times 10^6$ cells were washed twice and resuspended in 200 $\mu$l of PBS with 2% fetal calf serum. Antibodies (tagged to fluorochrome; FITC or phycoerythrin)

were incubated with cells on ice for 30 mins in the dark. Cells were washed twice each with 2 ml of PBS, resuspended in 700 ml PBS and analyzed on a FACScan. Only live cells were gated and analyzed. Prior to labeling of macrophages with antibody, Fc receptors were blocked with Fc Block antibody (αCD16/CD32; Pharmingen). Spleen cells were depleted of red blood cells prior to analysis by FACScan.

6.3 Results

Figure 1B:
Figure 1C:
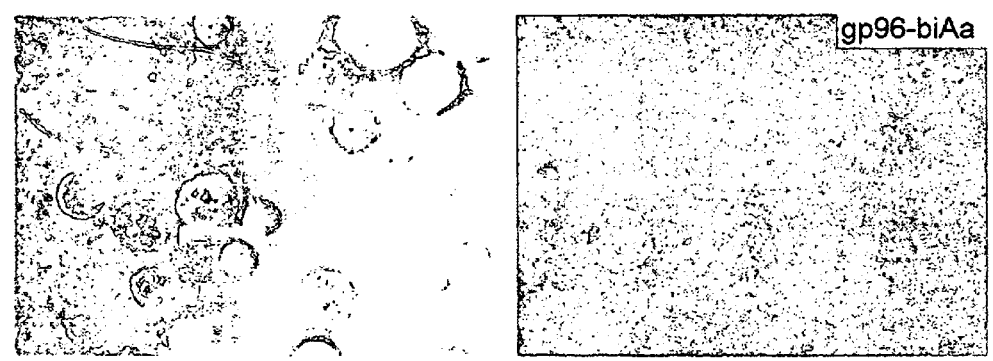
Figure 3:
Figure 3:

In order to address the question whether cells have a specific mechanism to take up HSP-peptide complexes, mice peritoneal exudate cells (PECs) were incubated with biotin-labelled gp96, detected with a fluorescent probe (Alexa 568) and examined using confocal microscopy. As shown in FIG. 1, right panels, the cell membranes of PECs derived from C57BL/6 mice became specifically labelled with biotin-labelled gp96, but not with the biotin-labelled BSA. These results suggested that HSP becomes specifically associated with membranes of peritoneal macrophage. These results were consistent with the existence of an HSP receptor on the cell surface. Similar results were found in another strain of mouse, the transgenic mouse, ImmortoMouse, as shown in FIG. 3. $2 \times 10^5$ Mac-1+ PECs from 7 day pristaned mice were blocked with 5% BSA, then incubated with indicated concentrations of FITC-labelled HSP.

FIG. 2 shows a time course of gp96 association with PECs. PECs were incubated with biotin-labelled gp96 for various lengths of time, at either 37° C. (Panel A) or 4° C. (Panel B) to examine-the internalization of gp96. Peritoneal cells were incubated with biotin-labelled gp96, and a single cells was examined using confocal microscopy after 0, 2, 4, 6, 8, 10, 12, or 14 mins. As shown in FIG. 2A, cells incubated at 37° C. rapidly internalized gp96. After less than 10 minutes, most of the biotin-label was found inside the cell. In contrast, when similar experiments were performed at 4° C. the internalization of gp96 was prevented, even after two hours of incubation (Panel B).

In order to verify that gp96 binds specifically to internalized by viable macrophages, a FacScan analysis of HSPs was performed, as shown in FIG. 4. HSP90 (FIGS. 4C, 4G, 4K, 4O, 4S), gp96 (FIGS. 4D, 4H, 4L, 4P, 4T), HSP70 (FIGS. 4E, 4I, 4M, 4O, 4U), and BSA (FIGS. 4F, 4J, 4N, 4R, 4V) were labelled with fluorescein isothiocyanate (FITC) and pulsed on to Mac-1 positive cells (macrophages) at various concentrations of HSP. Cells were also labelled with propidium iodide, which stains DNA and marks dead cells. The three HSPs and BSA at concentrations of 10 µg/ml (FIGS. 4C–F), 20 µg/ml (FIGS. 4G–I), 50 µg/ml (FIGS. 4k–N), 100 µg/ml (FIGS. 4O–R), and 190 µg/ml (FIGS. 4S–V) are shown. The propidium iodide (PI) label, indicated along X axis, labels DNA, and indicated the presence of dead cells. The absorbance of FITC-labelled HSP is indicated along the X axis.

FIG. 5 shows that the saturation of binding to HSP receptor by $^{125}$I-labelled gp96 in cells of two mouse strains, BALB/C Mac-1+ cells and C57BL/6 Mac-1+ (macrophage) cells. 125I-labelled BSA is shown as a negative control, since there is no known receptor for BSA. In this experiment in gp96 and BSA were labelled with $^{125}$Iodine and added to anti-Mac-1 antibody purified macrophage from two mice strains, Balb/C and C57BL/6. The cells were then placed in a gamma counter to determine radioactivity. The uptake of gp96 reaches saturation at about 40 µg protein, whereas BSA binds only minimally and does not show saturation at the concentrations tested. If uptake was occurring by pinocytosis, BSA and gp96 would not be expected to yield different saturation profiles and gp96 would not be expected to reach saturation at such minimal concentrations. These results suggest, therefore, that gp96 is taken up by the cell by a receptor-mediated mechanism.

7. Expression Cloning of the HSP Receptor

7.1. Panning Method

Purified gp96 is coated on plastic, and a modified version of the procedure of Aruffo and Seed (1987, Proc. Natl. Acad. Sci. USA 84:3365–3369) for selecting cDNAs by expression in COS cells is used, as modified by Staunton et al. (1989, Nature 339:61–64), as detailed below.

gp96 is purified as described in in Section 5.2, supra. Alternatively, purified gp96 is obtained by recombinant methods by expression from cells transfected with a DNA clone encoding gp96. gp96 (10 µg per 200 µl per 6-cm plate) is bound to bacteriological Petri dishes by overnight incubation at 4° C. Plates are blocked with 1% BSA and stored in PBS/2 mM $MgCl_2$/0.2% BSA/0.025% azide/50 µg ml$^{-1}$ gentamycin.

Synthesis of a cDNA library from HSPR positive cells is as described in Section 5.43 or in Staunton et al., 1988, Cell 52:925–933. After second-strand synthesis, the cDNA is ligated to BstXI adaptors (Seed and Aruffo, 1987, Proc. Natl. Acad. Sci. USA 84:3365–3369), and cDNAs longer than 600 bp are selected by low-melting point agarose gel electrophoresis. The cDNA is then preferably ligated to a plasmid vector such as CDM8 (Seed, 1987, Nature 329:840–842), that replicates in certain prokaryotic as well as certain eukaryotic cells and provides for expression of recombinant proteins in certain eukaroytic cells. The vectors are then introduced into *E. coli* host MC1061/P3 and plated to obtain $5 \times 10^5$ colonies. The colonies are suspended in LB medium, pooled and plasmid prepared by standard alkalilysis method (Sambrook et al., 1989, in *Molecular Cloning, A Laboratory Manual*, 2 d ed., Cold Spring Harbor Laboratory, New York).

Ten 10-cm plates of COS cells at 50% confluency are transfected with 10 µg per plate of the plasmid cDNA library using DEAE-dextran (Kingston, 1987, in *Current Protocols in Molecular Biology*, Greene Publishing Assocs., pp. 911–996). COS cells three days after transfection are suspended by treatment with 0.025% trypsin/1 mM EDTA/HBSS (Gibco), and panned (Seed and Aruffo, 1987, Proc. Natl. Acad. Sci. USA 84:3365–3369) on gp96 coated plates. The cell suspension is incubated in the gp96 coated plates at 25° C. for 1 hour. The transfected COS cells are incubated in the gp96 coated dishes. Nonadherent cells are removed by gentle rocking and three washes with buffer. Adherent cells are eluted by addition of 10 mM EDTA. Plasmid is recovered from the adherent population of COS cells in Hirt supernatants. The *E. coli* strain MC1061/P3 is transformed with the plasmid, and colonies on plates are suspended in LB medium, pooled, and plasmid is prepared by the alkali-lysis method. Selection of gp96-adherent transfected COS cells and plasmid recovery is repeated twice. Pooled colonies obtained after the third cycle are grown to saturation in 100 ml LB medium with 18 µg/ml tetracycline and 20 µg/ml ampicillin. Plasmid is prepared and fractionated by 1% low-melting point agarose gel electrophoresis, and MC1061/P3 is transformed separately with plasmid from different size fractions. Individual plasmids from the fraction with greatest activity in promoting adhesion to gp96 of COS cells transfected with such plasmids are examined for uniqueness by restriction enzyme digestion and DNA sequencing, and re-tested in the COS cell adherence assay.

Alternatively, adherent cells can be isolated by using a plastic cloning cylinder preferably less than 5 mm in diameter and about 1 cm tall, with vacuum grease at its edge to form a seal, to surround the COS cell on the plastic surface. A trypsin-EDTA solution is poured into the plastic cylinder, and allowed to sit for five minutes at room temperature, in order to elute the COS cell from the plastic. The cell solution is then removed to a microfuge tube, and plasmid cDNA is purified from the eluted cell(s) by known methods. Since sometimes more than a single COS cell is thus isolated, and since a single COS cell can contain more than one cDNA clone, preferably, additional procedures are then used to isolate a single clone: The purified cDNA is used to transform competent E. coli, followed by purification of cDNA from individual colonies of transformed E. coli. Samples containing each individual cDNA clone are used to transfect COS cells which are then cultured, and incubated in Petri dishes that contain gp96 (or other heat shock protein). The incubation is carried out for a period of time sufficient to allow binding of a transfected COS cell to the plate coated with gp96. The cDNA clone which gave rise to a transfected COS cell thus bound is identified as the gp96 receptor cDNA clone.

8. Production of Antibody and Isolation of the gp96 Receptor by Antibody Binding A monoclonal antibody is raised, against the gp96 receptor of the invention, that can inhibit binding of gp96 to HSPR positive cells.

Cell culture is carried out as described in Section 6.1.1, supra.

HSPR positive cells are used to immunize three 12-wkold BALB/c female mice (Charles River Laboratories, Wilmington, Mass.). Immunizations (105–106 cells per intraperitoneal immunization) are given three times at 3-wk intervals. The protocol for fusion and subsequent maintenance of hybridomas is as described previously (Galfre and Milstein, 1981, Meth. Enzymol. 73:3). Approximately 1,000 hybridomas are screened for the ability to inhibit gp96 binding to HSPR positive cells. An antibody with such ability is cloned three times by limiting dilution. The antibody is once again screened for the ability to inhibit gp96 binding to HSPR positive cells. The antibody can be isotyped by ELISA using affinity-purified antibodies to mouse immunoglobulins (Zymed Immunochemicals, San Francisco, Calif.).

To purify the gp96 receptor, the monoclonal antibody (mAb) isolated above is used in immunoaffinity chromatography by the methods described in Section 5.2 to isolate the gp96 receptor, or in immunoprecipitation assays.

For immunoprecipitation of the gp96 receptor HSPR positive cells are surface labeled with $^{125}$I as described using Iodogen (Pierce Chemical Co., Rockford, Ill.) (Kishimoto et al., 1989, J. Biol. Chem. 264:3588). Triton X-100 (1%) lysates are cleared with bovine IgG-coupled-Sepharose and then incubated with the mab-bound Sepharose for 2 h. Beads are washed and heated at 100° C. in sample buffer containing 50 mM Tris, 1% SDS, and 1% 2-mercaptoethanol or 20 mM iodoacetamide. Samples are subjected to sodium dodecyl sulfate 7% polyacrylamide gel electrophoresis (Laemmli, 1970, Nature 227:680) and autoradiography with enhancing screens.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for screening a small organic molecule for the ability to modulate heat shock protein receptor activity comprising:

(a) contacting heat shock protein receptor positive cells with the small organic molecule; and (b) comparing the level of heat shock protein receptor binding activity in the heat shock protein receptor positive cells contacted with the small organic molecule to the amount of heat shock protein receptor binding activity in such heat shock protein receptor positive cells not so contacted, wherein an increase or decrease in the amount of heat shock protein receptor binding activity in the contacted heat shock protein receptor positive cells relative to the amount of heat shock protein receptor binding activity in the heat shock protein receptor positive cells not so contacted indicates that the small organic molecule has the ability to modulate heat shock protein receptor activity.

2. The method of claim 1 wherein the level of heat shock protein receptor binding activity is assayed by measuring the ability of the small organic molecule to bind to the heat shock protein receptor positive cells.

3. The method of claim 1 wherein the small organic molecule is attached to a solid surface.

4. A method for screening a molecule for the ability to modulate heat shock protein receptor activity comprising:

(a) contacting heat shock protein receptor positive cells with the molecule; and (b) comparing the level of heat shock protein receptor binding activity in the heat shock protein receptor positive cells contacted with the molecule to the amount of heat shock protein receptor binding activity in such heat shock protein receptor positive cells not so contacted, wherein an increase or decrease in the amount of heat shock protein receptor binding activity in the contacted heat shock protein receptor positive cells relative to the amount of heat shock protein receptor binding activity in the heat shock protein receptor positive cells not so contacted indicates that the molecule has the ability to modulate heat shock protein receptor activity, wherein the level of heat shock protein receptor binding activity is assayed by measuring the ability of the molecule to modulate the binding of a heat shock protein or a heat shock protein-peptide complex to the cells.

5. The method of claim 1 or 4 wherein the heat shock protein receptor binding activity is the ability to interact with a heat shock protein receptor antibody.

6. The method of claim 1 or 4, wherein the heat shock protein receptor is selected from the group consisting of an Hsp70 receptor, an Hsp 90 receptor, and a gp96 receptor.

7. The method of claim 1 or 4, wherein the heat shock protein receptor positive cells are purified from heat shock protein receptor negative cells.

8. The method of claim 4 wherein the molecule decreases the binding of the heat shock protein or the heat shock protein-peptide complex to the cells.

9. The method of any one of claim 4, 5 or 8 wherein the heat shock protein is an Hsp70, an Hsp 90, or gp96.

10. The method of claim 4 wherein the molecule is a peptide or protein, or derivative, analog or fragment thereof.

11. The method of claim 10 wherein the peptide is a member of a peptide library.

12. The method of claim 4 wherein the molecule is a small organic molecule, a nonpeptide, or an antibody.

13. The method of claim 12 wherein the nonpeptide is a member of a nonpeptide library.

14. The method of claim 1 or 12 wherein the small organic molecule is a member of a small molecule library.

15. A method for identifying a molecule potentially useful for the treatment of cancer comprising carrying out the method of claim 1 or 4, further comprising the step of administering the molecule to a non-human animal having a tumor, and determining whether the molecule alters tumor progression in the non-human animal.

16. The method of claim 15, wherein the heat shock protein receptor is selected from the group consisting of an Hsp70 receptor, an Hsp 90 receptor, and a gp96 receptor.

17. The method of claim 15, wherein the heat shock protein receptor positive cells are purified from heat shock protein receptor negative cells.

18. A method for identifying a molecule potentially useful for the treatment of an infectious disease comprising carrying out the method of claim 1 or 4, further comprising the step of administering the molecule to a non-human animal infected with a pathogen, and determining whether the molecule ameliorates the infectious disease in the non-human animal.

19. The method of claim 18, wherein the heat shock protein receptor is selected from the group consisting of an Hsp70 receptor, an Hsp 90 receptor, and a gp96 receptor.

20. The method of claim 18, wherein the heat shock protein receptor positive cells are purified from heat shock protein receptor negative cells.

21. A method for identifying a molecule potentially useful for the treatment of an autoimmune disease comprising carrying out the method of claim 1 or 4, further comprising the step of administering the molecule to a non-human animal suffering from an autoimmune disease, and determining whether the molecule ameliorates the autoimmune disease in the non-human animal.

22. The method of claim 21, wherein the heat shock protein receptor is selected from the group consisting of an Hsp70 receptor, an Hsp 90 receptor, and a gp96 receptor.

23. The method of claim 21, wherein the heat shock protein receptor positive cells are purified from heat shock protein receptor negative cells.

24. A method for screening a plurality of molecules for one or more molecules having the ability to modulate, directly or indirectly, the ability of heat shock protein receptor positive cells to stimulate the activation of cytotoxic T cells in vitro comprising:
(a) contacting said plurality of molecules with: (i) heat shock protein receptor positive cells; (ii) a purified complex of a heat shock protein and a peptide; and (iii) cytotoxic T cells, under conditions conducive to the activation of cytotoxic T cells; and
(b) comparing antigenic cell cytotoxicity of said T cells with the antizenic cell cytotoxicity of T cells contacted with said heat shock protein receptor positive cells and said purified complex under said conditions, but in the absence of said plurality of molecules,
wherein a lower or higher degree of cytotoxicity indicates that one or more molecules in said plurality of molecules modulates the ability of heat shock protein receptor positive cells to stimulate the activation of cytotoxic T cells against the peptide.

25. A method for screening an antibody specific to a heat shock protein or specific to a heat shock protein receptor for the ability to modulate, directly or indirectly, the ability of heat shock protein receptor positive cells to stimulate the activation of cytotoxic T cells in vitro comprising:
(a) contacting the antibody with heat shock protein receptor positive cells and cytotoxic T cells under conditions conducive to the activation of cytotoxic T cells; and
(b) comparing antigenic cell cytotoxicity of said T cells with the antigenic cell cytotoxicity of T cells contacted with said heat shock protein receptor positive cells under said conditions, but in the absence of said antibody,
wherein a lower or higher degree of cytotoxicity indicates that the antibody modulates the ability of heat shock protein receptor positive cells to stimulate the activation of cytotoxic T cells against the antibody.

26. A method for screening a molecule for the ability to modulate, directly or indirectly, the ability of beat shock protein receptor positive cells to stimulate the activation of cytotoxic T cells in vitro comprising:
(a) contacting the molecule with: (i) purified heat shock protein receptor positive cells; (ii) a purified complex of a heat shock protein and a peptide; and (iii) cytotoxic T cells, under conditions conducive to the activation of cytotoxic T cells; and
(b) comparing antigenic cell cytotoxicity of said T cells with the antigenic cell cytotoxicity of T cells contacted with said heat shock protein receptor positive cells and said purified complex under said conditions, but in the absence of said molecule,
wherein a lower or higher degree of cytotoxicity indicates that the molecule modulates the ability of heat shock protein receptor positive cells to stimulate the activation of cytotoxic T cells against the peptide.

27. A method for screening a plurality of molecules for one or more molecules having the ability to modulate, directly or indirectly, antigen presentation activity of heat shock protein receptor positive cells comprising:
(a) contacting said plurality of molecules with heat shock protein receptor positive cells;
(b) measuring antigen presentation by said heat shock protein receptor positive cells in the presence of said plurality of molecules; and
(c) comparing antigen presentation activity by the heat shock protein receptor positive cells in the presence of said plurality of molecules with the antigen presentation activity by the heat shock protein receptor positive cellst in the absence of said plurality of molecules,
wherein a lower or higher degree of antigen presentation indicates that one or more molecules modulates the antigen presentation activity of the heat shock protein receptor positive cells.

28. The method of claims 24 or 27, wherein the molecules are peptides or proteins, or derivatives, analogs or fragments thereof.

29. The method of claim 24 or 27, wherein the molecules are a small organic molecules or a nonpeptides.

30. The method of claim 24 or 27, wherein the molecules are attached to a solid surface.

31. The method of claim 24 or 27, wherein the molecules are purified.

32. A method for screening an antibody specific to a heat shock protein or a heat shock protein receptor for the ability to modulate, directly or indirectly, antigen presentation activity of heat shock protein receptor positive cells comprising:
(a) contacting an antibody specific to a heat shock protein or a heat shock protein receptor with heat shock protein receptor positive cells;
(b) measuring antigen presentation by said heat shock protein receptor positive cells in the presence of said antibody; and
(c) comparing antigen presentation activity by the heat shock protein receptor positive cells in the presence of the antibody with the antigen presentation activity by the heat shock protein receptor positive cells in the absence of the antibody,
wherein a lower or higher degree of antigen presentation indicates that the antibody modulates the antigen presentation activity of the heat shock protein receptor positive cells.

33. The method of claim 25 or 32, wherein the antibody is attached to a solid surface.

34. The method of claim 25 or 32, wherein the antibody is purified.

35. A method for identifying an antibody potentially useful for the treatment of cancer comprising carrying out the method of claim or 25 or 32, further comprising the step of administering the antibody to a non-human animal having a tumor, and determining whether the antibody alters tumor progression in the non-human animal.

36. A method for identifying an antibody potentially useful for the treatment of an infectious disease comprising carrying out the method of claim 25 or 32, further comprising the step of administering the antibody to a non-human animal infected with a pathogen, and determining whether the antibody ameliorates the infectious disease in the non-human animal.

37. A method for identifying an antibody potentially useful for the treatment of an autoimmune disease comprising carrying out the method of claim 25 or 32, further comprising the step of administering the antibody to a non-human animal suffering from an autoimmune disease, and determining whether the antibody ameliorates the autoimmune disease in the non-human animal.

38. A method for screening a molecule for the ability to modulate, directly or indirectly, antigen presentation activity of heat shock protein receptor positive cells comprising:
(a) contacting a molecule with: (i) a purified complex of a heat shock protein and a peptide; and (ii) purified heat shock protein receptor positive cells;
(b) measuring antigen presentation by said heat shock protein receptor positive cells in the presence of said molecule; and
(c) comparing the antigen presentation activity by the purified heat shock protein receptor positive cells in the presence of the molecule with the antigen presentation activity by purified heat shock protein receptor positive cells in the absence of the molecule,
wherein a lower or higher degree of antigen presentation indicates that the molecule modulates the antigen presentation activity of the heat shock protein receptor positive cells.

39. The method of claim 27, 32, or 38, wherein measuring antigen presentation is carried out by measuring representation of a peptide by an MHC molecule.

40. The method of claim 26 or 38, wherein the molecule is a peptide or protein, or derivative, analog or fragment thereof.

41. The method of claim 26 or 38, wherein the molecule is attached to a solid surface.

42. The method of claim 24, 25, 26, 27, 32, or 38, wherein the heat shock protein receptor positive cells are macrophage or dendritic cells.

43. The method of claim 24, 25, 26, 27, 32, or 38, wherein the heat shock protein receptor is selected from the group consisting of an Hsp70 receptor, an Hsp 90 receptor, and a gp96 receptor.

44. The method of claim 24, 25, 26, 27, 32, or 38, wherein the heat shock protein receptor positive cells are purified from heat shock protein receptor negative cells.

45. The method of claim 26 or 38, wherein the molecule is purified.

46. The method of claim 26 or 38, wherein the molecule is a small organic molecule or a nonpeptide.

47. The method of claim 46, wherein the nonpeptide is a member of a nonpeptide library.

48. The method of claim 46, wherein the small organic molecule is a member of a small molecule library.

49. A method for identifying a molecule potentially useful for the treatment of cancer comprising carrying out the method of claim 24, 26, 27, or 38, further comprising the step of administering the molecule to a non-human animal having a tumor, and determining whether the molecule alters tumor progression in the non-human animal.

50. A method for identifying a molecule potentially useful for the treatment of an infectious disease comprising carrying out the method of claim 24, 26, 27, or 38, further comprising the step of administering the molecule to a non-human animal infected with a pathogen, and determining whether the molecule ameliorates the infectious disease in the non-human animal.

51. A method for identifying a molecule potentially useful for the treatment of autoimmune disease comprising carrying out the method of claim 24, 26, 27, or 38, further comprising the step of administering the molecule to a non-human animal suffering from an autoimmune disease, and determining whether the molecule ameliorates the autoimmune disease in the non-human animal.

52. A method for screening a peptide library for the ability to modulate heat shock protein receptor activity comprising:
(a) contacting heat shock protein receptor positive cells with a member of a peptide library; and
(b) comparing the level of heat shock protein receptor binding activity in the heat shock protein receptor positive cells contacted with the member of the peptide library to the amount of heat shock protein receptor binding activity in the heat shock protein receptor positive cells not so contacted,
wherein an increase or decrease in the amount of heat shock protein receptor binding activity in the contacted heat shock protein receptor positive cells relative to the amount of heat shock protein receptor binding activity in the heat shock protein receptor positive cells not so contacted indicates that the member of the peptide library has the ability to modulate heat shock protein receptor activity.

53. The method of claim 52 wherein the level of heat shock protein receptor binding activity is assayed by measuring the ability of the member of the peptide library to bind to the heat shock protein receptor positive cells.

54. The method of claim 52 wherein the heat shock protein receptor binding activity is the ability to interact with a heat shock protein receptor antibody.

55. The method of claim 52 wherein the member of the peptide library is attached to a solid surface.

56. The method of claim 52, wherein the heat shock protein receptor is selected from the group consisting of an Hsp70 receptor, an Hsp 90 receptor, and a gp96 receptor.

57. The method of claim 52, wherein the heat shock protein receptor positive cells are purified from heat shock protein receptor negative cells.

58. A method for identifying a molecule potentially useful for the treatment of cancer comprising carrying out the method of claim 52, further comprising the step of administering the member of the peptide library to a non-human animal having a tumor, and determining whether the molecule alters tumor progression in the non-human animal.

59. A method for identifying a molecule potentially useful for the treatment of an infectious disease comprising carrying out the method of claim 52, further comprising the step of administering the member of the peptide library to a non-human animal infected with a pathogen, and determining whether the molecule ameliorates the infectious disease in the non-human animal.

60. A method for identifying a molecule potentially useful for the treatment of an autoimmune disease comprising carrying out the method of claim 52, further comprising the step of administering the molecule to a non-human animal suffering from an autoimmune disease, and determining whether the molecule ameliorates the autoimmune disease in the non-human animal.

* * * * *